US009205115B2

(12) United States Patent
Jacobsen

(10) Patent No.: US 9,205,115 B2
(45) Date of Patent: Dec. 8, 2015

(54) BACILLUS ISOLATES AND METHODS OF THEIR USE TO PROTECT AGAINST PLANT PATHOGENS AND VIRUS TRANSMISSION

(71) Applicant: MONTANA STATE UNIVERSITY, Bozeman, MT (US)

(72) Inventor: Barry J. Jacobsen, Bozeman, MT (US)

(73) Assignee: Montana State University, Bozeman, MT (US)

( * ) Notice: Subject to any disclaimer, the term of this patent is extended or adjusted under 35 U.S.C. 154(b) by 0 days.

(21) Appl. No.: 13/966,565

(22) Filed: Aug. 14, 2013

(65) Prior Publication Data

US 2014/0056864 A1  Feb. 27, 2014

Related U.S. Application Data

(63) Continuation of application No. 13/175,614, filed on Jul. 1, 2011, now Pat. No. 8,524,222, which is a continuation-in-part of application No. 12/557,975, filed on Sep. 11, 2009, now Pat. No. 8,025,875, which is a continuation-in-part of application No. 11/361,283, filed on Feb. 24, 2006, now abandoned.

(51) Int. Cl.
*A61K 35/74* (2015.01)
*A01N 63/02* (2006.01)
*C12R 1/07* (2006.01)

(52) U.S. Cl.
CPC ............... *A61K 35/74* (2013.01); *A01N 63/02* (2013.01); *C12R 1/07* (2013.01)

(58) Field of Classification Search
None
See application file for complete search history.

(56) References Cited

U.S. PATENT DOCUMENTS

| 3,818,104 | A | | 6/1974 | Zielinski |
| 6,031,153 | A | * | 2/2000 | Ryals et al. .................. 800/279 |
| 8,025,875 | B2 | | 9/2011 | Jacobsen et al. |
| 8,246,965 | B2 | | 8/2012 | Jacobsen et al. |
| 8,524,222 | B2 | | 9/2013 | Jacobsen et al. |
| 2005/0244394 | A1 | * | 11/2005 | DeChant et al. ......... 424/93.461 |
| 2006/0029576 | A1 | * | 2/2006 | Huang et al. ................. 424/93.4 |
| 2007/0224179 | A1 | | 9/2007 | Jacobsen et al. |
| 2010/0092442 | A1 | | 4/2010 | Jacobsen et al. |
| 2011/0318386 | A1 | | 12/2011 | Jacobsen et al. |
| 2012/0003197 | A1 | | 1/2012 | Jacobsen et al. |
| 2014/0056864 | A1 | * | 2/2014 | Jacobsen .................... 424/93.46 |

OTHER PUBLICATIONS

Barbagus et al. (Biological Control. 2004; 30: 342-350).*
Neher, Oliver Thomas. Disease control and plant defense pathways induced by Bacillus mojavensis isolate 203-7 and Bacillus mycoides isolate BmJ. Diss. Montana State University-Bozeman, College of Agriculture, 2008.*

Kloepper et al. (Phytopathology. 2004; 94 (11): 1259-1266).*
Alström, S., "Induction of Disease Resistance in Common Bean Susceptible to Halo Blight Bacterial Pathogen After Seed Bacterisation With Rhizosphere Pseudomonads," Journal of Genetic and Applied Microbiology, 37:495-501 (1991), USA.
Alvarez et al., "Reactive Oxygen Intermediates Mediate a Systemic Signal Network in the Establishment of Plant Immunity", Cell, 92:773-784, Mar. 20, 1998.
Andrews, J.H., "Biological Control in the Phyllosphere," Annual Review of Phytopathology, 30:603-635 (1992), USA.
Bargabus, R.L., et al., "Bacillus Mycoides Isolate Bac J Elicits an Oxidative Burst Independent of Hypersensitive Cell Death," APS Abstracts of Presentations (2003) APS Annual Meeting, Aug. 9-13, 2003, Charlotte, NC, USA.
Bargabus, R.L., et al., "Characterisation of Systemic Resistance in Sugar Beet Elicited by a Non-Pathogenic, Phyllospehere-Colonizing Bacillus Mycoides, Biological Control Agent," (2003) Physiological and Molecular Plant Patholgy (2002) 61, 289-298, USA.
Bargabus, R.L., et al., "Elicitation of ISR by a Nonpathogenic Phyllosphere Inhabiting Bacterium," APS Annual Meeting, Aug. 25-29, 2001 Poster Abstract, Charlotte, NC, USA.
Bargabus, R.L., et al., "Host-response Based Screening of Biological Control Agents," APS Abstracts of Presentations (2002) APS Annual Meeting, Jul. 27-31, 2002, Midwest Express Center, Milwaukee, Wisconsin, USA.
Bargabus, R.L., et al., "Oxidative Burst Elicited by Bacillus Mycoides Isolate Bac J, a Biological Control Agent, Occurs Independently of Hypersensitive Cell Death in Sugar Beet," American Phytopathological Society vol. 16, No. 12, 2003, pp. 1145-1153, USA.
Bargabus, R.L., et al., "Screening for the Identification of Potential Biological Control Agents That Induce Systemic Acquired Resistance in Sugar Beet," Department of Plant Sciences and Plant Pathology, Montana State University, Biological Control, 30:342-350 (2004), USA.
Bargabus-Larson, R.L., et al., "Biocontrol Elicited Systemic Resistance in Sugarbeet is Salicylic Acid Independent and NPR1 Dependent," USDA, Agricultural Research Service, Sugarbeet Research Unit, 1701 Centre Avenue, Fort Collins, Colorado and Montana State University, Biocontrol Elicited Systemic Resistance, pp. 17-33, Jan.-Jun. 2007, USA.
Chen et al., "Biological control of grapevine crown gall: purification and partial characterisation of an antibacterial substance produced by Rahnella aquatilis strain HX2", Eur. J. Plant Phathol. 2009, 124:427-437.

(Continued)

*Primary Examiner* — Shanon A Foley
(74) *Attorney, Agent, or Firm* — Cooley LLP

(57) ABSTRACT

Methods of inducing systemic acquired resistance to infection in a plant are provided. The methods comprise applying a composition comprising a *Bacillus* control agent to said plant wherein said plant is capable of producing defense proteins. Also provided are, methods for controlling one or more plant diseases, methods for preventing plant virus transmission, methods for preventing and/or treating soil-borne plant pathogens using the *Bacillus* control agent of the present invention, and methods of generating bacterial spores. In addition, synergistic biocontrol combinations and methods of using the same are provided.

16 Claims, 6 Drawing Sheets

(56) References Cited

OTHER PUBLICATIONS

Figure 1:
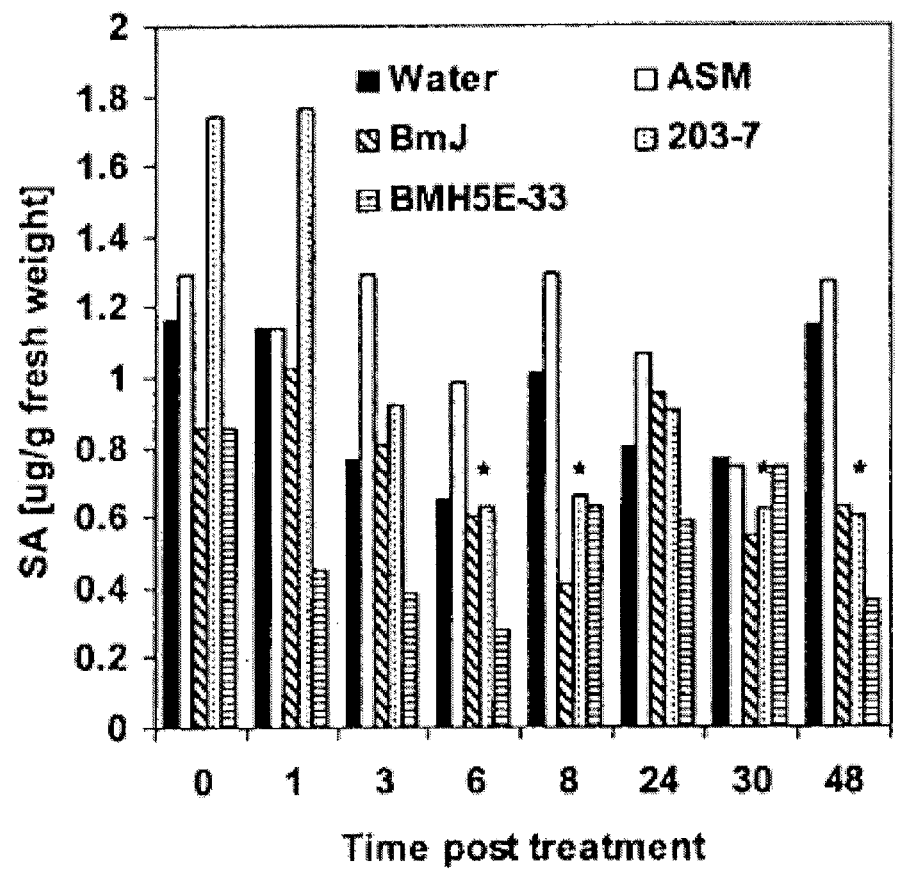

Cheng et al., "Effective Control of Armyworm, Spodoptera exigua (Hubner), on Green Onion by the Ovicidal Action of Bifenthrin", Jour. Agric. Res. China, 1988, 37(3):320-327.

Doke, N., "Generation of Superoxide Anion by Potato Tuber Protoplasts During the Hypersensitive Response to Hyphal Wall Components of Phytophthora Infestans and Specific Inhibition of the Reaction by Suppressors of Hypersensitivity," Physiological Plant Patholom, 23:359-367 (1983), USA.

Enya et al., "Culturable Leaf-Associated Bacteria on Tomato Plants and Their Potential as Biological Control Agents", Microbial Ecology, 2007, 53:524-536.

Garbelotto et al., "Efficacy of phosphonic acid, metalaxyl-M and copper hydroxide against Phytophthora ramorum in vitro and in planta", Plant Pathology, 2008, doi: 10.1111/j.1365-3059.2008. 01894 : 1-9.

Gust et al., "Biotechnological concepts for inproving plant innate immunity," Curr. Opin. Biotechnol. 21:204-210 (2010).

Haye et al. "Predictive value of biological control agents attributes for introduction: Peristenus digoneutis as a case study", Proceedings of the Third International Symposium on Biological Control of Arthropods, 2008, 403-415.

Jacobsen et al., "Cercospora Leaf Spot Control Research at Sidney, MT IN 1998", Jan. 2000, 1999 Sugarbeet Research and Extension Reports, vol. 30, pp. 287-288.

Jacobsen et al., "Fungicide and Biological Control Alternatives to TPTH for Cercospora Leaf Spot Control", Jan. 1999, 1998 Sugarbeet Research and Extension Reports, vol. 29, pp. 350-356.

Jacobsen et al., "Integrated Management of Cercospora Leaf Spot", Jan. 1998, 1997 Sugarbeet Research and Extension Reports, vol. 28, pp. 317-320.

Jacobsen et al., "Integration of *Bacillus* sp. biological seed treatments with apron-thiram and apron-thiram-tachigaren seed treatments for biological control of pythium and aphanomyces seedling diseases", and "Integrated Management strategies for Rhizoctonia Crown and Root Rot", Jan. 2002, 2001 Sugarbeet Research and Extension Reports, vol. 32, pp. 262-265.

Jacobsen et al., "Management of Cercospora Leaf Spot in Western North Dakota and Eastern Montana", Jan. 2001, 2000 Sugarbeet Research and Extension Reports, vol. 31, pp. 273-276.

Jacobsen, B.J., et al., "Commericalization of Bacillus Mycoides Isolate BmJ as a Broad Spectrum Biological Plant Disease Control Agent," Phytopathology 97:S50, USA.

Jacobsen, B.J., et al., "The Role of Bacillus-based Biological Control Agents in Integrated Pest Management Systems," Abstracts of Special Session Presentations APS Annual Meeting Aug. 9-13, 2003, Charlotte, NC, USA.

Johnson, C., et al., "Salicylic Acid and NPR1 Induce the Reqruitment of Trans-Activating TGA Factors to a Defense Gene Promoter in Arabidopsis," The Plant Cell, vol. 15, 1846-1858 (2003), USA.

Kloepper et al., "Induced Systemic Resistance and Promotion of Plant Growth by *Bacillus* spp.", 2004, Phytopathology. 94:1259-1266.

Kuc, J., "Induced Immunity to Plant Disease," BioScience, 32:854-860 (1982), USA.

Larson, B.J., et al., "Integrating Fungicides and a Bacillus Mycoides Biological Control Agent to Manage Cercospora Leaf Spot Resistance to Fungicides," APS Abstracts of Presentations, APS 2002 Annual Meeting, Jul. 27-31, 2002, Midwest Express Center, Milwaukee, Wisconsin, USA.

Matsuda et al., "Control of the Bacterial wilt of Tomato Plants by a Derivative of 3-Indolepropionic Acid Based on Selective Actions on Ralstonia solanacearum", Journal of Agricultural Food Chemistry, 1998, 46:4416-4419.

Neher et al., "Defense pathways activated by Bacillus mojavensis isolate 203-7 and B. mycoides isolate BmJ as elucidated by Arabidopsis mutants", Abstract of Presentations, Sep. 11, 2008, X[th] meeting of the working group, biological control of fungal and bacterial plant pathogens, International Organization for Biological and Integrated Control of Noxious Animals and Plants. Interlaken, Switzerland.

Neher, O.T., et al., "The Control of Anthracnose of Cucurbits Caulsed by *Glomerella cingulata* Var. Orbiculare by Foliar Applications of Bacillus Mycoides Isolate BmJ," Phytopathology 97: S83, USA.

Pieterse, C.M.J., et al., "Systemic Resistance in Arabidopsis Induced by Biocontrol Bacteria is Independent of Salicylic Acid Accumulation and Pathogenesis-related Gene Expression," The Plant Cell. 8:1225-1237 (1996), USA.

Sampson, M.N., et al., "Involvement of Chitinases of Bacillus Thuringiensis During Pathogenesis in Insects," Microbiology, 144:2 189-194 (1998), USA.

Santos, et al., "In a Compatible Plant-pathogen Interaction, a Single, Rapid Burst of Hydrogen Peroxide is Observed," MPMI vol. 14, No. 1, 2001, pp. 86-89. Publication No. M-2000-1117-01N, The American Phytopathological Society (2001), USA.

Sequeira, L., "Mechanisms of Induced Resistance in Plants," Annual Review of Microbiology, 37:5, 1-79 (1983), USA.

Silva et al., "Induction of Systemic Resistance by Bacillus cereus Against Tomato Foliar Diseases Under Field Conditions," J. Phytopathology 152:371-375 (2004).

Tally, A., et al., "Commercial Development of Elicitors of Induced Resistance to Pathogens," Induced Plant Defenses Against Pathogens and Herbivores (A.A. Agrawal, S. Tuzun, and E. Bent, eds.) St. Paul: APS Press, 357-369 (1999), USA.

Wei, G., et al., "Induction of Systemic Resistance of Cucumber to Colletotrichum Orbiculare by Select Strains of Plant Growth-promoting Rhizobacteria," Phytopathology, 81:1508-1512 (1991), USA.

Zaitlin et al., "Advances in Understanding Plant Viruses and Virus Diseases", Annual Review in Phytopathology, 2000, 38:117-143.

Zietlow, O.T., et al., "Induced Systemic Resistance in Cucumber to *Glomerella cingulata* Var. Orbiculare and Pseudomans Syringae pv. Lachrymans by Bacillus Mycoides, Isolate BacJ and Bacillus Pumilus, Isolate MSU 203-7," APS Abstracts of Presentations, 2004 Annual Meeting of the American Phytological Society, USA.

Jacobsen et al., "Integrated Control of Soilborne Diseases on Sugar Beet with Antagonistic Bacteria and Fungicides", 1997 Sugarbeet Research and Extension Reports, vol. 28, (1997).

Jacobsen, B.J., et al., "Commericalization of Bacillus Mycoides Isolate BmJ as a Broad Spectrum Biological Plant Disease Control Agent," Phytopathology 97:S50, USA (2003).

Jacobsen et al., "Seed Treatments for Control of Pythium and Aphanomyces Black Root Rot", 1998 Sugarbeet Research and Extension Reports, vol. 29, (1998).

Kloepper et al., "Induced Systemic Resistance and Promotion of Plant Growth by *Bacillus* spp.", Phytopathology. 94:1259-1266 (2004).

Neher,O.T., et al., "The Control of Anthracnose of Cucurbits Caulsed by *Glomerella cingulata* Var. Orbiculare by Foliar Applications of Bacillus Mycoides Isolate BmJ," Phytopathology 97: S83, USA (2007).

\* cited by examiner

BACILLUS ISOLATES AND METHODS OF THEIR USE TO PROTECT AGAINST PLANT PATHOGENS AND VIRUS TRANSMISSION

CROSS-REFERENCE TO RELATED APPLICATIONS

This application claims priority to U.S. patent application Ser. No. 13/175,614, filed Jul. 1, 2011, now U.S. Pat. No. 8,524,222, which is itself a continuation-in-part of U.S. patent application Ser. No. 12/557,975 filed on Sep. 11, 2009, now U.S. Pat. No. 8,025,875, which is a continuation-in-part of U.S. patent application Ser. No. 11/361,283 filed on Feb. 24, 2006, each of which is hereby incorporated by reference in its entirety for all purposes.

GOVERNMENT RIGHTS STATEMENT

This invention was made with government support under grant number 2001-35316-11109 awarded by United States Department of Agriculture (USDA)/CSREES, and under grant number 2005-33610-16085 awarded by USDA. The government has certain rights in the invention.

FIELD OF THE INVENTION

This invention generally relates to methods of inducing pathogen resistance in plants, such as inducing systemic acquired resistance to infection in plants. In one aspect, this invention relates to methods of inducing systemic acquired resistance to infection in plants comprising applying a *Bacillus* control agent comprising *Bacillus mojavensis* isolate 203-7 and/or *Bacillus mycoides* isolate BmJ to one or more plants. The present invention also relates to the field of bacterial spore production for biopesticides. In one aspect, the present invention relates to novel methods of generating *Bacillus* spores.

BACKGROUND OF THE INVENTION

Effective biological control of plant diseases with epiphytic microbes has been documented for numerous phyllosphere- and rhizosphere-inhabiting organisms. Foliar biological control agents include yeast and filamentous fungi (see Hofstein R and A. Chapple, "Commercial development of biofungicides," Biopesticides: Use and Delivery (Hall F R, Menn J J, eds.), Totowa: Humana Press (1999); and Sutton, J. C. and G. Peng, "Manipulation and vectoring of biocontrol organisms to manage foliage and fruit diseases in cropping systems," Annual Review of Phytopathology, 31:473-493 (1993)) as well as bacteria; including both gram (−) species such as *Erwinia* sp. and *Pseudomonas* sp. (see Andrews, J. H., "Biological control in the phyllosphere," Annual Review of Phytopathology, 30:603-635 (1992)), and gram (+) organisms such as *Bacillus* sp. See Kokalis-Burelle, N., P. A. Backman, R Rodriquez-Kabana, and L. D. Ploper, "Potential for biological control of early leafspot of peanut using *Bacillus cereus* and chitin as foliar amendments," Biological Control, 2:321-328 (1992). Biological control agents applied to the rhizosphere include Pseudomonads (see Alstrom, S., "Induction of disease resistance in common bean susceptible to halo blight bacterial pathogen after seed bacterisation with rhizosphere pseudomonads," Journal of Genetic and Applied Microbiology, 37:495-501 (1991); van Peer, R, G. J. Niemann, and B. Schippers, "Induced resistance and phytoalexin accumulation in biological control of *fusarium* wilt of carnation by *Pseudomonasa* sp. strain WCS417r," Phytopathology, 81:728-734 (1991); and van Loon L. C. and C. M. J. Pieterse, "Biological control agents in signaling resistance," Biological Control of Crop Diseases (Gnanamanickan S S, ed.), New York: Mercel Dekker, Inc, 486 (2002)) as well as *Bacillus* sp. (see Zhang, S., M. S. Reddy, N. Kokalis-Burelle, L. W. Wells, S. P. Nightengale, and J. W. Kloepper, "Lack of induced systemic resistance in peanut to late leaf spot disease by plant growth-promoting rhizobacteria and chemical elicitors," Plant Disease, 85(8):879-884 (2001); and Murphy, J. F., G. W. Zehnder, D. J. Schuster, E. J. Sikora, J. E. Polston, and J. W. Kloepper, "Plant growth-promoting rhizobacterial mediated protection in tomato against Tomato mottle virus," Plant Disease, 84(7):779-784 (2000)) that are classically referred to as plant growth-promoting rhizobacteria. For the most part biological disease control is attributed to direct antagonism against the pathogen via production of antibiotics or hydrolytic enzymes, or through competition for nutrients. See Weller. D. M., "Biological control of soil-borne plant pathogens in the rhizosphere with bacteria." Annual Review of Phytopathology. 26:379-407 (1988). However, plant growth-promoting rhizobacteria and rhizosphere inhabiting fungi have been shown to stimulate the induction of systemic resistance responses within the plant. See van Peer. R. G. J. Niemann. and B. Schippers, "Induced resistance and phytoalexin accumulation in biological control of *fusarium* wilt of carnation by *Pseudomonasa* sp. strain WCS417r." Phytopathology, 81:728-734 (1991); Wei. G. J. W. Kloepper. and S. Tuzun, "Induction of systemic resistance of cucumber to *Colletotrichum orbiculare* by select strains of plant growth-promoting rhizobacteria," Phytopathology, 81:1508-1512 (1991); van Loon, L. C. and C. M. J. Pieterse, "Biological control agents in signaling resistance." Biological Control of Crop Diseases (Gnanamanickan. S. S., ed.). New York: Mercel Dekker, Inc. 486 (2002). All publications mentioned above are incorporated herein by reference in their entireties for all purposes.

Systemic induced resistance (SIR) has been described in many plant systems, most notably tobacco, bean, tomato, cucumber, and *Arabidopsis thaliana*. See Ross, A F., "Localized acquired resistance to plant virus infection in hypersensitive hosts," Virology, 14:329-339 (1961); Kuc, J., "Induced immunity to plant disease," BioScience, 32:854-860 (1982); Ryals, J. A., U. H. Neuenschwander, M. G. Willits, A. Molina, H. Y. Steiner, and M. D. Hunt, "Systemic acquired resistance," The Plant Cell. 8:1809-1819 (1996); and van Loon, L. C. and C. M. J. Pieterse, "Biological control agents in signaling resistance." Biological Control of Crop Diseases (Gnanamanickan. S. S., ed.). New York: Mercel Dekker, Inc. 486 (2002). The broad-spectrum resistance makes an otherwise susceptible plant resistant to a wide array of subsequent pathogen attacks. See Kuc, J. "Induced immunity to plant disease," BioScience, 32:854-860 (1982); and Hutcheson, S. W., "Current concepts of 'active defense in plants." Annual Review of Phytopathology, 36:59-90 (1998). Elicitation of systemic disease resistance in plants has thus far been achieved through treatment by three types of stimuli: necrotizing pathogens (see Pieterse, C. M. J., S. C. M. van Wees. E. Hoffland, J. A. van Pelt, and L. C. van Loon, "Systemic resistance in *Arabidopsis* induced by biocontrol bacteria is independent of salicylic acid accumulation and pathogenesis-related gene expression," The Plant Cell, 8:1225-1237 (1996); Ross, A F., "Localized acquired resistance to plant virus infection in hypersensitive hosts," Virology, 14:329-339 (1961); Ross. A F., "Systemic acquired resistance induced by localized virus infection in plants," Virology. 14:340-358 (1961); and Kuc, J., "Induced immunity to plant disease." BioScience. 32:854-860 (1982)), secondary signal molecules (Le. salicylic acid, SA) (see White, R. F., "Acetylsalicylic acid (aspirin) induces resistance to tobacco mosaic virus in tobacco," Virology. 99:410-412 (1979)) and their functional analogs (e.g. 2,6-dichloroisonicotinic acid, INA (see Metraux, J. P., P. Ahl-Goy, T. Staub, J. Speich, A Steinemann, J. Ryals, and E. Ward, "Induced resistance in cucumber in response to 2,6-dichloroisonicotinic acid and pathogens," Advances in Molecular Genetics of Plant-Microbe Interactions, Vol. 1. (H. Hennecke, D. P. S. Verma, eds.), Dordrecht: Kluwer Academic Publishers, 432-439 (1991)) and acibenzolar-S-methyl. ASM (see Tally, A, M. Oostendorp, K. Lawton, T. Staub, and B. Bassi, "Commercial development of elicitors of induced resistance to pathogens," Induced Plant Defenses Against Pathogens and Herbivores (AA Agrawal, S. Tuzun, and E. Bent, eds.) St. Paul: APS Press, 299-318 (1999)), and plant growth-promoting rhizobacteria introduction into the rhizosphere. See Alstrom, S., "Induction of disease resistance in common bean susceptible to halo blight bacterial pathogen after seed bacterisation with rhizosphere pseudomonads," Journal of Genetic and Applied Microbiology, 37:495-501 (1991); van Loon, L. C. and C. M. J. Pieterse, "Biological control agents in signaling resistance," Biological Control of Crop Diseases (Gnanamanickan, S. S., ed.), New York: Mercel Dekker, Inc, 486 (2002); Wei, G., J. W. Kloepper, and S. Tuzun, "Induction of systemic resistance of cucumber to *Colletotrichum orbiculare* by select strains of plant growth-promoting rhizobacteria," Phytopathology, 81:1508-1512 (1991); Zhang, S., M. S. Reddy, N. Kokalis-Burelle, L. W. Wells, S. P. Nightengale, and J. W. Kloepper, "Lack of induced systemic resistance in peanut to late leaf spot disease by plant growth-promoting rhizobacteria and chemical elicitors," Plant Disease, 85(8):879-884 (2001); and Murphy, J. F., G. W. Zehnder, D. J. Schuster, E. J. Sikora, J. E. Polston, and J. W. Kloepper, "Plant growth-promoting rhizobacterial mediated protection in tomato against Tomato mottle virus," Plant Disease, 84(7):779-784 (2000). Additionally, oomycete and fungal hyphal wall fragments (see Doke, N., "Generation of superoxide anion by potato tuber protoplasts during the hypersensitive response to hyphal wall components of *Phytophthora infestans* and specific inhibition of the reaction by suppressors of hypersensitivity," Physiological Plant Pathology, 23:359-367 (1983); and Anderson, A. J., "Studies on the structure and elicitor activity of fungal glucans," Canadian Journal of Botany, 58:2343-2348 (1980)), bacterial cell wall fractions (lipopolysaccharides) (see Sequeira, L., "Mechanisms of induced resistance in plants," Annual Review of Microbiology, 37:51-79 (1983), and phytohormones (see Cohen, Y., M. Reuveni, and A. Baider, "Local and systemic activity of BABA (DL-3-aminobutyric acid), against *Plasmopara viticola* in grapevines," European Journal of Plant Pathology, 105(4):351-361 (1999); Oka, Y., Y. Cohen, and Y. Spiegel, "Local and systemic induced resistance to the root-knot nematode in tomato by DL-beta-amino-n-butyric acid," Phytopathology, 89(12): 1138-1143 (1999); and Cohen, Y. R., "Aminobutyric acid-Induced Resistance Against Plant Pathogens," Plant Disease, 86(5):448-457 (2002)) have SIR-displayed induction capability. All publications mentioned above are incorporated herein by reference in their entireties for all purposes.

Two systemic resistance pathways have been described: 1) systemic acquired resistance, which utilizes salicylic acid as a secondary signal molecule and leads to the production of pathogenesis-related (PR) proteins (see Delaney, T. P., "Genetic Dissection of Acquired Resistance to Disease," Plant. Physiology, 113:5-12 (1997)) and 2) induced systemic resistance, which utilizes jasmonates and ethylene as secondary signal molecules and controls disease independently of PR-protein production (see Pieterse, C. M. J., S. C. M. van Wees, J. A. van Pelt, M. Knoester, R. Laan, H. Gerrits, P. J. Weisbeek, and L. C. van Loon, "A Novel Signaling Pathway Controlling Induced Systemic Resistance in *Arabidopsis*," The Plant Cell, 10:1571-1580 (1998)). All publications mentioned above are incorporated herein by reference in their entireties for all purposes.

Systemic resistance results in the activation of defenses in uninfected parts of the plant. As a result, the entire plant is more resistant to infection. The systemic resistance is long lasting and often confers broad-based resistance to different pathogens.

One of the issues surrounding systemic resistance is the occurrence of necrotic cell death at the site of application of the agent that induces systemic resistance.

Increased societal concerns related to the use of agrichemicals and genetically modified organisms as a means of managing crop diseases has prompted interest in methods of biological control. A biological control agent capable of inducing systemic resistance would provide a method of increasing disease resistance in a plant without the use of agrichemicals. Of particular interest would be a biological control agent capable of inducing systemic resistance without inducing necrotic cell death.

Thus, a need exists for new biological control agents capable of inducing systemic induced resistance in plants. A need also exists for new methods of identifying new biological control agents capable of inducing systemic resistance in plants.

*Bacillus* spores can potentially be used as biocontrol agents for suppressing various plant diseases. See, e.g., Emmert E A B, Handelsman J (1999) Biocontrol of plant disease-a (Gram-) positive perspective. FEMS Microbiol. Lett. 171:1-9; Shoda M (2000) Bacterial control of plant diseases. J. Biosci. Bioeng. 89:515-521; Montesinos E (2003) Development, registration and commercialization of microbial pesticides for plant protection. Int. Microbiol. 6:245-252. Spores are the preferred form for commercial delivery as spores are more efficient and less expensive to produce and more stable than freeze dried cells. Such biocontrol agents are desirable over chemical agents, which are often harmful to the environment and to humans. However, the current high costs of spore production caused by inefficiencies in culturing and fermentation methods have prevented the widespread use of *Bacillus* spores to control plant disease.

Many attempts have been made to enhance spore yields, particularly with *Bacillus subtilis* cells. See, e.g., Monteiro S (2005) A Procedure for High-Yield Spore Production by *Bacillus subtilis*. Biotechnol. Prog. 21:1026-1031; Hageman J H, et al., (1984) Single, chemically defined sporulation medium for *Bacillus subtilis* growth, sporulation, and extracellular protease production. J. Bacteriol. 160:438-441; Dingman, D W and Stably, D P (1983) Medium Promoting Sporulation of *Bacillus larvae* and Metabolism of Medium Components. Appl. Environ. Microbiol. 46(4):860-869; Warriner, K. and Waites, W. M. (1999) Enhanced Sporulation in *Bacillus subtilis* Grown on Medium Containing Glucose: Ribose. Letters in Applied Microbiology 29:97-102; Chen, Z., et al., (2010) Greater Enhancement of *Bacillus subtilis* Spore Yields in Submerged Cultures by Optimization of Medium Composition Through Statistical Experimental Designs. Appl. Microbiol. Biotechnol. 85:1353-1360. Researchers have also adapted known spore culture methods in attempts to produce spores of *Bacillus mycoides*. See, for example, Bowen et al. (Jul. 20, 2002) The Measurement of *Bacillus mycoides* Spore Adhesion Using Atomic Force Microscopy, Simple Counting Methods, and a Spinning Disk Technique, Biotechnology and Bioengineering, Vol. 79(2): 170-179. However, improved methods for spore production are needed, particularly for other species within the *Bacillus* genus.

SUMMARY OF THE INVENTION

In accordance with the objects outlined above, the present invention provides methods and compositions useful in inducing disease resistance to infection in a plant, comprising applying a *Bacillus* control agent comprising *Bacillus mojavensis* isolate '203-7' having accession number NRRL B-30893 and/or *Bacillus mycoides* isolate 'BmJ' having accession number NRRL B-30890 to the plant, wherein the plant is capable of producing defense proteins. In one embodiment, the disease resistance to infection in the plant is systemic acquired resistance. 'BmJ' is also known as 'Bac J.', *Bacillus mycoides* isolate J, *B. mycoides* J, *Bacillus mycoides* J, or "isolate J". In another embodiment, the systemic acquired resistance is induced in the plant through a salicylic acid independent and jasmonic acid dependent pathway. In another embodiment, the systemic acquired resistance is induced by *Bacillus mycoides* isolate BmJ having accession number NRRL B-30890 in the plant through an NPR1 dependent pathway. In another embodiment, the systemic acquired resistance is induced by *Bacillus mojavensis* isolate 203-7 having accession number NRRL B-30893 in the plant through an NON-EXPRESSOR OF PATHOGENESIS-RELATED GENES1 (NPR1) independent pathway. In another embodiment, the plant is a monocot, for example, the plant is selected from the group consisting of wheat, Arabodpsis, corn (maize), rice, barley, triticale and lily. In another embodiment, the plant is a dicot, for example, the plant is selected from the group consisting of banana, cucurbit, pecan, soybean, sunflower, alfalfa, tomato, cucumber, watermelon, potato, pepper, bean, chrysanthemum, and geranium. In another embodiment, the infection is caused by any kind of infectious (i.e., biotic) agents that affect plants. Examples of such agents/pathogens include but are not limited to an agent or pathogen selected from the group consisting of bacteria, fungi, and viruses. Examples of specific pathogens to be treated using the compositions and methods of the present invention include but are not limited to pathogens selected from the group consisting of *Mycosphaerella fijiensis, Cladosporium caryigenum, Glomerella cingulata, Cercospora beticola, Pseudomonas syringe, Erwinia caratovora, Botrytis cinerea*, and *Fusarium solani* f. sp. *cucurbitae, Alternaria solani, Sclerotinia sclerotiorum, Alternaria solani, Sclerotinia sclerotiorum, Xanthomonas campestris, Pythium aphanidermatum*, and *Podosphora xanthii*. In some other embodiments, the disease is associated with plant viruses, for example, Potato Virus Y, cucumber mosaic virus, tobacco mosaic virus, and squash vein yellowing virus.

The present invention also provides methods of inducing a first systemic acquired resistance in a plant comprising applying a *Bacillus* control agent comprising *Bacillus mojavensis* isolate 203-7 and/or *Bacillus mycoides* isolate BmJ to the plant, wherein the methods further comprise applying a second biological or chemical control agent, and wherein the first systemic acquired resistance is induced in the plant through a salicylic acid independent and jasmonic acid dependent pathway. In one embodiment, the first systemic acquired resistance is induced by *Bacillus mycoides* isolate BmJ having accession number NRRL B-30890 in the plant through an NPR1 dependent pathway. In another embodiment, the first systemic acquired resistance is induced by *Bacillus mojavensis* isolate 203-7 having accession number NRRL B-30893 in the plant through an NPR1 independent pathway. In another embodiment, the second biological or chemical control agent is selected from the group consisting of antifungal agents, antibacterial agents, antiviral agents, and plant activating compounds. The second biological or chemical control agent may or may not also induce the first systemic acquired resistance in the plant and/or induce a second systemic acquired resistance in the plant.

The invention is also directed to methods of screening for biological control agents useful in inducing systemic acquired resistance to infection in a plant.

The present invention, according to one embodiment, is a method of inducing systemic acquired resistance to infection in a plant. The method includes applying to the foliage of the plant a composition comprising a *Bacillus* control agent. The agent is *Bacillus mycoides* isolate BmJ having accession number NRRL B-30890 or *Bacillus mojavensis* isolate 203-7 having accession number NRRL B-30893. According to the invention, the plant is capable of producing defense proteins.

In an alternative embodiment, the present invention is a method of inducing systemic acquired resistance to infection in a plant. The method includes applying to the foliage of said plant a composition comprising a *Bacillus* control agent. The agent is *Bacillus mycoides* isolate BmJ having accession number NRRL B-30890 or *Bacillus mojavensis* isolate 203-7 having accession number NRRL B-30893. According to the invention, the plant does not experience necrotic cell death as a result of said applying of said *Bacillus* control agent.

According to one embodiment of the present invention, the infection to which systemic acquired resistance is induced is selected from the group consisting of bacterial infections, fungal infections, and viral infections. Alternatively, the infection is a *Mycosphaerella fijiensis* (Black sigatoka), *Cladosporium caryigenum* (pecan scab), *Glomerella cingulata* (Anthracnose) or *Cercospora beticola* (*Cercospora* leaf spot) infection. In a further alternative, the infection is a *Pseudomonas syringe* (angular leaf spot) or *Erwinia caratovora* (bacterial vascular necrosis) infection. In a further alternative, the infection is *Botrytis cinerea* or *Fusarium solani* f. sp. *cucurbitae* (Fusarium Crown rot). In some further embodiments, the plant disease is selected from the group consisting of early blight disease (*Alternaria solani*), white mold disease (*Sclerotinia sclerotiorum*), bacterial spot disease (*Xanthomonas campestris*), gray mold (*Botrytis cinerea*), root rotting disease (*Pythium aphanidermatum*), and powdery mildew (*Podosphora xanthii*). In some other embodiments, the disease is associated with plant viruses, for example, Potato Virus Y, cucumber mosaic virus, tobacco mosaic virus, and squash vein yellowing virus.

In one aspect of the invention, either of the above methods also includes applying a biological or chemical control agent. According to one embodiment, the *Bacillus* biological control agent is applied in conjunction with the biological or chemical control agent. Alternatively, the *Bacillus* biological control agent is applied sequentially with the biological or chemical control agent.

The present invention, in accordance with another embodiment, is a plant treated with a *Bacillus* control agent selected from the group consisting of *Bacillus mycoides* isolate BmJ having accession number NRRL B-30890 and *Bacillus mojavensis* isolate 203-7 having accession number NRRL B-30893. The agent induces systemic acquired resistance in said plant. According to this embodiment, the plant does not experience necrotic cell death as a result of said treating with said *Bacillus* control agent and the plant is a dicot plant or a monocot plant. For example, the plant is a Solanaceae species, such as potatoes, tomatoes, peppers, tobaccos, etc; an ornamental plant, such as Geranium plants; or a Cucurbitaceae species, such as cucumbers, squashes, watermelons, cantaloupes, etc. In some embodiments, Solanaceae species is a potato or a tomato; the Cucurbitaceae species is a *Cucumis melon*, a squash or a cucumber; and the ornamental plant is a Geranium species. According to another embodiment, the present invention is a method of screening for a *Bacillus* control agent that induces systemic resistance in a plant. The method includes contacting a plant sample with said *Bacillus* control agent and detecting a property selected from the group consisting of the release of active oxygen species (AOS), chitinase activity and B 1,3 glucanase activity.

In accordance with another aspect, the present invention is a composition for imparting systemic disease resistance in a plant capable of producing defense proteins. The composition includes a *Bacillus* control agent selected from the group consisting of *Bacillus mycoides* isolate BmJ having accession number NRRL B-30890 and *Bacillus mojavensis* isolate 203-7 having accession number NRRL B-30893. Further, the plant is capable of producing defense proteins. This composition can also alternatively include a carrier substance, a biological control agent, and/or a chemical control agent. According to one embodiment, the composition is a solution.

In another embodiment, the present invention is a method of inducing systemic acquired resistance to infection in a plant. The method includes causing the phyllosphere of the plant to be colonized with a *Bacillus* control agent selected from the group consisting of *Bacillus mycoides* isolate BmJ having accession number NRRL B-30890 and *Bacillus mojavensis* isolate 203-7 having accession number NRRL B-30893. The plant in this method is capable of producing defense proteins.

According to an alternative aspect, the present invention is a method of enhancing plant growth by conferring systemic acquired resistance to a plant. The method includes applying to the foliage of the plant a composition comprising a *Bacillus* control agent selected from the group consisting of *Bacillus mycoides* isolate BmJ having accession number NRRL B-30890 and *Bacillus mojavensis* isolate 203-7 having accession number NRRL B-30893. The plant in this method, is capable of producing defense proteins.

The present invention, according to an alternative embodiment, is a method of enhancing plant growth by conferring systemic acquired resistance to a plant. The method includes causing the phyllosphere of the plant to be colonized with a composition comprising a *Bacillus* control agent selected from the group consisting of *Bacillus mycoides* isolate BmJ having accession number NRRL B-30890 and *Bacillus mojavensis* isolate 203-7 having accession number NRRL B-30893. The plant in this method is capable of producing defense proteins.

The present application also provides methods for controlling one or more plant diseases in a plant or a plant part. In some embodiments, the methods comprise applying a biocontrol agent comprising a *Bacillus mycoides* isolate or spores thereof to the plant or the plant part. In some embodiments, the *Bacillus mycoides* isolate is the *Bacillus mycoides* isolate BmJ having accession number NRRL B-30890. In some embodiments, the one or more plant diseases are selected from the group consisting of pecan scab disease (*Cladosporium caryigenum*), Anthracnose disease (*Glomerella cingulata*), angular leaf spot (*Pseudomonas syringe*), early blight disease (*Alternaria solani*), white mold disease (*Sclerotinia sclerotiorum*), bacterial spot disease (*Xanthomonas campestris*), gray mold (*Botrytis cinerea*), root rotting disease (*Pythium aphanidermatum*), and powdery mildew (*Podosphora xanthii*). In some other embodiments, the disease is associated with plant viruses, for example, Potato Virus Y, cucumber mosaic virus, tobacco mosaic virus, and squash vein yellowing virus.

In some embodiments, the plant is a dicot plant or a monocot plant. For example, the plant is a Solanaceae species, such as potatoes, tomatoes, peppers, tobaccos, etc; an ornamental plant, such as Geranium plants; or a Cucurbitaceae species, such as cucumbers, squashes, watermelons, cantaloupes, pumpkins, etc. In some embodiments, Solanaceae species is a potato or a tomato; the Cucurbitaceae species is a *Cucumis melon*, a squash or a cucumber; and the ornamental plant is a Geranium species or a Chrysanthemum species.

The present application also provides methods for preventing or reducing virus infection transmitted by a pathogen transmitter in a plant or a plant part. In some embodiments, the methods comprise applying a biocontrol agent comprising a *Bacillus mycoides* isolate or spores thereof to the plant, the plant part, or the soil around the plant. In some embodiments, the *Bacillus mycoides* isolate is the *Bacillus mycoides* isolate BmJ having accession number NRRL B-30890. Without wishing to be bound by any theory, the methods prevent virus infection transmitted by the pathogen transmitter in one or more ways, including but not limited to, disrupting the normal feeding cycle of the pathogen transmitter; making the plants or plant parts distasteful; repelling the pathogen transmitter from contacting the plants; and restricting the movement of the pathogen transmitter. In some embodiments, the pathogen transmitter is an insect or a mite.

In some embodiments, the virus is potato virus Y transmitted by an aphid, or wheat streak mosaic transmitted by a mite. In some embodiments, the aphid is a green peach aphid and the mite is a wheat curl mite.

The present application also provides methods for inducing disease resistance to a pathogen in a plant or a plant part. In some embodiments, the methods comprise applying a biocontrol agent to the plant, the plant part, or soil around the plant. In some embodiments, the methods comprise foliar application of the biocontrol agent to the plant. In some embodiments, the biocontrol agent comprises a *Bacillus mycoides* isolate or spores thereof. In some embodiments, the *Bacillus mycoides* isolate is the *Bacillus mycoides* isolate BmJ having accession number NRRL B-30890. In some embodiments, the pathogen is a soil-borne root pathogen.

In some embodiments, the soil-borne root pathogen is a *Pythium* species. For example, the *Pythium* species is *Pythium aphanidermatum*.

In some embodiments, the plant is an ornamental plant, for example, a Geranium species or a Chrysanthemum species.

In some embodiments, the foliar application is conducted before, during or after transplantation.

The present application also provides synergistic combinations for controlling one or more plant diseases. In some embodiments, the combinations comprise a first and one or more second agents, wherein the first agent comprises a *Bacillus mycoides* isolate or spores thereof. In some embodiments, the *Bacillus mycoides* isolate is the *Bacillus mycoides* isolate BmJ having accession number NRRL B-30890.

In some embodiments, the second agent can be any agent different from the first agent. In some embodiments, the second agent is selected from the group consisting of bactericides, fungicides, oomycetecides, insecticides, and anti-virus agents. For example, the second agent is a fungicide, such as fungicides comprising one or more strobilurins (e.g., HEADLINE® (strobilurins)), fungicides comprising manganese ethylenebisdithiocarbamate (e.g., MANEX® (Manganese ethylenebisdithiocarbamate)), fungicides as the same as or similar to Manzate® (Mancozeb), fungicides as the same as or similar to SONATA® (*Bacillus pumilus*), etc. In some embodiments, the plant disease is early blight (*Alternaria solani*) or white mold (*Sclerotinia sclerotiorum*) and the second agent is 14, e.g., ENDURA® (boscalid). In some embodiments, the plant disease is associated with a plant virus, for example, a plant virus transmitted by an insect, and the second agent is an insecticide. In some embodiments, the insecticide is a chemical agent, such as pyrethroid. In some embodiments, the insecticide is a systemic biocontrol agent, such as ADMIRE® (Imidacloprid). In some embodiments, the insecticide is a biological agent, such as *Beauveria bassiana*. In some embodiments, the plant virus is potato virus Y or wheat streak mosaic virus. In some embodiments, the potato virus Y is transmitted by an aphid and the wheat streak mosaic virus is transmitted by a mite. In some embodiments, the aphid is a green peach aphid and the mite is a wheat curl mite.

The present application further provides methods for controlling one or more plant diseases on a plant or one or more plant parts. In some embodiments, the methods comprise applying the synergistic combinations of the present application to the plant, the plant parts, or soil around the plant. In some embodiments, plant disease is early blight disease (*Alternaria solani*), and the second agent is HEADLINE® (strobilurins). In some embodiments, the plant disease is bacterial spot (*Xanthomonas campestris*), and wherein the second agent is MANEX® (Manganese ethylenebisdithiocarbamate) or MANZATE® (Mancozeb). In some embodiments, the plant disease is Downey mildew (*Pseudoperonospora cubensis*), and wherein the second agent is SONATA® (*Bacillus pumilus*). In some embodiments, the plant disease is early blight (*Alternaria solani*) or white mold (*Sclerotinia sclerotiorum*) and the second agent is Boscalid, e.g., ENDURA® (boscalid). In some embodiments, the plant disease is associated with a plant virus, for example, a plant virus transmitted by an insect, and the second agent is an insecticide. In some embodiments, the insecticide is a chemical agent, such as pyrethroid. In some embodiments, the insecticide is a systemic biocontrol agent, such as ADMIRE® (Imidacloprid). In some embodiments, the insecticide is a biological agent, such as *Beauveria bassiana*. In some embodiments, the plant virus is potato virus Y or wheat streak mosaic virus. In some embodiments, the potato virus Y is transmitted by an aphid and the wheat streak mosaic virus is transmitted by a mite. In some embodiments, the aphid is a green peach aphid and the mite is a wheat curl mite.

The present invention further provides methods for inducing disease resistance in a plant or a plant part against one or more diseases without causing phytotoxicity. In some embodiments, the methods comprise applying a biocontrol agent comprising a *Bacillus mycoides* isolate or spores thereof to the plant, the plant part, or the soil around the plant. In some embodiments, the *Bacillus mycoides* isolate is the *Bacillus mycoides* isolate BmJ having accession number NRRL B-30890. In some embodiments, the biocontrol agent is applied at 1-100 gram/acre rate with $3\times10^{10}$ spores or cells per gram *Bacillus mycoides* isolate BmJ in the biocontrol agent.

The present invention further provides methods for bacterial sporulation in liquid culture. In some embodiments, the methods comprise culturing bacterial cells in a production medium containing no glucose, or very low concentration of glucose. In one embodiments, the concentration of glucose in the medium is about 1.5 gram/liter, or less that about 1.5 gram/liter, for example, less than about 1.4 gram/liter, less than about 1.3 gram/liter, less than about 1.2 gram/liter, less than about 1.1 gram/liter, less than about 1.0 gram/liter, less than about 0.9 gram/liter, less than about 0.8 gram/liter, less than about 0.7 gram/liter, less than about 0.6 gram/liter, less than about 0.5 gram/liter, less than about 0.4 gram/liter, less than about 0.3 gram/liter, less than about 0.2 gram/liter, less than about 0.1 gram/liter, less than about 0.01 gram/liter, less than about 0.001 gram/liter, or less.

In some embodiments, the medium can comprise one or more protein sources. In some embodiments, the protein sources do not contain glucose, or contain very low concentration of glucose so that the protein sources can provide enough amino acid supplies to the bacteria growth but do not raise the glucose concentration in the medium more than about 1.5 gram/liter. Optionally, the medium can comprise one or more carbon sources that do not contain glucose, or do not raise the glucose concentration in the medium more than about 1.5 gram/liter.

In some embodiments, the methods further comprise removing the resulting bacterial spores from the production medium, drying the bacterial spores, and, optionally, blending the bacterial spores with a carrier.

In some embodiments, the bacterial cells belong to the *Bacillus* genus. In another embodiment, the bacterial cells belong to the species *Bacillus mycoides*. In some embodiments, the *Bacillus mycoides* is the *Bacillus mycoides* isolate BmJ having accession number NRRL B-30890.

The present invention, in another embodiment, involves a production medium containing one or more protein ingredients selected from soybean meal, soy flour, soy protein concentrate, soy peptones, protein products derived from rice, wheat and barley, or combination thereof.

In some embodiments, the production medium has a pH of 5 to 10, for example, the medium has a pH of 7.0 to 7.2.

In some embodiments, the bacterial cells are removed from the medium by means of continuous flow centrifugation or filtration. In one embodiment, the bacterial spores are dried by means of evaporation. According to another embodiment, the final spore concentration after drying is at least 1×10E10 spores per gram, at least 1×10E11 spores per gram, or at least at least 1×10E12 spores per gram.

In another embodiment, the bacterial spores are blended with a carrier, such as attapulgite clay, kaolin-type clay, barden clay, and suitable types of oils, that aids in the suspension of the spores in water and provides a volume of material that is easy to use.

The present invention further provides wettable powder and liquid biocontrol formulations comprising *Bacillus* spores. In some embodiments, the formulations comprise *Bacillus mycoides* spores and one or more carriers. In some embodiments, the *Bacillus mycoides* is *Bacillus mycoides* isolate BmJ having accession number NRRL B-30890.

In some embodiments, the dried bacterial spores can be used to make wettable power formulations. For example, the spores can be mixed with wetting agents or emulsifiers (e.g., surfactant). In some embodiments, the wetting agents are soil wetting agents, such as clays. For example, the wetting agent is selected from the group consisting of attapulgite clay, kaolin-type clays, and Barden clays.

In some embodiments, the liquid biocontrol formulations comprise at least one carrier that is a solvent-refined light paraffinic distillate, such as the solvent-refined light paraffinic distillate having CAS #64741-89-5. In some embodiments, the solvent-refined light paraffinic distillate comprising fatty acid alcohol C12-C14. In some further embodiments, the fatty acid alcohol C12-C14 is ethoxylated. The solvent-refined light paraffinic distillate can be a commercially available product such as Sunspray 7E (EPA Registration No. 00086200008).

In some embodiments, the carrier comprises one or more vegetable oils. For example, the carrier is a methylated vegetable oil. The vegetable oils can be saturated or unsaturated, edible or inedible, include, but are not limited to, canola oil, sunflower oil, safflower oil, peanut oil, bean oil, linseed oil, tung oil, and soybean oil. In some embodiments, the carrier is a methylated soybean oil.

In some embodiments, the liquid formulation has a concentration of $1\times10^9$ spores per ml carrier. The formulation can be further diluted in water to reach a final concentration of $1\times10^7$ spores per ml.

BRIEF DESCRIPTION OF THE DRAWINGS

FIG. 1 depicts a graphic representation of the relationship between systemic resistance and accumulation of salicylic acid ("SA"), according to one embodiment of the present invention.

FIG. 2 depicts a graphic representation relating to the amount of recoverable salicylic acid after extraction, thereby indicating the amount of salicylic acid lost during extraction, according to one embodiment of the present invention.

FIG. 3 depicts a graphic representation of the relationship between the addition of various agents and the activation of NPR1, according to one embodiment of the present invention.

FIG. 4 depicts a schematic representation of a BCA-sugar beet interaction model, in accordance with one aspect of the present invention.

FIG. 5 depicts percent infection of Russet Norkotah potatoes at different times planted at Hermiston, Oreg. Plants were treated either with BmJ at emergence then every 14 days or without treatment. Data are statistically different at day 71 and day 84 @ $P<0.05$, indicating that BmJ is effective in controlling Potato Virus Y (PVY) infection transmitted by aphid.

FIG. 6 depicts percent infection of PVY transmitted by aphids at different times. Plants were treated with or without BmJ (dead or alive).

DETAILED DESCRIPTION OF THE INVENTION

All publications, patents and patent applications, including any drawings and appendices, herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

DEFINITIONS

As used herein, the verb "comprise" as is used in this description and in the claims and its conjugations is used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

The term "bacteria" includes any prokaryotic organism that does not have a distinct nucleus. The term "culturing" refers to the propagation of organisms on or in various kinds of media. "Spore" refers to a dormant cell that can grow into a new organism and is highly resistant to desiccation and heat. "Sporulation" is the process through which cells form spores. A "protein ingredient" is defined as a media component supplying a mixture of amino acids, polypeptides, and/or proteins that supports the growth of bacterial cells.

As used herein, the term "plant" refers to any living organism belonging to the kingdom Plantae (i.e., any genus/species in the Plant Kingdom). This includes familiar organisms such as but not limited to trees, herbs, bushes, grasses, veins, ferns, mosses and green algae. The term refers to both monocotyledonous plants, also called monocots, and dicotyledonous plants, also called dicots. Examples of particular plants include but are not limited to corn, potatoes, roses, apple trees, sunflowers, wheat, rice, bananas, tomatoes, opo, pumpkins, squash, lettuce, cabbage, oak trees, guzmania, geraniums, hibiscus, clematis, poinsettias, sugarcane, taro, duck weed, pine trees, Kentucky blue grass, zoysia, coconut trees, *brassica* leafy vegetables (e.g. broccoli, broccoli raab, Brussels sprouts, cabbage, Chinese cabbage (Bok Choy and Napa), cauliflower, cavalo, collards, kale, kohlrabi, mustard greens, rape greens, and other *brassica* leafy vegetable crops), bulb vegetables (e.g. garlic, leek, onion (dry bulb, green, and Welch), shallot, and other bulb vegetable crops), citrus fruits (e.g. grapefruit, lemon, lime, orange, tangerine, citrus hybrids, pummelo, and other citrus fruit crops), cucurbit vegetables (e.g. cucumber, citron melon, edible gourds, gherkin, muskmelons (including hybrids and/or cultivars of *cucumis* melons), watermelon, cantaloupe, and other cucurbit vegetable crops), fruiting vegetables (including eggplant, ground cherry, pepino, pepper, tomato, tomatillo, and other fruiting vegetable crops), grape, leafy vegetables (e.g. romaine), root/tuber and corm vegetables (e.g. potato), and tree nuts (almond, pecan, pistachio, and walnut), berries (e.g., tomatos, barberries, currants, elderberryies, gooseberries, honeysuckles, mayapples, nannyberries, Oregon-grapes, seebuckthorns, hackberries, bearberries, lingonberries, strawberries, sea grapes, lackberries, cloudberries, loganberries, raspberries, salmonberries, thimbleberries, and wineberries), cereal crops (e.g., corn, rice, wheat, barley, sorghum, millets, oats, ryes, triticales, buckwheats, fonio, and quinoa), pome fruit (e.g., apples, pears), stone fruits (e.g., coffees, jujubes, mangos, olives, coconuts, oil palms, pistachios, almonds, apricots, cherries, damsons, nectarines, peaches and plums), vein (e.g., table grapes, wine grapes), fibber crops (e.g. hemp, cotton), ornamentals, and the like. For a more complete list of representative crop plants see, for example, Glossary of Crop Science Terms: III, Nomenclature, Common and Scientific Names, Crop Science Society of America, July 1992, which is herein incorporated in its entirety.

As used herein, the term "pesticide" refers to composition comprising one or more chemical substances or biological organisms capable of killing or inhibiting a pest. Pests include, but are not limited to, insects, pathogens (e.g., bacterium, fungi, viruses), weeds, molluscs, birds, mammals, fish, nematodes and microbes that compete with humans, e.g., for food. Pesticides can be classified into algicides, avicides, bactericides, fungicides, herbicides, insectcides, miticides/acaricides, molluscicides, nematicides, rodenticides, virucides, et al.

As used herein, the term "plant part" refers to any part of a plant including but not limited to the shoot, root, stem, seeds, stipules, leaves, petals, flowers, ovules, bracts, branches, petioles, internodes, bark, pubescence, tillers, rhizomes, fronds, blades, pollen, stamen, and the like. The two main parts of plants grown in some sort of media, such as soil, are often referred to as the "above-ground" part, also often referred to as the "shoots", and the "below-ground" part, also often referred to as the "roots". For a more comprehensive list of plant parts see, for example, James W. Perry and David Morton (1998) Photo Atlas for Botany, Wadsworth Publishing Company, 141 pages, which is herein incorporated in its entirety.

As used herein, the term "fungicide" refers to a composition comprising one or more chemical substances or biological organisms capable of killing or inhibiting both true fungi and their spores as well as oomycete pathogens, usually in a selective way. Fungicides are used both in agriculture and to fight fungal infections in animals. Fungicide can be either contact or systemic. In agriculture, a contact fungicide kills fungi by direct contact; a systemic fungicide spreads internally through the plant, thereby killing the fungi. Non-limiting examples of fungicides include, but are not limited to, strobilurins (e.g., HEADLINE® (strobilurins)), carboxamides, sulfananilides, phenylsulfamides, azoles, nitrogenous heterocycles, dicarboximides, phthalimides, carbamates (e.g., manganese ethylenebisdithiocarbamate such as MANEX® (Manganese ethylenebisdithiocarbamate), thiocarbamates, formamidines, antibiotics, aromatics, guanidines, organochlorine compounds, organometallics, organophosphorus compounds, nitrophenyl compounds, sulfur heterocyclyl compounds, ureas, inorganics, and others (e.g., benzamacril, carvone, essential oil extract from plants, cedar leaf oil, neem oil, chloropicrin, DBCP, drazoxolon, fenaminosulf, metzoxolon, oxolinic acid, spiroxamine, cymoxanil, metrafenone. Prohexadione calcium, thicyofen, dithane, chlorothalanil, dichlorophen, dicloran, nitrothal-isopropyl, bronopol, diphenylamine, mildiomycin, oxin-copper, cyflufenamide (e.g., N-(cyclopropylmethoxyimino-(6-difluoromethoxy-2,3-difluorophenyl)-methyl)-2-phenylacetamide), UK-2A (antibiotic isolated from *Streptomyces* sp. 517-02), RANMAN™ (Ishihara Sangyo Kaisha, Ltd), and microbe-based products, including but not limited to *Bacillus subtilis*-based products, such as SONATA® (*Bacillus pumilus*). Other examples of fungicides include, MANZATE® (Mancozeb), DITHANE® (Mancozeb), ENDURA® (boscalid), QUADRIS®/AMISTAR® (azoxystrobin), CABRIO® (pyraclostrobin), TANOS® (famoxate+curzate), PRESIDIO® (fluopicolide), REVUS® (mandipropamid), FORUM® (dimethomorph), MANEB®/MANCOZEB® (Manganese ethylenebisdithiocarbamate), RIDOMIL GOLD® SC (mefenoxam), REDOMIL GOLD® Copper (mefenoxam+Cu hydroxide), TERRACLOR®(PCNB), PREVICUR FLEX® (propamocarb), BRAVO® (chlorothalonil), ECHO® (chlorothalonil), fixed copper, ACTIGARD® (acibenzolar-S-methyl), and Streptomycin sulfate. As used herein, the term "bactericide" refers to a composition comprising one or more chemical substances or biological organisms capable of killing or inhibiting bacteria, usually in a selective way.

As used herein, the phrase "systemic acquired resistance (SAR)" refers to a "whole-plant" resistance response that occurs following an earlier localized exposure to a pathogen. SAR is analogous to the innate immune system found in animals, and there is evidence that SAR in plants and innate immunity in animals may be evolutionarily conserved. SAR is important for plants to resist disease, as well as to recover from disease once formed. SAR can be induced by a wide range of pathogens, especially (but not only) those that cause tissue necrosis, and the resistance observed following induction of SAR is effective against a wide range of pathogens. SAR is associated with the induction of a wide range of genes (so called PR or "pathogenesis-related" genes), and the activation of SAR often requires the accumulation of endogenous salicylic acid (SA). The pathogen-induced signal activates a molecular signal transduction pathway that is identified by a gene called NIM1, NPR1 or SAI1 (three names for the same gene) in the model genetic system *Arabidopsis thaliana*. SAR has been observed in a wide range of flowering plants, including dicotyledon and monocotyledon species.

As used herein, the phrase "defense proteins" refers to proteins that are differentially induced at the onset of systemic acquired resistance in a plant.

As used herein, the term "synergy", "synergistic" or "synergism" refers to a situation where two or more agents work together to produce a result not obtainable by any of the agents independently. Synergy also occurs when a combination of agents can control disease that neither agent can control independently. In addition, synergy occurs when a smaller amount of one or both agents, when combined, is required to obtain control of a disease, than when each agent is used independently.

The present invention is directed to methods and compositions useful in inducing systemic acquired resistance (SAR) to infection in a plant. More specifically, the present invention uses a *Bacillus* control agent to induce SAR in plants. Plants in which SAR has been induced are capable of mounting defenses against a wide variety of infections. Thus, treatment of a plant with a *Bacillus* control agent that induces SAR would cause the plant to become more resistant to infections caused by such agents as fungi, bacteria or viruses. For example, treatment of a banana plant with a *Bacillus* control agent that induces SAR would result in a banana plant that is resistant to infection such as Black Sigatoka. In another embodiment, the systemic acquired resistance in the plant is induced through a salicylic acid independent and jasmonic acid dependent pathway. In one embodiment, the systemic acquire resistance is induced by *Bacillus mycoides* isolate BmJ through a NON-EXPRESSOR OF PATHOGENESIS-RELATED GENES1 (NPR1) dependent pathway. In another embodiment, the systemic acquired resistance is induced by *Bacillus mojavensis* isolate 203-7 through an NPR1 independent pathway.

Concerns related to the use of chemicals and genetically modified organisms (GMOs) as a means of managing crop diseases has prompted interest in methods of biological control. A non-pathogenic *Bacillus* control agent capable of inducing systemic resistance would provide a method of increasing disease resistance in a plant without the use of chemicals or GMOs. In addition, the absence of necrosis as a result of such application would be highly desirable. Additionally, it is also desirable to induce systemic resistance by foliar application of a microbe as foliar application provides ease of application and broader range of application methods and equipment.

The invention is also directed to methods of screening for biological control agents useful in inducing systemic acquired resistance to infection in a plant. Such methods as described herein would allow rapid detection of additional *Bacillus* control agents that can be used to induce systemic acquired resistance to infection in a plant.

Accordingly, the present invention provides methods of inducing systemic resistance to infection in plants with a *Bacillus* control agent. By "plant" is meant any organism belonging to the plant or vegetable kingdom. In further preferred embodiments, the plant is a banana, a cucurbit, (including, but not limited to, cucumbers, squash, pumpkins, and cantaloupes and other melons), a pecan, a sugar beet, or a geranium. "Plant" also encompasses parts of plants, as well as whole organisms. For example, the term plant encompasses a leaf or disc from a leaf, roots, stems, seeds, plant protoplasts, plant spores, plant shoots and plant cell cultures.

The plant being treated with *Bacillus* control agent is preferably capable of accumulating salicylic acid, although this may not be required in all cases. Salicylic acid accumulation is indicated for SAR signal transduction. Plants that do accumulate salicylic acid due to treatment with specific inhibitors, epigenetic repression of phenylalanine ammonia-lyase, or transgenic expression of salicylate hydroxylase, which specifically degrades salicylic acid, generally do not exhibit either SAR gene expression or disease resistance (Gaffney et al., 1993; Delaney et al., 1994; Mauch-Mani and Slusarenko 1996; Maher et al., Proc. Natl. Acad. Sci. USA 91, 7802-7806 (1994), incorporated herein by reference; Pallas et al., Plant J. 10, 281-293 (1996), incorporated herein by reference). Plants in which SAR can be induced by a *Bacillus* control agent include, for example, sugar beets, bananas, cucurbits, pecans, and geraniums.

Additionally, the plant being treated with *Bacillus* control agent is capable of producing defense proteins. By "defense proteins" is meant any protein that is differentially induced at the onset of systemic acquired resistance. Defense proteins include chitanses, B-1,3-glucanases, and peroxidases. Differential inducement of the defense proteins can be measured by an increase in the amount of defense proteins produced by the plant. Differential inducement can also be measured by an increase in the specific activity of the defense proteins. The increase in specific activity can be related to the presence of specific isoforms of the defense proteins. Additionally, differential inducement may also include differences in the normal ratios of the proteins relative to each other.

In addition to the production of defense proteins, systemic acquired resistance in the plant being treated is also preferably accompanied by a biphasic release of active oxygen species (AOS). Plants in which SAR has been induced exhibit an oxidative burst (Bargabus, et al., MPMI 16: 1145-1153 (2003), herein incorporated by reference). The oxidative burst is one of the earliest events in plant defense responses (Costet et al 2002). It is marked by the production of AOS through four sequential, one-electron reductions of dioxygen to water (Hippeli et al. 1999). The AOS include, in order of least to most reactive and longest to shortest lived, hydrogen peroxide, superoxide anion, and hydroperoxyl and hydroxyl radicals (Boveris 1998).

AOS are produced in both compatible and incompatible plant-pathogen interactions (Baker and Orlandi 1995; Glazener et al. 1996; Jabs et al. 1997; Wolfe et al. 2000). The production of hydrogen peroxide and superoxide anion also has been observed in *rhizobium*-plant interactions (Santos et al. 2001). In a compatible plant-pathogen interaction, a single, rapid burst of hydrogen peroxide is observed (Grant and Loake 2000). This response is believed to be due to the perception by the host of generic pathogen constituents, such as fungal glucans, chitins. or chitosans (Boller 1995), the conserved N-terminal region of bacterial flagella (Felix et al. 1999), or viral coat proteins (Allan et al. 2001). The transient primary burst is nonspecific and has no effect on disease progression (van Breusegem et al. 2001). During incompatible interactions, a second, more prolonged peak of hydrogen peroxide production quickly follows the initial burst as a result of specific gene-for-gene recognition (Baker and Orlandi 1995; Levein et al. 1994).

The present invention is directed to compositions and methods of inducing systemic resistance to infection, particularly pathogen infection, using a *Bacillus* control agent. By "systemic acquired resistance" (or "SAR") is meant a non-specific defense response of plants triggered following the induction of a hypersensitive response by an invading pathogen. SAR has been observed in both monocotyledenous and dicotyledenous plants and may be triggered by any type of invading pathogen (including bacteria, virus or fungus). The SAR response is non-specific in that it produces enhanced resistance to a broad spectrum of pathogens, regardless of the type of invading pathogen that triggered the response. It generally occurs throughout the plant, regardless of where the pathogen infection occurred. The SAR response usually begins within 2-10 days after the triggering pathogen invasion, and lasts for anywhere from several days to several weeks.

The present invention utilizes compositions comprising *Bacillus* control agents. By "*Bacillus* control agent" or "*Bacillus* biological control agent" herein is meant a *Bacillus* organism that can be used to eliminate or regulate the population of other living organisms, particularly relating to the regulation of pathogens in and on host plants. Preferred *Bacillus* control agents include those agents that induce systemic acquired resistance. In a preferred embodiment, the *Bacillus* control agent is a *Bacillus mycoides* isolate. In a further preferred embodiment, the *Bacillus* control agent is *Bacillus mycoides* isolate BmJ (accession number NRRL B-30890). In another preferred embodiment, the *Bacillus* control agent is a *Bacillus mojavensis* isolate. In a further preferred embodiment, the *Bacillus* control agent is *Bacillus mojavensis* isolate 203-7 (accession number NRRL B-30893). Additional preferred *Bacillus* control agents can be identified as outlined below.

The present invention provides methods of inducing systemic acquired resistance to pathogen infection in a plant. Thus, the methods of the invention are useful in preventing or treating infections which are caused by various microorganisms (e.g. pathogens) including, for example, bacteria, fungi, and viruses. The present invention provides methods of inducing disease resistance to infection in a plant, comprising applying a *Bacillus* control agent comprising *Bacillus mojavensis* isolate 203-7 and/or *Bacillus mycoides* isolate BmJ to the plant, wherein the plant is capable of producing defense proteins. In one embodiment, the disease resistance to infection is systemic acquired resistance. In another embodiment, the systemic acquired resistance in the plant is induced through a salicylic acid independent and jasmonic acid dependent pathway. In another embodiment, the systemic acquire resistance is induced by *Bacillus mycoides* isolate BmJ through a NON-EXPRESSOR OF PATHOGENESIS-RELATED GENES1 (NPR1) dependent pathway. In another embodiment, the systemic acquired resistance is induced by *Bacillus mojavensis* isolate 203-7 through a NPR1 independent pathway.

In one embodiment, the plant is a monocot. For example, the monocot plant is in the gramineae and cereal groups. Non-limiting exemplary monocot species include grains, tropical fruits and flowers, banana, maize, rice, barley, duckweed, gladiolus, sugar cane, pineapples, dates, onions, pineapple, rice, sorghum, turfgrass and wheat. In another embodiment, the plant is a dicot. For example, the dicot plant is selected from the group consisting of Anacardiaceae (e.g., cashews, pistachios), Asteraceae (e.g., asters and all the other composite flowers), Brassicaceae (e.g., cabbage, turnip, and other mustards), Cactaceae (e.g., cacti), Cucurbitaceae (e.g., watermelon, squashes), Euphorbiaceae (e.g., cassava (manioc)), Fabaceae (e.g., beans and all the other legumes), Fagaceae (e.g., oaks), Geraniales (e.g., Geranium), Juglandaceae (e.g., pecans), Linaceae (e.g., flax), Malvaceae (e.g., cotton), Oleaceae (e.g., olives, ashes, lilacs), Rosaceae (e.g., roses, apples, peaches, strawberries, almonds), Rubiaceae (e.g., coffee), Rutaceae (e.g., oranges and other citrus fruits), Solanaceae (e.g., potato, tomato, tobacco), Theaceae (e.g., tea), and Vitaceae (e.g., grapes).

In another embodiment, the infection is caused by any kind of infectious (i.e., biotic) agents that affect plants. Examples of such agents/pathogens include but are not limited to an agent or pathogen selected from the group consisting of bacteria, fungi, and viruses. Examples of specific pathogens to be treated using the compositions and methods of the present invention include but are not limited to pathogens selected from the group consisting of *Mycosphaerella fijiensis* (Black sigatoka), *Cladosporium caryigenum* (pecan scab), *Glomerella cingulata* (Anthracnose), *Cercospora beticola* (Cercospora leaf spot), *Botrytis cinerea, Fusarium solani* f. sp. *cucurbitae* (Fusarium Crown rot), *Pseudomonas syringe* (angular leaf spot), *Erwinia caratovora* (bacterial vascular necrosis), *Alternaria solani* (early blight), *Sclerotinia sclerotiorum* (wild mold disease), *Xanthomonas campestris* (bacterial spot disease), *Botrytis cinerea* (gray mold), *Pythium aphanidermatum* (root rotting disease), *Podosphora xanthii* (Powdery mildew), and plant viruses. In some embodiments, the plant viruses are selected from the group consisting of Potato Virus Y, cucumber mosaic virus, tobacco mosaic virus, and squash vein yellowing virus.

Examples of bacteria that may cause infections treatable or preventable by inducing systemic resistance in a plant include *Pseudomonas* species, particularly *Pseudomonas aeruginosa, Pseudomonas fluorecens*, and *Pseudomonas syringe* (angular leaf spot). Other bacteria that may cause infections treatable or preventable by inducing systemic resistance in a plant include *Erwinia caratovora* (bacterial vascular necrosis), *Pantoua agglomorans, Erwinia tracheiphilia, Xanthomonas axanopodis*, and *Xanthomonas campestris*. Depending on the species of bacteria and the tissue infected they produce and release enzymes that degrade cell walls, growth regulators that alter the plants' normal growth, toxins that degrade cell membranes and/or complex sugars that plug water conducting tissue. A general classification of phytopathogenic prokaryotes can be found below:

```
Kingdom: Procaryotae
    Bacteria - Have cell membrane and cell wall and no nuclear membrane
        Division: Bacteria - Gram-positive
            Class: Proteabacteria - Mostly single celled bacteria.
                Family: Enterobacteriaceae
                    Genus: Erwinia, causing fire blight of
                        pear and apple, Stewart's wilt in corn,
                        and soft rot of fleshy vegetables.
                        Pantoea, causing wilt of corn.
                        Serratia, S. marcescens, a
                        phloem-inhibiting bacterium
                        causing yellow vein disease of
                        cucurbits.
                        Sphingomonas, causing brown
                        spot of yellow Spanish melon
                        fruit.
                Family: Pseudomonadaceae
                    Genus: Acidovorax, causing leaf spots in
                        corn, orchids and watermelon.
                        Pseudomonas, causing
                        numerous leaf spots, blights,
                        vascular wilts, soft rots, cankers,
                        and galls.
                        Ralstonict, causing wilts of
                        solanaceous crops.
                        Rhizobacter, causing the bacterial
                        gall of carrots.
                        Rhizomonas, causing the corky
                        root rot of lettuce.
                        Xanthomonas, causing numerous
                        leaf spots, fruit spots, blights of
                        annual and perennial plants,
                        vascular wilts and citrus canker.
                        Xylophilus, causing the bacterial
                        necrosis and canker of grapevines.
                Family: Rhizobiaceae
                    Genus: Agrobacterium, the cause of
                        crown gall disease.
                        Rhizobium, the cause of nitrogen-
                        fixing root nodules in legumes.
                Family: still unnamed
                    Genus: Xylella, xylem-inhabiting, causing
                        leaf scorch and dieback disease
                        on trees and veins.
                        Candidatus liberobacter, Phloem
                        inhabiting, causing citrus greening
                        disease.
                        Unnamed, laticifer-inhabiting,
                        causing bunchy top disease of
                        papaya.
        Division: Firmicutes - Gram-positive bacteria.
            Class: Firmibacteria - Mostly single celled bacteria.
                    Genus: Bacillus, causing rot of tubers,
                        seeds, and seedlings and white
                        stripe of wheat.
```

| | |
|---|---|
| | *Clostridium*, causing rot of stored tubers and leaves and wetwood of elm and poplar. |
| Class: Thallobacteria - Branching bacteria. | |
| | Genus: *Arthrobacter*, causing bacterial blight of holly, thought to be the cause of Douglas-fir bacterial gall. |
| | *Clavibacter*, causing bacterial wilts in alfalfa, potato, and tomato. |
| | *Curtobacterium*, causing wilt in beans and other plants. |
| | *Leifsonia*, causing ratoon stunting of sugarcane. |
| | *Rhodococcus*, causing fasciation of sweet pea. |
| | *Streptomyces*, causing common potato scab. |

More plant pathogenic bacteria are described in Robert W. Jackson, *Plant Pathogenic Bacteria: Genomics and Molecular Biology*, published by Horizon Scientific Press, 2009, ISBN 1904455379, 9781904455370; Samuel S. Gnanamanickam, *Plant-Associated Bacteria*, published by Springer, 2007, ISBN 1402045379, 9781402045370; Martin Dworkin et al., *The Prokaryotes: a handbook on the biology of bacteria*, Published by Springer, 2006, ISBN 0387254927, 9780387254920; George N. Agrios, *Plant pathology*, published by Academic Press, 2005, ISBN 0120445654, 9780120445653; and David W. Parry, *Plant pathology in agriculture*, published by CUP Archive, 1990, ISBN 0521368901, 9780521368902.

Numerous classes of plant pathogenic fungi, including oomycetes, ascomycetes, and basidiomycetes, may cause infections treatable or preventable by inducing systemic resistance in a plant. Examples of fungi that may cause infections treatable or preventable by inducing systemic resistance in a plant include *Cercospora beticola* (*Cercospora* leaf spot), *Mycosphaerella fijiensis* (Black sigatoka), *Glomerella cingulata* (Anthracnose) and *Cladosporium caryigenum* (pecan scab). In general, fungal plant diseases can be classified into two types: those caused by soilborne fungi and those caused by airborne fungi. Soilborne fungi cause some of the most widespread and serious plant diseases, such as root and stem rot caused by *Fusarium* spp. And root rot caused by *Phytophthora* spp. For example, *Phytophthora parasitica* var. *nicotiana*, a soilborne oomycete found in many tobacco growing regions worldwide, causes black shank, a highly destructive root and stem rot disease of many varieties of cultivated tobacco. Since airborne fungi can be spread long distances by wind, they can cause devastating losses, particularly in crops which are grown over large regions. A number of pathogens have caused widespread epidemics in a variety of crops. Important diseases caused by airborne fungi are stem rust (*Puccinia graminis*) on wheat, corn smut (*Ustilago maydis*) on corn, and late blight disease (*Phytophthora infestans*) on potato and tomato. *Plasmopara viticola* is an airborne oomycete that causes downy mildew disease on grape veins. The blue mold fungus (*Peronospora tabacina*) has caused catastrophic losses in tobacco crops, particularly in the United States and Cuba. Most of these fungal diseases are difficult to combat, and farmers and growers must use a combination of practices, such as sanitary measures, resistant cultivars, and effective fungicide against such diseases. Billions of dollars are spent annually for chemical control of plant-pathogenic fungi. As a result, there is today a real need for new, more effective and safe means to control plant-pathogenic fungi, particularly oomycete, which are responsible for major crop loss. Non-limiting examples of fungal plant pathogens include, *Alternaria solani, Sclerotinia sclerotiorum, Botrytis cinerea, Podosphora xanthii, Cercospora, beticola, Mycosphaerella fijiensis*, and *Cladosporium caryigenum*. More fungal plant pathogens are described in Arya et al. (Management of Fungal Plant Pathogens, CABI, 2010, ISBN 1845936035, 9781845936037), Lane et al. (Fungal Plant Pathogens, Stylus Pub Llc, 2011, ISBN 184593668X, 9781845936686), and Isaac (Fungal-plant interactions, Springer 1992, ISBN 0412353903, 9780412353901), each of which is herein incorporated by reference in its entirety for all purposes.

Oomycetes is a class of Oomycota, which is a phylum of filamentous protists, containing over around 70 genera and more than 800 known species (J. W. Deacon *Modern mycology* Edition: 3, Published by Wiley-Blackwell, 1997 ISBN 0632030771, 9780632030774).

"Oomycota" means "egg fungi", referring to the oversize oogonia which house the female gametes (eggs). Despite the name and their superficial appearance, oomycetes are not fungi. They are unicellular heterokonts, physically resembling fungi. Oomycetes are commonly known as water molds (or water moulds) or downy mildew. They are microscopic, absorptive organisms that reproduce both sexually and asexually and are composed of mycelia, or a tube-like vegetative body (all of an organism's mycelia are called its thallus).

Oomycete cells differ from those of true fungi in that they have walls of cellulose and the amino acid hydroxyproline. They are heterotophic, either saphropytic or parasitic. The principle cell wall of oomycetes is not composed of chitin, as in the fungi, but is made up of a mix of cellulosic compounds and glycan. The nuclei within the filaments are diploid, with two sets of genetic information, not haploid as in the fungi.

Oomycetes do not synthesize sterols. They have cillia (small hairlike structures) that help it eat and move around. Among the oomycetes, these are produced as asexual spores called zoospores, which are released from sporangium and capitalize on surface water (including precipitation on plant surfaces) for movement. Oomycetes may also germinate directly on the host plant by way of a germ tube. They also produce sexual spores, called oospores, that are translucent double-walled spherical structures used to survive adverse environmental conditions. This type of reproduction is known as "gametangical copulation". A few produce aerial asexual spores that are distributed by wind.

The water molds are economically and scientifically important because they are aggressive plant pathogens. Some species can cause disease in fish. The majority can be broken down into three groups, although more exist.

The *Phytophthora* group is a genus that causes diseases such as dieback, late blight in potatoes, sudden oak death, rhododendron root rot, and ink disease in the American Chestnut.

The *Pythium* group is even more prevalent than *Phytophthora* and individual species have larger host ranges, usually causing less damage. *Pythium* damping off is a very common problem in greenhouses where the organism kills newly emerged seedlings. Mycoparasitic members of this group (e.g. *P. oligandrum*) parasitize other oomycetes and fungi, and have been employed as biocontrol agents. One *Pythium* species, *Pythium insidiosum* is also known to infect mammals.

The third group of oomycetes is the downy mildews, which are easily identifiable by the appearance of white "mildew" on leaf surfaces.

Oomycete-caused plant diseases include, but are not limited to, grape downy mildew (caused by *Plasmopara viticola*) and potato late blight (caused by *Phytophthora infestans*) and oomycete infestation of Arctotis (caused by *Bremia lactucae*), *Chenopodium murale* (caused by *Peronospora farinosa*), cucurbits and cucumbers (caused by *Pseudoperonospora cubensis*), grasses and grains (caused by *Sclerospora graminicola*), lettuce (caused by *Bremia lactucae*), onion (caused by *Peronospora destructor*), alfalfa (caused by *Peronospora trifoliorum*), lima bean (caused by *Phytophthora phaseoli*), sunflower (caused by *Plasmopara halstedii*), carrot (caused by *Plasmopara nivea*, also called *Plasmopara crustosa*), hops (caused by *Pseudoperonospora humuli*), crucifers (caused by *Peronospora parasitica*), spinach (caused by *Peronospora effusa*), beet (caused by *Peronospora schachtii*, also called *Peronospora farinosa*), peas (caused by *Peronospora viciae*), rose (caused by *Peronospora sparsa*), poppy (caused by *Peronospora arborescens*), tobacco (caused by *Peronospora hyoscami*), and violet (caused by *Peronospora violae*).

Plant viruses are viruses affecting plants. Examples of viruses that may cause infections treatable or preventable by inducing systemic resistance in a plant include cucumber mosaic, tobacco mosaic, and barley yellow dwarf virus. Plant viruses are obligate intracellular parasites that do not have the molecular machinery to replicate without a host. Over 50% of known plant viruses are rod shaped (flexuous or rigid). The length of the particle is normally dependent on the genome but it is usually between 300-500 nm with a diameter of 15-20 nm. Protein subunits can be placed around the circumference of a circle to form a disc. In the presence of the viral genome, the discs are stacked, then a tube is created with room for the nucleic acid genome in the middle. The second most common structure amongst plant viruses are isometric particles. They are 40-50 nm in diameter. In cases when there is only a single coat protein, the basic structure consists of 60 T subunits, where T is an integer. Some viruses may have 2 coat proteins are the associate to form a icosahedral shaped particle. There are three genera of Geminiviridae that possess geminate particles which are like two isometric particles stuck together. A very small number of plant viruses have, in addition to their coat proteins, a lipid envelope. This is derived from the plant cell membrane as the virus particle buds off from the cell. Non-limiting exemplary plant viruses species are Alfalfa mosaic virus (Alfamovirus), Apple chlorotic leaf spot virus (Trichovirus), Apple scar skin viroid (Viroids), Arabis mosaic virus (Nepovirus), Barley mild mosaic virus (Bymovirus), Barley stripe mosaic virus (Hordeivirus), Barley yellow mosaic virus (Bymovirus), Bean common mosaic virus (Potyvirus), Bean yellow mosaic virus (Potyvirus), Beet necrotic yellow vein virus (Furovirus), Blackeye cowpea mosaic virus (Potyvirus), Bean common mosaic virus (Potyvirus), Broad bean wilt virus (Fabavirus), Butterbur mosaic virus (Carlavirus), Carnation mottle virus (Carmovirus), Carnation vein mottle virus (Potyvirus), Cauliflower mosaic virus (Caulimovirus), Chrysanthemum mild mottle virus (Cucumovirus), Tomato aspermy virus (Cucumovirus), Chrysanthemum stunt viroid (Viroids), Citrus mosaic virus, Citrus tristeza virus (Closterovirus), Clover yellow vein virus (Potyvirus), Cocksfoot mottle virus (Sobemovirus), Cucumber green mottle mosaic virus (Tobamovirus), Cucumber mosaic virus (Cucumovirus), Cycas necrotic stunt virus (Nepovirus), Dasheen mosaic virus (Potyvirus), Grapevine Algerian latent virus (Tombusvirus), Konjac mosaic virus (Potyvirus), Melon necrotic spot virus (Carmovirus), Mulberry ringspot virus (Nepovirus), Narcissus mosaic virus (Potexvirus), Odontoglossum ringspot virus (Tobamovirus), Papaya ringspot virus (Potyvirus), Peach latent mosaic viroid, Peanut mottle virus (Potyvirus), Peanut stripe virus (Potyvirus), Bean common mosaic virus (Potyvirus), Peanut stunt virus (Cucumovirus), Potato virus A (Potyvirus), Potato virus M (Carlavirus), Potato virus S (Carlavirus), Potato virus X (Potexvirus), Potato virus Y (Potyvirus), Prune dwarf virus (Ilarvirus), Prunus necrotic ringspot virus (Ilarvirus), Radish mosaic virus (Comovirus), Rice black streaked dwarf virus (Fijivirus), Rice dwarf virus (Reovirus), Rice grassy stunt virus (Tenuivirus), Rice stripe virus (Tenuivirus), Rice tungro spherical virus (Sequivirus), Rice waika virus, Rice tungro spherical virus (Sequivirus), Ryegrass mottle virus, Satsuma dwarf virus (Nepovirus), Soil-borne wheat mosaic virus (Furovirus), Southern bean mosaic virus (Sobemovirus), Soybean mosaic virus (Potyvirus), Soybean stunt virus (Cucumovirus), Cucumber mosaic virus (Cucumovirus), Tobacco mosaic virus (Tobamovirus), Tobacco mosaic virus (Tobamovirus), Tomato mosaic virus (Tobamovirus), Tobacco necrosis virus (Necrovirus), Tobacco rattle virus (Tobravirus), Tobacco ringspot virus (Nepovirus), Tomato aspermy virus (Cucumovirus), Tomato black ring virus (Nepovirus), Tomato mosaic virus (Tobamovirus), Tomato ringspot virus (Nepovirus), Tomato spotted wilt virus (Tospovirus), Turnip mosaic virus (Potyvirus), Watermelon mosaic virus 1 (Potyvirus), Papaya ringspot virus (Potyvirus), Watermelon mosaic virus 2 (Potyvirus), Wheat yellow mosaic virus (Bymovirus), Zucchini yellow mosaic virus (Potyvirus). More plant viruses have been described in F. C. Bawden, *Plant Viruses and Virus Diseases*, Publisher Biotech Books, 2002, ISBN 8176220647, 9788176220644, which is incorporated herein by its entirety for all purposes.

In one embodiment of the invention, systemic acquired resistance to infection is induced by applying to the foliage of the plant a composition comprising a *Bacillus* control agent.

Methods of Controlling Plant Diseases

In some embodiments, the present *Bacillus* control agent comprises *Bacillus mycoides* isolate BmJ having accession number NRRL B-30890 or spores thereof. The agent can be used to control one or more plant diseases, such as fungal plant diseases, bacterial plant diseases, and/or viral plant diseases. As used herein, the term "control" or "controlling" means to kill plant pathogens; or to reduce the symptoms or damages due to the diseases; or to inhibit the activity of plant pathogens (e.g., reduced mobility, spreading and/or reproductive capability); or to prevent or reduce plant pathogen transmission from a host or area.

In some embodiments, the *Bacillus* control agent is applied to a plant or one or more plant parts by itself, or mixed with another control agent, or rotated with another control agent. The *Bacillus* control agent can be applied anytime during the life cycle of a plant. For example, the control agent can be applied to plants before, during, or after germination, growing, blossoming, fruiting, harvesting, or transplanting. It can also be applied to the soil around the plant.

The *Bacillus* control agent is effective in controlling many plant diseases, including but not limited to, early blight disease (*Alternaria solani*), white mold disease (*Sclerotinia sclerotiorum*), bacterial spot disease (*Xanthomonas campestris*), gray mold (*Botrytis cinerea*), root rotting disease (*Pythium aphanidermatum*), powdery mildew (*Podosphora xanthii*), pecan scab (*Cladosporium caryigenum*), diseases caused by *Cercospora beticola*, or *Pseudomonas* species, and diseases associated with plant viruses, such as Potato Virus Y, cucumber mosaic virus, tobacco mosaic virus, and squash vein yellowing virus.

Early blight caused by *Alternaria solani* is a fungal plant disease. Tomatoes and potatoes are the most common hosts, but it can also attack eggplant, pepper, horse nettle, black nightshade, wild cabbage, cucumber, and zinnia, etc. It affects plants in all plant growth stages and in all the plant parts except the roots.

White mold disease caused by *Sclerotinia sclerotiorum* is a fungal plant disease, a.k.a. *sclerotinia* stem rot. *Sclerotinia sclerotiorum* is a fungus that has a wide host range, including alfalfa, beans, canola, clover, peppermint, potato, sunflower, and tomato. It can also infect several weed hosts, such as amaranths, castor bean, dandelion, lambsquarters, ragweed, and velvetleaf, etc. Because sclerotia survive in the soil, soil movement could also transport inoculum from one field to another. White mold management in the prior art is difficult when environmental conditions are favorable for the disease. The sclerotia can remain in the soil for several years, and lose their viability slowly. The most effective defense against white mold is to keep the fungus out of a field, but this can be difficult.

Potato virus Y (PVY) is a plant pathogenic virus of the family Potyviridae, and one of the most important plant viruses affecting potato production. PVY is transmissible by aphid vectors but may also remain dormant in seed potatoes. PVY belongs to the potyvirus genus, which includes more than 200 members that bring about significant losses in the agricultural arena (Jawaid, A. Khan A. J and Dijkstra J. (2002). Plant Viruses as Molecular Pathogens. Food Products Press, The Haworth Press Inc., N.Y.). PVY infects many economically important plant species. These include, but are not limited to, Solanaceae species, such as potato (*Solanum tuberosum*), tobacco (*Nicotiana tabacum*), tomato (*Solanum lycopersicum*) and pepper (*Capsicum* spp.). There are three main groups of Potato Virus Y strains: $PVY^O$ (ordinary type) occurs in most potato growing countries worldwide; $PVY^C$ in eastern Australia, South America, New Zealand, Europe, South Africa, and North America; and $PVY^N$ in North America, New Zealand, Europe, Africa and South America. $PVY^{NTN}$ is a new type of strain that causes tuber necrosis (reported in Europe, New Zealand, Middle East, North America and Japan).

Bacterial spot caused by *Xanthomonas campestris* is a bacterial plant disease. *Xanthomonas* species is a Gram-negative rod-shaped bacteria known for being a common plant pathogen. *Xanthomonas* affects many types of hosts, including citrus, beans, grapes, cotton, and rice. Typical symptoms of the disease include lesions on the leaves, fruit, and stems. *Xanthomonas campestris* is an aerobic, Gram-negative rod known to cause the black rot in crucifers by darkening the vascular tissues. Over 20 different hosts of *X. campestris* have been identified by its distinctive pathogenicity on a wide range of plants including crops and wild plants. This bacterium is mesophilic with optimal temperature at 25-30 degrees Celsius (77-85 degrees Fahrenheit) and inactive at temperatures below 10 degrees Celsius (50 degrees Fahrenheit) See, Averre, Charles W. "Black Rot of Cabbage and Related Crops" Accessed on Aug. 16, 2007. *X. campestris* cells have Hypersensitive response and pathogenicity (Hrp) pili that help transfer effector proteins to decrease the host's defense and glide through water. They can live in a soil for over a year and spread through any movement of water including rain, irrigation and surface water.

Gray mold disease is caused by fungal pathogen *Botrytis cinerea*. It is found almost everywhere and can cause disease on almost every plant species. The fungus overwinters in the soil and in plant debris; it becomes active under cool moist conditions. Prevention includes adequate air circulation, good sanitation, and avoiding overcrowding and overhead watering late in the day. It is favored by high (93-100%) relative humidity and low (45° to 60° F.) temperatures. *Botrytis* infects immature, dying or damaged foliage, flower parts, young stems, and occasionally roots. Since *Botrytis* will grow on almost any decaying plant material, its host range includes almost all plants.

Root rotting pathogen *Pythium aphanidermatum* is a cosmopolitan pathogen with a wide host range. It is an aggressive species of *Pythium*, causing damping off, root and stem rots, and blights of grasses and fruit. It is of economic concern on most annuals, cucurbits, and grasses. It is considered one of the water molds because it survives and grows best in wet soils. Warm temperatures favor the pathogen, making it an issue in most greenhouses. *Pythium aphanidermatum* occurs world wide, particularly in warm regions and greenhouses. The fungus prefers temperatures between 27 and 34° C. and wet conditions (water potential of 0 to −0.01 bars). It has a very wide host range, including many annuals and bedding plants. It causes economic losses on ornamental plants, such as beets, pepper, chrysanthemum, cucurbits, cotton, and grasses, etc. Ornamental plants are plants that are grown for decorative purposes in gardens and landscape design projects, as house plants, for cut flowers and specimen display. The cultivation of these forms a major branch of horticulture. Most commonly ornamental garden plants are grown for the display of aesthetic features including: flowers, leaves, scent, overall foliage texture, fruit, stem and bark, and aesthetic form. In some cases, unusual features may be considered of interest, such as the prominent and rather vicious thorns of *Rosa sericea* and *cacti*. In all cases, their purpose is for the enjoyment of gardeners, visitors, and/or the public. *Pythium* survives in the soil as oospores, hyphae and sporangia. The fungus can survive unfavorable soil moisture and temperatures for several years as oospores. Oospores may form a germ tube directly to infect the plant or they may form sporangia. The sporangia produce zoospores, which are the motile form of the fungus. The zoospores swim around briefly before encysting and forming a germ tube, which can cause infection. Sporangia that have developed on plant tissue can germinate in a similar manner as the oospores, by either germinating directly or by forming zoospores. The pathogen is dispersed when infected debris is transported to uninfested areas and when the soil moisture is enough to allow the zoospores to swim freely. *Pythium aphanidermatum* infects seeds, juvenile tissue, lower stems, fruit rot and roots. The symptoms and extent of damage caused depend on the region infected. The pathogen is associated with disease symptoms such as damping off, stem rot, root rot, pythium blight, cottony blight, etc.

Powdery mildew diseases are caused by many different species of fungi in the order Erysiphales. The lower leaves are the most affected, but the mildew can appear on any above-ground part of the plant. As the disease progresses, the spots get larger and denser as large numbers of asexual spores are formed, and the mildew may spread up and down the length of the plant. Non-limiting examples of Powdery mildew include, powdery mildew caused by *Erysiphe necator* (or *Uncinula necator*), e.g., in grape; powdery mildew caused by *Blumeria graminis forma specialis* (f. sp.) *tritici*, e.g., in wheat; powdery mildew caused by *Leveillula taurica* (also known by its anamorph name, *Oidiopsis taurica*), e.g., in onions and artichoke; powdery mildew caused by *Podosphora leucotricha*, e.g., in apples, and pear; powdery mildew caused by *Podosphaera fusca*, e.g., in Curcurbits: cucumbers, squashes (including pumpkins), luffas, melons and watermelons; powdery mildew caused by *Microsphaera syringae*, e.g., in lilacs; powdery mildew caused by *Podosphaera aphanis*, e.g., in strawberry and other Rosaceae; powdery mildew caused by *Sawadaea tulasnei*; and powdery mildew caused by *Podosphora xanthii* (also as *Podosphaera xanthii*, or *Sphaerotheca fuliginea* Schlech ex Fr. Poll.), e.g., in Curcurbits.

The host range of *Podosphaera* xanthii includes several families of angiosperm species, such as Asteracea, Cucurbitaceae, Lamiaceae, Scrophulariaceae, Solanaceae and Verbenaceae (Perez-Garcia et al., *Mol Plant Pathol.* 2009 March; 10(2):153-60.). Other scientific names for *Podosphaera xanthii* include, *Oidium citrulli* J. M. Yen & Chin C. Wang, *Sphaerotheca xanthii* (Castagne) L. Junell, *Erysiphe fuscata* Berk. & M. A. Curtis, *Erysiphe xanthii* Castagne, *Spaerotheca fuscata* (Berk. & M. A. Curtis) Serbinov, *Sphaerotheca microcarpa* Haszl., *Sphaerotheca calendulae* (Malbr. & Roum.) Malbr., *Sphaerotheca verbenae* Savul. & Negru *Sphaerotheca indica* Patw., *Sphaerotheca cucurbitae* (Jacz.) Z. Y. Zhao, *Sphaerotheca phaseoli* (Z. Y. Zhao) U. Braun, *Podosphaera phaseoli* (Z. Y. Zhao) U. Braun & S. Takam., *Sphaerotheca fuliginea* auct. p.p., *Oidium erysiphoides* auct. p.p., *Erysiphe fuliginea* auct. p.p., *Sphaerotheca castagnei* auct. p.p., *Sphaerotheca humuli* var. *fuliginea* auct. p.p.

Downey mildew caused by *Pseudoperonospora cubensis* is a fungal plant disease. The host range of *Pseudoperonospora cubensis* includes cucurbits, such as cantaloupe, cucumber, pumpkin, squash and watermelon. *P. cubensis* is an obligate parasite or biotroph, meaning that it requires live host tissue in order to survive and reproduce. Because of this characteristic, the pathogen must overwinter in an area that does not experience a hard frost, such as southern Florida, and where wild or cultivated cucurbits are present. The spores are dispersed via wind to neighboring plants and fields and often over long distances. Symptoms appear 4 to 12 days after infection. The pathogen thrives under cool and moist conditions, but can do well under a wide range of conditions. Optimum conditions for sporulation are 59° F. (15° C.) with 6 to 12 hours of moisture present, often in the form of morning dew. Even when high daytime temperatures are not favorable for the pathogen (>95° F. or >35° C.), nighttime temperatures may be very suitable.

Tobacco mosaic virus (TMV) is a positive-sense single stranded RNA virus that infects plants, especially tobacco and other members of the family Solanaceae. TMV does not have a distinct over-wintering structure. Rather, it will overwinter in infected tobacco stalks and leaves in the soil or on the surface of contaminated seed (TMV can even survive in contaminated tobacco products for many years). With direct contact to host plants through its vectors (normally insects such as aphids and leaf hoppers), TMV will go through the infection process and then the replication process. It is known to infect members of nine plant families, and at least 125 individual species, including tobacco, tomato, pepper (all members of the useful Solanaceae), cucumbers, a number of ornamental flowers, petunia, snapdragon, delphinium, marigold, muskmelon, cucumber, squash, spinach, celosia, impatiens, ground cherry, phlox, zinnia, certain types of ivy, plantain, night shade, and jimson weed.

Cucumber mosaic virus (CMV) is a plant pathogenic virus in the family Bromoviridae. It is the type member of the plant virus genus, Cucumovirus. This virus has a worldwide distribution and a very wide host range, such as squash, melons, peppers, beans, tomatoes, carrots, celery, lettuce, spinach and beets, various weeds and many ornamentals and bedding plants. CMV is mainly transmitted by aphids. It can also be spread mechanically by humans.

Squash vein yellowing virus is the cause of watermelon vein decline (WVD) disease (Baker et al., Plant Pathology Circular No. 407 Fla. Dept. of Agric. & Consumer Services, June/July 2008). The host range, whitefly transmission, and deduced coat protein (CP) sequence of SqVYV are consistent with it being a novel member of the genus Ipomovirus in the family Potyviridae. SqVYV was transmitted by whiteflies (*Bemisia tabaci*, biotype B). The host range is likely limited to species in the Cucurbitaceae.

Wheat streak mosaic virus is a member of the Potyviridae family of viruses. It occurs in most leaf cells as flexuous rods. The wheat curl mite, *Aceria tosichella*, vectors the virus in the field. It is also easily transmissible through sap by mechanical inoculation. The wheat curl mite vector feeds on young lush growth of wheat and certain grasses. Mites develop from eggs to adults within 8 to 10 days, and their numbers can increase markedly during relatively short periods when the environment is favorable. The most important host is volunteer wheat that emerges before harvest, often because of hailstorms. The mites move from the hailed wheat as it matures to the young volunteer wheat in early July. Reproduction of mites and replication of the virus are favored by temperatures of 75° to 80° F. Rain during summer promotes growth of volunteer plants. In the fall mites move from the volunteer plants to the newly emerged fall-planted winter wheat seedlings. The wingless curl mite depends on wind for its dispersal. Both the mites and WSMV persist on living, susceptible plants, but not on wheat or other grasses as they mature and dry down. Growing wheat is the favorite habitat for the wheat curl mites. Certain other small grains, such as oats, barley, and rye can be attacked by both WSMV and the mites, but they do not show obvious symptoms or significant damage. Wheat, Proso millet, corn, Jointed goatgrass, Japanese chess, Cheat, Downy chess, Sandbur, Smooth crabgrass, Crabgrass, Barnyard grass, and Green foxtail are susceptible to this virus.

The *Bacillus* control agent is applied to a plant or a plant part at an effective amount to control one or more plant pathogens. As used herein, an effective amount of an active ingredient is an amount effective to control plant pathogens and/or to reduce plant damage caused by a plant pathogen. In some embodiments, an effective amount is an amount effective to kill and/or to inhibit plant pathogen growth by about 5%, about 10%, about 20%, about 30%, about 40%, about 50%, about 60%, about 70%, about 75%, about 80%, about 85%, about 90%, or more compared to a host or area not treated with the active ingredient. In some other cases, an effective amount of an active ingredient is an amount effective to reduce the percent of infected plants in a plant population by at least 5%, at least 10%, at least 15%, at least 20%, at least 25%, at least 30%, at least 40%, at least 50%, at least 60%, at least 70%, at least 80%, at least 90%, or more compared to a population not treated with the active ingredient. Still in some other cases, an effective amount of an active ingredient is an amount effective to reduce the percent of plants showing diseases symptom in a plant population by at least 5%, at least 10%, at least 15%, at least 20%, at least 25%, at least 30%, at least 40%, at least 50%, at least 60%, at least 70%, at least 80%, at least 90%, or more compared to a population not treated with the active ingredient. In some other cases, an effective amount of an active ingredient is an amount effective to reduce average disease symptom severity rating or damage rating of a plant population by at least 5%, at least 10%, at least 15%, at least 20%, at least 25%, at least 30%, at least 40%, at least 50%, at least 60%, at least 70%, at least 80%, at least 90%, or more compared to a population not treated with the active ingredient. In some other cases, an effective amount of an active ingredient is an amount effective to increase yield of a plant population by at least 5%, at least 10%, at least 15%, at least 20%, at least 25%, at least 30%, at least 40%, at least 50%, at least 60%, at least 70%, at least 80%, at least 90%, or more compared to a population not treated with the active ingredient. In some other cases, an effective amount of an active ingredient is an amount effective to reduce average pathogen population in a plant population by at least 5%, at least 10%, at least 15%, at least 20%, at least 25%, at least 30%, at least 40%, at least 50%, at least 60%, at least 70%, at least 80%, at least 90%, or more compared to a plant population not treated with the active ingredient. In some embodiments, the *Bacillus* control agent can be applied to a plant at $10^3$-$10^{12}$ cfu ("colony forming units")/ml, e.g., $10^4$-$10^{10}$ cfu/ml, $10^5$-$10^9$ cfu/ml, or $10^7$ cfu/ml.

The present application provides methods using the control agents of the present application to control plant diseases not or not only by directly controlling the pathogens, but by or additionally by affecting a pathogen transmission mechanism, for example, by using the agents of the present invention as a repellent. As used herein, repellent refers to a substance applied to plant which discourages one or more pathogen transmitters (a.k.a. "vectors", e.g., insects, mites) from contacting a plant, such as landing, climbing, feeding, or continuous feeding on that plant. In some embodiments, the methods comprise applying the *Bacillus* control agents of the present invention to a plant or a plant part before or after the emergence or appearance of a pathogen transmitter. For example, the *Bacillus* control agents can be used to prevent or reduce virus infection, such as potato virus Y or wheat streak mosaic virus. A pathogen transmitter of potato virus Y can be an aphid, such as a green peach aphid. A pathogen transmitter of wheat streak mosaic virus can be a mite, such as a wheat curl mite. The *Bacillus* control agents of the present invention can comprise dead or alive cells or spores of *Bacillus mycoides* isolate BmJ having accession number NRRL B-30890. In some embodiments, the agents of the present invention can repel a pathogen transmitter from contacting or feeding on the plants for at least 0.5 day, at least 1 day, at least 2 days, at least 3 days, at least 4 days, at least 5 days, at least 6 days, at least 1 week, or more after application.

The present application also provides methods of controlling one or more soil-borne root pathogens by foliar application of the *Bacillus* control agents of the present invention. In some cfu embodiments, the *Bacillus* control agent can be applied to a plant at $10^3$-$10^{12}$ cfu ("colony forming units")/ml, e.g., $10^4$-$10^{10}$ cfu/ml, $10^5$-$10^9$ cfu/ml, or $10^7$ cfu/ml. In some embodiments, the pathogen is *Pythium aphanidermatum*. Other non-limiting examples of soil-borne root pathogens are described by Campbell and Noe (The Spatial Analysis of Soilborne Pathogens and Root Diseases, Annual Review of Phytopathology Vol. 23: 129-148, 1985), Toussoun (Root diseases and soil-borne pathogens, University of California Press, 1970, ISBN 0520015827, 9780520015821), each of which is herein incorporated by reference in its entirety for all purposes. The *Bacillus* control agents can be applied to a plant at any stage of its life cycle, for example, before, during or after transplanting.

Methods of Applying the *Bacillus* Control Agents

The *Bacillus* control agent is applied to the foliage of the plant by methods known in the art. For example, the *Bacillus* control agent may be applied aerially. In this method, the *Bacillus* control agent is sprayed from above the plants, for example from an airplane. The concentration of the *Bacillus* control agent applied aerially is $10^3$-$10^{12}$ cfu ("colony forming units")/ml, for example, about $10^4$-$10^{10}$ cfu/ml, about $10^5$-$10^9$ cfu/ml, or about $10^7$-$10^8$ cfu/ml. The *Bacillus* control agent can be applied at a wide range of volume/acre of plants treated. For example, the *Bacillus* control agent may be applied at 1-100 gallons/acre, for example, 2-50 gallons/acre, 5-10 gallons/acre, 6-8 gallons/acre, or 5 gallons/acre.

The *Bacillus* control agent can also be applied from the ground, for example by any agricultural spray equipment, such as, for example, an orchard spray mechanism. An orchard spray mechanism is any sprayer, either manual or automatic, that can be used to apply the *Bacillus* control agent to the foliage of a plant. The concentration of the *Bacillus* control agent applied from the ground is $10^3$-$10^{12}$ cfu/ml, for example, about $10^4$-$10^{10}$ cfu/ml, about $10^5$-$10^9$ cfu/ml, or about $10^7$ cfu/ml. The *Bacillus* control agent can be applied from the ground at a wide range of volume/acre of plants treated. For example, the *Bacillus* control agent may be applied at 10-500 gallons/acre, for example, about 10-100 gallons/acre, or 20 gallons/acre.

In one embodiment, the *Bacillus* control agent is applied to the plants as a spray-dried formulation suspended in an aqueous solution. In another embodiment, the *Bacillus* control agent is applied as freshly grown cells. In another preferred embodiment the *Bacillus* control agent is formulated with a carrier to aid dilution and dispersion, wherein such a carrier could include various types of clay, such as attaclay.

In a preferred embodiment, after the *Bacillus* control agent has been applied to the plant, particularly to the foliage of the plant, it proceeds to colonize the plant; particularly the plant phyllosphere.

In a further preferred embodiment of the invention, the *Bacillus* control agents of the invention do not induce necrotic cell death as a result of inducing systemic acquired resistance. By "cell necrosis" or "necrotic cell death" or grammatical equivalents herein is meant cell death that occurs at the site of application (e.g. the foliage) of an agent that causes such necrosis. Plants are examined for necrosis by observation of leaves by microscope, and by staining techniques that selectively stain for dead cells. One of the problems associated with known agents that induce systemic resistance is necrotic cell death that occurs at the site of application of the agents. Unlike these agents, the application of the *Bacillus* control agent does not cause necrotic cell death.

The present invention also provides methods of inducing disease resistance to infection in a plant further comprising applying a second biological or chemical control agent. In one embodiment, the second biological or chemical control agent is antibacterial. In another embodiment, the second biological or chemical control agent is antifungal. In another embodiment, the second biological or chemical control agent is antiviral. In another embodiment, the second biological or chemical control agent is a plant activating agent. In another embodiment, the second biological or chemical control agent is a pesticide. Commonly used bactericides, fungicides, virucides, plant activating agents and pesticides are described below.

Non limiting exemplary bactericides include, active chlorine (i.e., hypochlorites, chloramines, dichloroisocyanurate and trichloroisocyanurate, wet chlorine, chlorine dioxide etc.), active oxygen (peroxides, such as peracetic acid, potassium persulfate, sodium perborate, sodium percarbonate and urea perhydrate), iodine (iodpovidone (povidone-iodine, Betadine), Lugol's solution, iodine tincture, iodinated non-ionic surfactants), concentrated alcohols (mainly ethanol, 1-propanol, called also n-propanol and 2-propanol, called isopropanol and mixtures thereof; further, 2-phenoxyethanol and 1- and 2-phenoxypropanols are used), phenolic substances (such as phenol (also called "carbolic acid"), cresols (called "Lysole" in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants, such as some quaternary ammonium cations (such as benzalkonium chloride, cetyl trimethylammonium bromide or chloride, didecyldimethylammonium chloride, cetylpyridinium chloride, benzethonium chloride) and others, non-quaternary compounds, such as chlorhexidine, glucoprotamine, octenidine dihydrochloride etc.), strong oxidizers, such as ozone and permanganate solutions; heavy metals and their salts, such as colloidal silver, silver nitrate, mercury chloride, phenylmercury salts, copper sulfate, copper oxide-chloride, antibiotics (e.g., Amikacin, Gentamicin, Kanamycin, Neomycin, Netilmicin, Tobramycin, Paromomycin, Geldanamycin, Herbimycin, Loracarbef, Ertapenem, Doripenem, Imipenem/Cilastatin, Meropenem, Cefprozil, Cefuroxime, Cefixime, Cephalosporins, Teicoplanin, Vancomycin, Telavancin, Lincosamides, Daptomycin, Azithromycin, Clarithromycin, Dirithromycin, Erythromycin, Roxithromycin, Troleandomycin, Telithromycin, Spectinomycin, Penicillins, Quinolones, Tetracyclines, Clofazimine, Dapsone, Capreomycin, Cycloserine, Ethambutol, Ethionamide, Isoniazid, Pyrazinamide, Rifampicin, Rifabutin, Rifapentine, Streptomycin) and bacteriophages, etc.

Commonly used fungicides include, but are not limited to, benomyl, TPTH, propiconazole, tetraconazole, benimidazoles, triazoles, strobilurins, carboxamides, sulfananilides, phenylsulfamides, azoles, nitrogenous heterocycles, dicarboximides, phthalimides, carbamates, thiocarbamates, formaidines, antibiotics, aromatics, guanidines, organochlorine compounds, organometallics, organophosphorus compounds, nitrophenyl compounds, sulfur heterocyclyl compounds, ureas, inorganics, and others (e.g., benzamacril, carvone, essential oil extract from plants, cedar leaf oil, neem oil, chloropicrin, DBCP, drazoxolon, fenaminosulf, metzoxolon, oxolinic acid, spiroxamine, cymoxanil, metrafenone. Prohexadione calcium, thicyofen, dithane, chlorothalnil, dichlorophen, dicloran, nitrothal-isopropyl, bronopol, diphenylamine, mildiomycin, oxin-copper, cyflufenamide (e.g., N-(cyclopropylmethoxyimino-(6-difluoromethoxy-2,3-difluorophenyl)-methyl)-2-phenylaceta-mide), UK-2A (antibiotic isolated from Streptomyces sp. 517-02), HEADLINE® (strobilurins), MANEX® (Manganese ethylenebisdithiocarbamate), MANZATE® (Mancozeb), SONATA® (*Bacillus pumilus*), DITHANE® (Mancozeb), ENDURA® (boscalid), QUADRIS®/AMISTAR® (azoxystrobin), CABRIO® (pyraclostrobin), TANOS® (famoxate+curzate), PRESIDIO® (fluopicolide), REVUS® (mandipropamid), FORUM® (dimethomorph), MANEB®/MANCOZEB® (Manganese ethylenebisdithiocarbamate), RIDOMIL GOLD® SC (mefenoxam), RIDOMIL GOLD® Copper (mefenoxam+Cu hydroxide), TERRACLOR® (PCNB), PREVICUR FLEX® (propamocarb), BRAVO® (chlorothalonil), ECHO® (chlorothalonil), fixed copper, ACTIGARD® (acibenzolar-S-methyl), and Streptomycin sulfate, etc.

Plant activating agents are natural or synthetic substances that can stimulate, maintain, or enhance plant resistance to biotic and/or abiotic stressors/pressures, which include, but are not limited to, acibenzolar, probenazole, isotianil, salicyclic acid, azelaic acid, hymexazol, brassinolide, forchlorfenuron, benzothiadiazole (e.g., ACTIGARD® (Acibenzolar-S-Methyl) 50WG), microbes or elicitors derived from microbes, More plant activating agents are described in U.S. Pat. Nos. 6,849,576, 5,950,361, 6,884,759, 5,554,576, 6,100,092, 6,207,882, 6,355,860, 5,241,296, 6,369,296, 5,527,783, and 6,987,130. Microbes, or chemical compounds and peptides/proteins (e.g., elicitors) derived from microbes, can also be used as plant activating agents. Non-limiting exemplary elicitors are: branched-β-glucans, chitin oligomers, pectolytic enzymes, elicitor activity independent from enzyme activity (e.g. endoxylanase, elicitins, PaNie), avr gene products (e.g. AVR4, AVR9), viral proteins (e.g. vial coat protein, Harpins), flagellin, protein or peptide toxin (e.g. victorin), glycoproteins, glycopeptide fragments of invertase, syringolids, Nod factors (lipochitooligo-saccharides), FACs (fatty acid amino acid conjugates), ergosterol, bacterial toxins (e.g. coronatine), and sphinganine analogue mycotoxins (e.g. fumonisin B 1). More elicitors are described in Howe et al., *Plant Immunity to Insect Herbivores, Annual Review of Plant Biology*, 2008, vol. 59, pp. 41-66; Stergiopoulos, *Fungal Effector Proteins* Annual Review of Phytopathology, 2009, vol. 47, pp. 233-263; and Bent et al., *Elicitors, Effectors, and R Genes: The New Paragigm and a Lifetime Supply of Questions*, Annual Review of Plant Biology, 2007, vol. 45, pp. 399-436.

Thus, it is another aspect of this invention to apply a biological or chemical control agent in addition to the *Bacillus* control agent applied to induce systemic acquired resistance to infection in a plant. There are a number of control agents that can be combined with the agents of the invention, including biological and chemical control agents.

Biological control agents are living organisms which can be used to eliminate or regulate the population of other living organisms. Biological control agents can be, for example, antibacterial agents, antifungal agents, antiviral agents, and insecticides. Examples of biological control agents include, but are not limited to, *Bacillus mycoides, Bacillus pumulis, Bacillus thuringiensis* (Bt), *Bacillus liquefacians*, numerous species of *Pseudomonas* bacteria, *Seratia marcesans*, and *Pantoua agglomerans*. Biological control agents include those agents that induce systemic acquired resistance, although this is not required in the combination treatments outlined herein.

Chemical control agents are chemical substances which can be used to eliminate or regulate the population of living organisms. Chemical control agents can be, for example, antibacterial agents, antifungal agents, antiviral agents, and insecticides. Examples of chemical control agents include, but are not limited to, triphenyltin hydroxide (TPTH, Super-Tin, Griffin LLC), propiconazole (Tilt, Syngenta Crop Protection, Inc) and tetraconazole (Eminent, Sipeam Agro USA Inc.), benomyl, Strobilurin fungicides including Azoxystrobilurin (Syngenta), Trifloxstrobilurin (Bayer), Pyracstrobilurin (BASF) and Chlorthalonil fungicides. Chemical control agents may be applied as outlined herein to the foliage in combination with or alternating with the *Bacillus* control agent. Combinations with the *Bacillus* control agent and the chemical fungicide used at ¼ of the recommended label rate have provided disease control equivalent to the chemical fungicide used at the full rate. Chemical control agents include those agents that induce systemic acquired resistance, although this is not required in the combination treatments outlined herein.

In one embodiment of the invention, the *Bacillus* control agent is applied in conjunction with the application of the biological or chemical control agent. In this embodiment, the *Bacillus* control agent is mixed with the biological or chemical agent and applied simultaneously to the plant. Alternatively, the *Bacillus* control agent and biological or chemical control agent are applied separately but simultaneously to the plant. Additionally, the *Bacillus* control agent may be applied after the biological or chemical control agent has been applied to the plant but during the time the biological or chemical control agent is still acting as a biocontrol agent. The biological or chemical control agent may also be applied after the application of the *Bacillus* control agent plant but during the time the *Bacillus* control agent is still acting to induce systemic acquired resistance in the plant.

In further embodiments, the *Bacillus* control agent is applied sequentially with the biological or chemical control agent. In one of these embodiments, the *Bacillus* control agent is applied to the plant and induces systemic acquired resistance before the application of the biological or chemical control agent. The systemic acquired resistance induced by the *Bacillus* control agent mayor may not be present when the biological or chemical control agent is applied. Alternatively, the biological or chemical control agent is applied to the plant before the *Bacillus* control agent. The biological or chemical control agent mayor may not still be acting as a biocontrol agent when the *Bacillus* control agent is applied. This sequential application may be repeated.

According to one embodiment, when the biological or chemical control agent is an antibacterial agent it is preferable that the antibacterial agent is applied prior to the application of the *Bacillus* control agent such that the *Bacillus* control agent is not effected by the antibacterial agent.

In one embodiment, the *Bacillus* control agent is harvested from the plant it has colonized and is then used to induce systemic resistance in plants, a process referred to as host passage. *Bacillus* control agents that have undergone host passage have been shown to be more effective in inducing systemic resistance than those same agents prior to host passage. This may be done reiteratively as well.

It is another aspect of the invention to provide a plant to which a *Bacillus* control agent has been applied. A plant to which a *Bacillus* control agent has been applied is also referred to as a plant "treated" with a *Bacillus* control agent. In a preferred embodiment, the *Bacillus* control agent is applied to the foliage of the plant. In a further preferred embodiment, the phyllosphere of the plant is colonized by the *Bacillus* control agent. In a further preferred embodiment the plant treated with a *Bacillus* control agent is a banana, a curcubit, a pecan, a sugar beet, a potato, or a geranium.

In one embodiment of this aspect of the invention provides for a banana plant treated with a *Bacillus* control agent. In another embodiment, the banana plant is treated with *Bacillus mycoides*. In a further embodiment, the banana plant is treated with *Bacillus mycoides* isolate BmJ (accession number NRRL B-30890). In another embodiment, the banana plant is treated with *Bacillus mojavensis*. In yet a further embodiment, the banana plant is treated with *Bacillus mojavensis* isolate 203-7 (accession number NRRL B-30893). In each of these embodiments, the phyllosphere of the banana plant can be colonized by the *Bacillus* control agent.

In another embodiment of this aspect of the invention provides for a cucurbit plant treated with a *Bacillus* control agent. In one embodiment, the cucurbit plant is treated with *Bacillus mycoides*. In a further embodiment, the cucurbit plant is treated with *Bacillus mycoides* isolate BmJ (accession number NRRL B-30890). In another embodiment, the cucurbit plant is treated with *Bacillus mojavensis*. In yet a further embodiment, the cucurbit plant is treated with *Bacillus mojavensis* isolate 203-7 (accession number NRRL B-30893). In each of these embodiments, the phyllosphere of the cucurbit plant can be colonized by the *Bacillus* control agent.

Another embodiment of this aspect of the invention provides for a pecan plant treated with a *Bacillus* control agent. In one embodiment, the pecan plant is treated with *Bacillus mycoides*. In a further embodiment, the pecan plant is treated with *Bacillus mycoides* isolate BmJ (accession number NRRL B-30890). In another embodiment, the pecan plant is treated with *Bacillus mojavensis*. In yet a further embodiment, the pecan plant is treated with *Bacillus mojavensis* isolate 203-7 (accession number NRRL B-30893). In each of these embodiments, the phyllosphere of the pecan plant can be colonized by the *Bacillus* control agent.

Another embodiment of this aspect of the invention provides for a geranium plant treated with a *Bacillus* control agent. In one embodiment, the geranium plant is treated with *Bacillus mycoides*. In a further embodiment, the geranium plant is treated with *Bacillus mycoides* isolate BmJ (accession number NRRL B-30890). In another embodiment, the geranium plant is treated with *Bacillus mojavensis*. In yet a further embodiment, the geranium plant is treated with *Bacillus mojavensis* isolate 203-7 (accession number NRRL B-30893). In each of these embodiments, the phyllosphere of the geranium plant can be colonized by the *Bacillus* control agent.

Another embodiment of this aspect of the invention provides for a strawberry or a grape plant treated with a *Bacillus* control agent. In one embodiment, the strawberry or the grape plant is treated with *Bacillus mycoides*. In a further embodiment, the strawberry or the grape plant is treated with *Bacillus mycoides* isolate BmJ (accession number NRRL B-30890). In another embodiment, the strawberry or the grape plant is treated with *Bacillus mojavensis*. In yet a further embodiment, the strawberry or the grape plant is treated with *Bacillus mojavensis* isolate 203-7 (accession number NRRL B-30893). In each of these embodiments, the phyllosphere of the strawberry or the grape plant can be colonized by the *Bacillus* control agent.

Another embodiment of this aspect of the invention provides for a wheat plant treated with a *Bacillus* control agent. In one embodiment, the wheat plant is treated with *Bacillus mycoides*. In a further embodiment, the wheat plant is treated with *Bacillus mycoides* isolate BmJ (accession number NRRL B-30890). In another embodiment, the wheat plant is treated with *Bacillus mojavensis*. In yet a further embodiment, the strawberry or the grape plant is treated with *Bacillus mojavensis* isolate 203-7 (accession number NRRL B-30893). In each of these embodiments, the phyllosphere of the wheat plant can be colonized by the *Bacillus* control agent.

Embodiments of the invention include plants treated with the *Bacillus* control agent as well as parts of the plants so treated. For example, a banana leaf or disc from a banana leaf treated with a *Bacillus* control agent is contemplated in this embodiment. Similarly, a plant protoplast, plant spore or plant shoot or plant cell culture treated with a *Bacillus* control agent is contemplated in this embodiment.

Another aspect of the invention provides for methods of screening for biological control agents that induce systemic resistance to a disease in a plant. Currently used means of demonstrating induction of SAR in plants include challenge assays in which distal untreated leaves are challenged with a pathogen following a short priming period with an inducing agent on a primarily, spatially separated leaf or root system (Conrath, et al 2000, herein, incorporated by reference). Challenge assays, however, are time-consuming and difficult to adapt to screening of multiple agents.

One embodiment of the invention provides for a method of screening for a biological control agent that induces systemic resistance in a plant comprising contacting a plant sample with a biological control agent and detecting the release of active oxygen species (AOS) in the sample. Biphasic production of AOS precedes induction of systemic resistance (Wolfe, et al. 2000) and therefore hydrogen peroxide production patterns serve as an indicator of SAR induction capability. In a preferred embodiment, the release of AOS is detected by a phenol red oxidation assay.

Another embodiment of the invention provides for a method of screening for a biological control agent that induces systemic resistance in a plant comprising contacting a plant sample with a biological control agent and detecting for the presence of defense proteins, including, but not limited to, chitinase, B-1,3-glucanase, and peroxidase.

One embodiment provides for a method of screening for a biological control agent that induces systemic resistance in a plant comprising contacting a plant sample with a biological control agent and detecting for the presence of chitinase in the sample. While certain chitinases are present in plants that have not been induced for systemic acquired resistance, overall levels of chitinase activity are increased in plants that have been treated to induce SAR. Additionally, certain isoforms of chitinase have increased specific activity in plants treated to induce SAR.

The presence of chitinase can be determined by monitoring the degradation of chitin by various methods. In one embodiment, the chitinase activity is determined by a glycol chitin plate assay. Glycol chitin plate assays can be performed by first extracting protein from the plant treated with the *Bacillus* control agent and then incubating the extract on an agarose plate containing glycol chitin infused with a fluorescent brightener. The presence of non-fluorescent lytic zones are indicative of chitinase activity. Specific activity of the chitinase can be determined by including a series of standards (Bargabus, R. L., et al., Physiol. Mol. Plant. Pathol. 61:289-298, 2002), herein incorporated by reference). The presence of chitinase can also be determined by monitoring a decrease in fluorescence against time of a solution containing chitin and a fluorescence brightener, such as Calcofluor White M2R, to which a protein extract to be tested for chitinase activity has been added (Sampson M. N., et al, Microbiology, 144:2189-2194 (1998), herein incorporated by reference). Additional methods of measuring chitinase activity include monitoring of degradation of fluorogenic chitinase substrates or radio-labeled chitin substrates (Sampson M. N., et al, Microbiology, 144:2189-2194 (1998)). The presence of chitinase may also be detected using immunoassays. Any of the assays that monitor a detectable signal, such as fluorescence, may be performed in microtiter plates and are amenable to use in high throughput screening.

A further embodiment provides for a method of screening for a biological control agent that induces systemic resistance in a plant comprising contacting a plant sample with a biological control agent and detecting for the presence of B-1,3-glucanase in the sample. While certain B-1,3-glucanase are present in plants that have not been induced for systemic acquired resistance, overall levels of B-1,3-glucanase activity are increased in plants that have been treated to induce SAR. Additionally, certain isoforms of B-1,3-glucanase have increased specific activity plants treated to induce SAR.

The presence of B-1,3-glucanase can be determined by monitoring the degradation of beta-glucan polysaccharide by various methods. In a preferred embodiment, the B 1,3-glucanase activity is determined by an aniline blue plate assay. Aniline blue plate assays can be performed by first extracting protein from the plant treated with the *Bacillus* control agent and then incubating the extract on an agarose plate containing analine blue and laminarin. The presence of pink lytic zones on a blue background are indicative of B-1,3-glucanase activity. Specific activity of the B 1,3-glucanase can be determined by including a series of standards (Bargabus, R. L., et al., Biological Control, In Press, herein incorporated by reference). Additional methods of measuring B 1,3-glucanase activity include monitoring of degradation of fluorogenic B 1,3-glucanase substrates (such as dansyl-labeled laminarin) or radio-labeled B-1,3-glucanase substrates. The presence of B-1,3-glucanase may also be detected using immunoassays. Any of the assays that monitor a detectable signal, such as fluorescence, may be performed in microtiter plates and are amenable to use in high throughput screening.

A further embodiment of the invention provides for a method of screening for a biological control agent that induces systemic resistance in a plant comprising contacting a plant sample with a biological control agent and detecting both the chitinase activity and the B-1,3-glucanase activity in the sample. In a preferred embodiment, the chitinase activity is determined by a glycol chitin plate assay and the B-1,3-glucanase activity is determined by an aniline blue plate assay. Other methods may be used to detect the activity of chitinase and B-1,3-glucanase as discussed above.

The methods of screening for biological control agents that induce systemic resistance as described above may also be used to screen chemical control agents that induce systemic resistance.

The present invention further provides methods for inducing disease resistance to a plant pathogen in a plant or a plant part, wherein the methods lead to reduced phytotoxicity in the plant or the plant part. In some embodiments, the method does not cause any phytotoxicity in the plant or plant part. Phytotoxicity is a problem often associated with many biocontrol agents (Chase, Index for Fungicide and Bactericide Research at CFREC-Apopka, 1981 through 1993, MREC Research Index). Phytotoxicity can be classified into the following categories: fundamental phytotoxicity, overload phytotoxicity, cumulative phytotoxicity, combination phytotoxicity, placement phytotoxicity, and episodic phytotoxicity. Phytotoxicity may result when the crop is sensitive to the biocontrol agent, the agent is applied at a higher than recommended rate, the components in a biocontrol agent mixture interact to damage the crop, the biocontrol agent is applied during unusually hot weather, or the biocontrol agent is applied at sensitive growth stages. Common injury symptoms from a biocontrol agent application are chlorotic spots on leaves in the upper canopy where plant contact with a biocontrol agent is the highest. The biocontrol agents of the present invention described herein can be applied to a plant, a plant part, or the soil around the plant, inducing disease resistance against various plant pathogens without causing any phytotoxicity. In some embodiments, the biocontrol agent of the present invention is applied at 1-100 gram/acre rate or more with $3 \times 10^{10}$ spores or cells per gram *Bacillus mycoides* isolate BmJ in the biocontrol agent. For example, the biocontrol agent is applied at about 10 gram/acre, about 20 gram/acre, about 30 gram/acre, about 40 gram/acre, about 50 gram/acre, about 60 gram/acre, about 70 gram/acre, about 80 gram/acre, about 90 gram/ acre, about 100 gram/acre, or more with $3\times10^{10}$ spores or cells per gram *Bacillus mycoides* isolate BmJ in the biocontrol agent.

In addition, the biocontrol agents of the present invention described herein can be used together with a second biocontrol agent to reach desired disease control effects, wherein the second biocontrol agent if used by itself can cause phytotoxicity in the plant before reaching the same desired disease control effects. To reach the desired disease control effects, the biocontrol agents of the present invention and the second biocontrol agent can be used in mixtures, or in rotations. In some embodiments, the desired disease control effects are reached due to the synergistic effects of combining the biocontrol agents of the present invention and a second biocontrol agent, so the second biocontrol agent can be applied with reduced amount and/or less often. In some embodiments, the second biocontrol agent is a fungicide or a bactericide.

Method of Producing *Bacillus* Spores

Previously no one has ever described a broth spore production media for *B. mycoides*. Published literatures in this field are mainly related to producing fermentation products from *B. mycoides*, but not sporulation (e.g., Abdel-Naby, et. al. 1998. Production and Immobilization of Alkaline Protease from *Bacillus mycoides*. Bioresource Technology 64: 205-210., and Borah et. al. 2002. The influence of nutritional and environmental conditions on the accumulation of poly-β-hydroxybutyrate in *Bacillus mycoides* RJL B-017. Journal of Applied Microbiology 92: 776-783).

The present invention provides methods of producing *Bacillus* spores. In some embodiments, the *Bacillus* species is *B. mycoides*. The invention is based on the unexpected discovery that the absence of glucose or very low concentration of glucose in the media promotes sporulation of *Bacillus* species, e.g., *B. mycoides*, and that *Bacillus* species, e.g., *B. mycoides* strain, does not sporulate when too much glucose is in the medium.

In broth culture, *B. mycoides* forms chains of cells. In standard laboratory broth media containing glucose such as Trypticase soy broth, *B. mycoides* (e.g., *B. mycoides* J) forms cell chains that do not sporulate. Fresh cells or freeze dried cells of *Bacillus* species can be used in a biocontrol agent to induce disease resistance in a plant. However, fresh cells and freeze dried cells are not very stable and freeze dried cell chains did not disperse effectively in water.

The general approach for inducing and optimizing sporulation in *B. subtilis* is to start with a laboratory media such as Difco sporulation media which contains protein and mineral salts and add glucose to achieve a high cell density before cells sporulate (e.g., Warriner et al., Enhanced Sporulation in *Bacillus subtilis* Grown on Medium Containing Glucose: Ribose. 1999, Letters in Applied Microbiology 29:97-102). Another example used Difco sporulation media with glucose added in batch or fed batch culture is described in Clemente et. al. (Predicting Sporulation Events in a Bioreactor Using an Electronic Nose. 2008, Biotechnology Bioengineering 101 (3):545-552).

When we tried this approach by using a medium comprising a protein source, with added glucose, BmJ did not sporulate in any media with glucose concentration above about 1.5 grams per liter. With 1.5 g/l glucose or less BmJ would sporulate. The protein source could be either laboratory type sources such as soy peptone or bulk commercial sources such a soy meal or soy protein concentrates, rice protein or wheat protein. Meat derived proteins may also be used unless one has to comply with organic rules. Higher concentrations of glucose at 3 g/l up to 50 g/l produced cultures with very high cell density indicating glucose utilization but these never sporulated. However BmJ would sporulate in protein media with sucrose as the carbon source although assays of sucrose at the termination of cultures showed that BmJ used very little sucrose. It is also determined that BmJ would grow and sporulate with equivalent yield in protein media without any added glucose or sucrose. With these basic results, a series of experiments were conducted to evaluate different commercial protein sources and optimize concentrations of the other ingredients for cost and spore yield, Phosphate (used primarily to buffer media at pH 7), yeast extract and mineral to come up with the final recipe.

We tested many different protein sources and amounts in media and provided there was minimal or no glucose. *B. mycoides* sporulate in all media. Therefore, our invention develops a low cost industrially suitable broth media in which *Bacillus* species, e.g., the BmJ can grow as cell chains, which form endospores and in which the cell chains and cells would disintegrate and release the spores, resulting in a cell free dispersed spores that can be further recovered, dried and formulated. The spores disperse easily in water and spray uniformly.

Therefore, the methods comprise culturing *Bacillus* cells in a liquid production medium containing no glucose, or very low concentration of glucose. In one embodiments, the concentration of glucose in the medium is about 1.5 gram/liter, or less that about 1.5 gram/liter, for example, less than about 1.4 gram/liter, less than about 1.3 gram/liter, less than about 1.2 gram/liter, less than about 1.1 gram/liter, less than about 1.0 gram/liter, less than about 0.9 gram/liter, less than about 0.8 gram/liter, less than about 0.7 gram/liter, less than about 0.6 gram/liter, less than about 0.5 gram/liter, less than about 0.4 gram/liter, less than about 0.3 gram/liter, less than about 0.2 gram/liter, less than about 0.1 gram/liter, less than about 0.01 gram/liter, less than about 0.001 gram/liter, or less.

The medium can comprise one or more protein sources. In some embodiments, the protein sources do not contain glucose, or contain very low concentration of glucose so that the protein sources can provide enough amino acid supplies to the bacteria growth but do not raise the glucose concentration in the medium more than about 1.5 gram/liter. Optionally, the medium can comprise one or more carbon sources that do not contain glucose, or do not raise the glucose concentration in the medium more than about 1.5 gram/liter.

In some embodiments, the methods further comprise removing the resulting bacterial spores from the production medium. In embodiments, the methods further comprise drying the bacterial spores, and, optionally, blending the bacterial spores with a carrier.

Non-limiting examples of the protein ingredient in the production medium include soybean meal, soy flour, soy protein concentrate, bacteriological peptone, tryptone, tryptose, casein peptone, meat peptone, proteose peptone, pancreatic digest of casein, pancreatic digest of gelatin, pancreatic digest of soybean meal, papaic digest of soybean meal, peptic digest of animal tissue, acid hydrolyzate of casein, lactalbumin hydrolysate, meat extract powder, liver extract powder, gelatin peptone, soya peptone, yeast extract powder, acid hydrolyzate of soy, beef extract powder, brain-heart infusion solids, gelatin, hemoglobin powder, skim milk, and combination thereof. In some embodiments, the protein ingredient comprises essential ingredients that can be found in one or more materials mentioned above.

The bacterial spores may be removed from the production medium by any methods known in the art, for example, by means of continuous flow centrifugation or filtration, such as those described in Gosh et al., Isolation and Characterization of Superdormant Spores of *Bacillus* Species, Journal of Bacteriology, March 2009, p. 1787-1797. Other basic methods, such as batch centrifuge, vacuum filtration, etc., or any known methods for separating small solid particles from a liquid can be used.

The bacterial spores can be dried with or without the addition of carriers using conventional drying processes or methods. These drying processes and methods include evaporation, freeze drying, tray drying, spray drying, fluidized-bed drying, and drum drying. The resulting dry bacterial spores may be processed further, such as by milling or granulation, to achieve a specific particle size or physical format. Carriers may be added after drying the bacterial spores.

Formulations

In some embodiments of the present invention, the bacterial spores of the present invention are blended with carriers. Carriers are inert formulation ingredients added to the bacterial spores that may improve the efficacy, recovery, or physical properties of the spores. They can also aid in packaging and administration. The carriers can be added in combination or individually. The carriers are bulking agents, anti-caking agents, protectants, and/or anti-oxidation agents in some embodiments of the present invention. Some examples of useful carriers include sugars (e.g., lactose, trehalose, sucrose), polysaccharides (e.g., starches, maltodextrins, methylcelluloses), salts (e.g., sodium chloride, calcium carbonate, sodium citrate), proteins (e.g., whey protein, peptides, gums), lipids (e.g., lecithin, vegetable oils, mineral oils), and silicates (e.g., clays, amorphous silica, fumed/precipitated silicas, silicate salts). In one embodiment, the carrier used is attapulgite clay. In some embodiments, the carriers are added after removal of the bacterial spores from the production medium, during drying, and/or after drying.

In some embodiments of the present invention, the bacterial cells belong to the *Bacillus* genus. Spore-forming bacterial species within this genus that may be useful as biopesticides include *Bacillus mycoides, Bacillus subtilis, Bacillus amyloliquefaciens, Bacillus licheniformis, Bacillus pumilis, Bacillus megaterium* and *Bacillus thuringiensis*. The present invention, according to one embodiment, involves *Bacillus mycoides* cells from isolate BmJ having accession number NRRL B-30890.

In some embodiments, the dried bacterial spores can be used to make wettable power formulations. For example, the spores can be mixed with wetting agents or emulsifiers (e.g., surfactant). An emulsifier (also known as an emulgent) is a substance that stabilizes an emulsion by increasing its kinetic stability. In some embodiments, the wetting agents are soil wetting agents, such as clays. For example, the wetting agent is selected from the group consisting of attapulgite clay, kaolin-type clays, and Barden clays.

In addition, it can be an advantage to have a liquid formulation of microbial spores such as BmJ rather than a powder. Liquid will not form dust and can be more easily poured/measured and may mix better with some other products in tank mix.

The issue with liquid formulations is to find a carrier in which the spores are stable. In water based carriers microbial spores may germinate and resulting vegetative cells die or spores may not be stable in water. Oils can be suitable liquid carriers because the oils contain no water (0 water activity) and spore germination is inhibited. However, to mix with water the formulation also needs to contain an emulsifier to disperse the oil in water to spray. In such formulations spores may be adversely affected by either the type of oil and or the emulsifier.

The present invention provides liquid formulations of *Bacillus* spores. In some embodiments, the *Bacillus* is *B. mycoides*. In some embodiments, the *B. mycoides* is the BmJ isolate. The liquid formulations comprise one or more oils as carriers. The oil can be any suitable one that makes the spores stable. For example, the oil may comprise a solvent-refined light paraffinic distillate (CAS #64741-89-5). The solvent-refined light paraffinic distillate may comprise fatty acid alcohol C12, C13, and/or C14. In some embodiments, the fatty acid alcohol is ethoxylated. In some embodiments, the carrier is Sunspray 7E (EPA Registration No. 00086200008).

In some embodiments, the formulation is made by simply blending dry BmJ spore powder in the oil to achieve the desired spore concentration. For example, spores powder was blended in the oil to a concentration of about $1\times10^6$, about $1\times10^7$, about $1\times10^8$, $1\times10^9$, $1\times10^{10}$ or more spores per ml oil, for example, about $1\times10^9$ spores per ml oil. Spores are stable in this formulation when stored at more than about 3 hours, about 4 hours, about 5 hours, or more at 50° C., or for more than 6 months, more than 7 months, more than 8 months, more than 9 months, more than 10 months, or more than a year at 37° C., or for more than 10 months, more than 1 year, more than 1.5 years, or more than 2 years at room temperature (22-25° C.).

This formulation can then be diluted in water and sprayed. For example, oil formulation of $1\times10^9$ spores per ml can be diluted 1:100 in water for a final concentration of $1\times10^7$ spores per ml in the final spray.

In some other embodiments, the carrier is a methylated vegetable oil. Vegetable oils, saturated or unsaturated, edible or inedible, include, but are not limited to, canola oil, sunflower oil, safflower oil, peanut oil, bean oil, linseed oil, tung oil, and soybean oil. Vegetable oils can be methylated to make it emulsifiable.

The wettable powder formulation of and oil formulation of BmJ spores can equivalent results in field trials against pathogens.

The present invention according to one embodiment has a production medium with a pH of 2.0 to 12.0, for example, about pH 2.0, about pH 3.0, about pH 4.0, about pH 5.0, about pH 6.0, about pH 7.0, about ph 8.0, about pH 9.0, about pH 10.0, about pH 11.0, or about pH 12.0. In another embodiment, the production medium has a pH of 4.0 to 10.0. In one embodiment, the production medium has a pH of 6.0 to 8.0. Preferably, in yet another embodiment the production medium has a pH of 6.5-7.5.

The present invention in another embodiment produces bacterial spores with a final bacterial spore concentration after drying of at least 1×10E0 spores per gram, at least 1×10E1 spores per gram, at least 1×10E2 spores per gram, at least 1×10E3 spores per gram, at least 1×10E4 spores per gram, at least 1×10E5 spores per gram, at least 1×10E6 spores per gram, at least 1×10E7 spores per gram, at least 1×10E8 spores per gram, at least 1×10E9 spores per gram, at least 1×10E10 spores per gram, at least 1×10E11 spores per gram, or at least 1×10E12 spores per gram.

The spores produced by using the present application can be used for many purposes. In some embodiments, The spores can be used in a biopesticides formulation to control one or more plant diseases, such as those described in Bargabus et al., Physiological and Molecular Plant Pathology, (2002), 61:289-298, and Bargabus et al., Biological Control (2004) 30:342-350. In some embodiments, the spores can be used for culturing *Bacillus mycoides* cells which can further be used to produce useful productions, such as polyhydroxybutyrate according to the methods described in U.S. Pat. Nos. 7,129, 068 and 7,273,733, and alkaline protease as described in Abdel-Naby et al., 1998, Production and immobilization of alkaline protease from *Bacillus mycoides*, Bioresource Technology, 64(3):205-210.

The present methods can be modified to produce greater cell mass prior to sporulation to give a greater spore yield of *Bacillus* species, such as *Bacillus mycoides*. In some embodiments, the methods comprise growing the *Bacillus* species in a medium comprising one or more protein sources, with a feed of a low concentration of glucose for an initial period of the culture. The feed can be continuous or pulsed. The total glucose fed to the culture can be greater than 1.5 g/l over time, but the dynamic concentration would never exceed 1.5 g/l. The initial period of feeding glucose may be decided based on the fermentation process. For example, the initial period can be the first 12 hours, 24 hours, 36 hours, 48 hours, or more of a 72 hour fermentation.

The invention having been described, it will be apparent to ordinarily skilled artisans that numerous changes and modifications can be made thereto without departing from the spirit or the scope of the appended claims.

All publications and patents cited herein are expressly incorporated by reference for all purposes.

This invention is further illustrated by the following examples that should not be construed as limiting. Those of skill in the art should, in light of the present disclosure, appreciate that many changes can be made to the specific embodiments which are disclosed and still obtain a like or similar result without departing from the spirit or scope of the invention.

DEPOSIT INFORMATION

A sample of *Bacillus mojavensis* isolate 203-7 has been deposited with the Agricultural Research Service Culture Collection located at the National Center for Agricultural Utilization Research, Agricultural Research Service, U.S. Department of Agriculture, 1815 North University Street, Peoria, Ill. 61604 Feb. 13, 2006. *Bacillus mojavensis* has been assigned the depository accession number NRRL B-30893.

To satisfy the enablement requirements of 35 U.S.C. 112, and to certify that the deposit of the isolated strains of the present invention meets the criteria set forth in 37 CFR 1.801-1.809, Applicants hereby make the following statements regarding the deposited *B. mycoides* isolate J and *Bacillus mojavensis* isolate 203-7:

1. During the pendency of this application, access to the invention will be afforded to the Commissioner upon request;
2. Upon granting of the patent the strain will be available to the public under conditions specified in 37 CFR 1.808;
3. The deposit will be maintained in a public repository for a period of 30 years or 5 years after the last request or for the enforceable life of the patent, whichever is longer;
4. The viability of the biological material at the time of deposit will be tested; and
5. The deposit will be replaced if it should ever become unavailable.

Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of deposited strains will be irrevocably removed by affording access to the deposited strains

EXAMPLES

Materials and Methods

Preparation of *Bacillus* Spores

The preferred embodiment for commercial use is to produce spores as the active ingredient. Spores are more efficient to produce and more stable than fresh cell or freeze dried cell preparations. *B. mycoides* isolate J (aka BmJ) spores are prepared in a fermentation process, recovered from the fermentation broth and dried to create a spore powder. This spore powder is then formulated by blending with attapulgite or other suitable clay materials or may be suspended in other carriers such as mineral oil. Spore preparations are produced according to the following steps:
1. Culture maintenance and storage
2. Inoculum preparation
3. Fermentation
4. Spore recovery
5. Drying
6. Formulation Culture Maintenance and Storage The "J" isolate of *B. mycoides* having accession number NRRL B-30890 was one of a number of *bacillus* strains isolated as single colonies from dilution plating of sugar beet leaf washes. A "master" stock of this single colony isolate was prepared by plating on potato dextrose agar (PDA), aseptically washing the plate with a sterile cryo fluid consisting of 10% glycerol and 1% trypticase soy broth. Harvested cells are stored in 1.0 ml aliquots at minus 80 degrees C. All subsequent cultures of the J isolate are traceable to this master stock prepared from the single colony "J" isolate.

Working stock cultures are prepared from the master stock as follows. A drop of master stock is used to inoculate trypticase soy broth which is incubated with shaking for 24 hours at 25 degrees C. This broth is used to inoculate a set of potato dextrose agar (PDA) or trypticase soy agar (TSA) plates which are incubated at 25° C. for three to five days. The PDA and/or TSA can be produced using recipes well known to those skilled in the art. Plates are aseptically washed with sterile cryo fluid and the wash is dispensed to sterile 1.0 ml tubes and stored at minus 25° C. Identity of working stock cultures as *B. mycoides* relies on distinctive spiral colony morphology (Franco et al., Colony shape as a genetic trait in the pattern-forming *Bacillus mycoides*, BMC Microbiology 2002, 2:1-15) and on assays for induction of systemic resistance in sugar beets. *B. mycoides* colony forms a spiral or swirl shape on agar and will either be clockwise or counterclockwise depending on the strain.

Inoculum Preparation

A working stock culture is thawed and used to inoculate a first stage inoculum culture of BmJ Production Medium (described below) or trypticase soy (TS) broth typically 100 ml in 250 ml flasks which are incubated at 25 degrees C. for 24 to 36 hours. Typically two 100 ml cultures are used to inoculate 10 liter bench production cultures. For full production scale cultures, the first stage inoculum is used to a start a second stage inoculum typically in 2 to 10 liters of either BmJ Production Medium or TS broth.

BmJ Production Medium

BmJ Production Medium consists of:

|  | grams per liter |
|---|---|
| Finely milled defatted soybean meal | 10 |
| Glucose | 1.5 |

| | grams per liter |
|---|---|
| Yeast extract | 0.25 |
| $K_2HPO_4$ | 2.5 |
| $KH_2PO_4$ | 1.1 |
| $MgSO_4 \cdot 7H_2O$ | 0.25 |
| NaCl | 0.1 |
| $MnCl_2$ | 0.01 |

All ingredients are technical or commercial grade. The pH should be 6.5-7.5 after autoclaving. Other commercial protein ingredients such as toasted soy flour, or soy protein concentrates may be substituted at 4 to 10 grams/liter of media.

Fermentation

Fermentation for test or commercial use may be conducted in any suitable fermentation vessel designed to be steam pressure sterilized and equipped for agitation and introduction of air. Culture media for spore production is typically the production media described above, however any suitable media containing sugar and protein sources and other nutrients that support cell growth and sporulation, but having about 1.5 g/l glucose, or less than about 1.5 g/l glucose may be used. Fermentations are typically conducted at 25 C to 30 C for 36 to 96 hours, typically 72 hours. Final spore concentration in the medium is determined by microscope hemocytometer count or as colony forming units by dilution and plating on TSA or PDA.

Spore Recovery and Drying

After completion of the fermentation, spores are recovered using a continuous flow centrifuge, then air dried and milled to a fine powder. Any other suitable drying method with a temperature below that which will damage or kill the spores can be used. Generally the treatment is less than about 65° C. for a few minutes (e.g., about 1 min, about 2 mins, about 3 mins, about 4 mins, about 5 mins, about 6 mins, about 7 mins, about 8 mins, about 9 mins, about 10 mins, or more), or less than 50° C. with longer exposure (e.g., about 5 mins, about 10 mins, about 15 mins, about 20 mins, or more). Spray drying can be used instead. This dry powder is the active ingredient formulated in clay or other carrier for use. The final spore powder may contain 1×10E10 to more than 1×10E12 spores per gram. Spores may also be recovered by filtration or other suitable means and dried under any conditions that do not kill the spores.

Formulation

Dry spore powder is blended with a carrier for application to plants. The carrier aids suspension of the spores in water and provides a volume of material that is easy to use. Often, the carrier (e.g., attapulgite clay, kaolin-type clay, barden clay, or any suitable type of oil) is blended with spores for a final spore concentration of 3×10E10 spores per gram. Application of this formulation was typically 25 to 125 grams per acre depending on the crop and disease.

In the following examples where BmJ spores were applied, the BmJ spores were in a wettable powder formulation, or an oil suspension formulation, at the indicated concentrations.

Example 1

Isolation and Testing of *Bacillus mycoides* Isolate BmJ

*Bacillus mycoides* isolate J (BmJ) was isolated from sugar beet leaves as follows. Leaf samples from sugar beets plants that had reduced infection by *Cercospora beticola* (CB), the fungal pathogen that is the causal agent of *Cercospora* leaf spot, were collected from a sugar beet field in Sydney Mont. The leaves were washed and pasteurized. Endospores were isolated from the pasteurized wash. The endospores were grown and tested for the ability to induce resistance to CB in sugar beets. One of the isolates, BmJ, was selected for use as a biological control agent because it provided the best control of isolates tested in early glasshouse trials.

In preliminary studies, a spontaneous Rifampicin resistant mutant of BmJ, that did not differ in growth rate or disease control capabilities from BmJ, was utilized in repeated attempts to isolate BmJ at 3, 6, 9, and 18 d post treatment from distal untreated and treated sugar beet leaves and petioles (Jacobsen, unpublished work). Due to the low level of BmJ populations on treated leaf surfaces and the lack of Rifampicin mutants isolated from distal untreated leaves, it was concluded that the level of disease control from BmJ treatment could not be due to direct effects of BmJ on CB (Bargabus, et al., Physiological an Molecular Plant Pathology, 61:289-298 (2002), herein incorporated by reference).

Example 2

Testing of BmJ in Growth Chamber Experiments

BmJ Preparation

*B. mycoides* isolate J (BmJ) cells, originally isolated from sugar beet leaves from Sidney, Mont. in 1994, were stored at −80° C. in 10% glycerol and 1% tryptic soy broth (TSB) (Difco). For fresh cell preparations, BmJ was cultured in TSB for 48 h (28° C.). Cells were centrifuged 15 min at 10000 g (4° C.), washed with sterile water (2×), then resuspended in distilled water. The optical density was adjusted to A600 1.0, then diluted 1:2 based on optical density curves confirmed by dilution plating. This optical density and dilution provided for approximately $1 \times 10^8$ cfu/ml. The precise number of cells was not determined due to the chain-forming nature of the organism. For experiments testing dead cells, BmJ was autoclaved in water for 30 min following washing. Autoclaved cells were tested for lack of viability by plating 100 microliters onto three plates of 50% tryptic soy agar (TSA). For field studies, either fresh BmJ cells prepared as described above or a spray-dried formulation, containing $2 \times 10^{13}$ cfu/g before dilution, prepared by Chris Hanson Labs (Milwaukee, Wis., U.S.A.) were used.

Fungal Culture

*C. beticola* (GB) (wild type isolate EC3, isolated in Sidney, Mont. in 1996) was grown on V-8 agar for a minimum of two weeks with exposure to fluorescent or natural light for at least one week to promote sporulation. Spores were harvested at approximately 30 days after plating in 0.1 carboxymethyl cellulose by scraping with a cotton swab, counted with a haemocytometer and adjusted to $1 \times 10^4$ spores/ml.

Plant Culture

Sugar beet varieties Holly Hybrid (HH) 88 (hybrid) and Seedex 920002 (inbred) were seeded into flats for germination, transplanted into 4" pots after I week, and grown in the glasshouse for 6 weeks in MSU mix (⅓ sand, ⅓ peat and ⅓ topsoil plus the wetting agent Aquagrow 2000, Aquatrols, Chemy Hill, N.J.). Plants were maintained at 24±2° C. and were watered daily and fertilized twice a week to maintain vigorous growth. Photoperiod was 16 h light and 8 h dark.

Growth Chamber Experiments

For growth chamber experiments, the leaf penultimate to the oldest two true leaves of sugar beet plants, in replicates of 10, was treated with BmJ, Acibenzolar-S-methyl (ASM, 50 ppm a.i.; ActigardS50 WG, Syngenta, Greensboro, N.C.), or dead BrnJ in 3-glucan with an aerosol sprayer. After drying, the treated leaf was covered with a plastic bag to ensure spatial separation from CB. The susceptible sugar beets were incubated for three days which was previously determined to be the timing that provided the best level of disease control [5], at which time the remainder of the leaves were challenged with the fungal pathogen CB (104 spores ml-'), which was applied to near run-off using an aerosol sprayer. After treatment, plants were transferred to a 28° C. growth chamber equipped with plastic tents and humidifiers. Plants were kept at 100 humidity for 72 h following inoculation with CB. Disease severity was calculated according to the KWS scale [20] and disease reduction was determined for the various inducing agents at 14 and 21 days post inoculation.

To determine the effectiveness of BmJ at reducing disease severity of Cercospora leaf spot on sugar beet while spatially separated from CB, the distal untreated leaves of BmJ-treated plants were challenged with CB 3 d post treatment. ASM and dead BmJ in 10 (3-glucan were also used as treatments before fungal challenge as positive and negative controls, respectively. All plants were rated using the KWS (1-9) scale at 14 and 21 d post challenge.

Results

The more susceptible of the two cultivars of sugar beet tested (HH88, a hybrid), resulted in the greatest systemic reduction in disease severity (−80% reduction) following priming with BmJ (Table 1). The decreased occurrence of leaf spot symptoms was statistically significant in comparison to the negative control (dead BmJ treatment), but not statistically different from the 63.6% reduction resulting from ASM treatment (Table 1). Priming HH88 sugar beets with virulent CB did not statistically reduce disease symptoms (Table 1). The inbred sugar beet cultivar (Seedex 920002) was less susceptible than its hybrid counterpart, and the overall disease severity was lower. With the inbred cultivar, BmJ was less effective than ASM-pretreatment, however the approximate 2% difference was not statistically significant (Table 1). The 66.7% reduction in disease severity noted with the inbred variety following BmJ treatment was statistically higher when compared to the negative (dead BmJ) control pretreatment (Table 1). Dead BmJ cells in p-glucan were not effective at controlling disease when applied to either cultivar when compared to untreated controls (data not shown) and plants not challenged with CB showed no infection (Bargabus, et al., Physiological an Molecular Plant Pathology, 61:289-298 (2002)).

TABLE 1

Systemic disease control of Cercospoa leaf spot on two different cultivars of sugar beet using B. mycoides isolate BmJ and acibenzolar-S-methyl in glasshouse experiments

| | Disease Severity | | | | | |
|---|---|---|---|---|---|---|
| | HH88[a] | | Seedex[a] | | % Reduction at 21 DPC[b] | |
| Treatment[c] | 14 DPC | 21 DPC | 14 DPC | 21 DPC | HH88[a] | Seedex[a] |
| Control[d] | 5.76 | 14.34 | 0.32 | 0.48 | n.r. | n.r. |
| C. beticola | 5.24 | 14.10 | n.d. | n.d. | n.r. | n.r. |
| Acibenzolar-S-methyl | 0.76 | 5.26 | 0.16 | 0.17 | 63.6 | 64.6 |
| B. mycoides | 1.03 | 2.94 | 0.13 | 0.16 | 79.5 | 66.7 |
| LSD (0.05)[e] | 2.87 | 3.78 | 0.09 | 0.12 | n.d. | n.d. |

[a]Holly Hybrid 88 (HH88, hybrid) and Seedex 920002 (Seedex, inbred) were the two sugar beet cultivars used in glasshouse experiments.
[b]DPC = days post challenge with C. betieo/a.
[c]Plants were treated with dead B. mycoides isolate BmJ in (3-glucan (control), C. betieola (virulent on HH88 and Seedex), acibenzolar-S-methyl, or live B. myeoides isolate BmJ on one leaf, then challenged 3 days later with e. betieo/a, the fungal pathogen, on the distal untreated leaves.
[d]Control = dead B. myeoides isolate BmJ cells applied with (3-glucan.
[e]LSD = least significant difference (probability = 0.05).

Example 3

Testing of BmJ in Field Studies

Field Studies

Field studies were conducted at the Eastern Agricultural Research Center in Sidney, Mont. from 1996 through 2003. Sugar beet variety 'Beta 1996' was planted the first year, VDH 66140 was planted the second year, HH88 the third year, KW2262 the fourth year and Beta 2185 the fifth, sixth, and seventh years. All cultivars were equally susceptible to C. beticola infection (BetaSeed, Shakopee, Minn., U.S.A.). A spray-dried formulation of BmJ, suspended in water ($10^8$ cfu/ml), was used the first four years. In the last two years, freshly grown, washed cells were harvested from a 24 h tryptic soy broth culture grown at room temperature and prepared as described above, and applied to the plants. Fungicide treatments included triphenyltin hydroxide (TPTH, SuperTin, Griffin L.L.C.), propiconazole (Tilt, Syngenta Crop Protection, Inc) and tetraconazole (Eminent, Sipeam Agro USA Inc.) that were applied at 390, 253 and 876 g ai ha$^{-1}$, respectively. All treatments were applied at 1761 ha$^{-1}$ using a $CO_2$ backpack sprayer with a 4-nozzle boom starting at disease onset and continued at 14 day intervals for a total of four sprays. Plots were arranged "in a randomized complete block design with six replicates per treatment. Each block consisted of 6 rows (9.2 m long) spaced 56 cm apart, resulting in a plant density of approximately 100 000 plants ha$^{-1}$. The four middle rows from each block were treated, leaving the outside two rows of each block as border rows. One middle row from each block for each treatment was harvested for yield data. Disease evaluations were taken four times during the growing season and 100 leaves/replicate were rated using the KWS scale from 1 to 9 [20]. Area under the disease progress curve (AUDPC) was calculated for treated and untreated plants and percent disease control was determined as follows: 1-(diseases severity of untreated controls/disease severity of treated plants)*100.

To examine the efficacy of BmJ under field conditions, the biological control agent treatment was extended to the field. Several fungicide treatments were introduced 10 to make comparisons between BmJ and current control methods. The KWS scale was used to rate CB disease severity for consistency with glasshouse data.

Results

Field application of BmJ resulted in disease control superior to untreated control plants (38-91% reduction) and equivalent to the chemical disease control triphenyltin hydroxide (TPTH; 253 g/ha) in 2 (1997 and 2000) of the 6 years (Table 2). BmJ also produced similar disease control to propiconazole (Tilt; 104 g/ha) in 2 (1996 and 1997) of 3 years (Table 2). BmJ, applied in conjunction with Tilt, significantly improved CB disease control over Tilt alone in 1997. Overall, under all conditions tested, BmJ alone or in combination with Tilt was just as effective against CB as TPTH, the most widely used fungicide (Table 2). Measurement of the area under the disease progress curve (AUDPC) over 5 years for untreated controls showed that all treatments worked just as well under severe disease conditions as they did in years with less disease pressure (Table 2) (Bargabus, et al., Physiological an Molecular Plant Pathology, 61: 289-298 (2002)).

TABLE 2

Multi year analysis of Cercospora leaf spot reduction in the field using B. mycoides isolate BmJ, triphenyltin hydroxide and propiconazole or tetraconazole
Disease Reduction by Year[a]

| Treatment | 1996[b] | 1997 | 1998 | 1999 | 2000 | 2001 |
|---|---|---|---|---|---|---|
| B. mycoides | 62 | 81 | 51 | 66 | 91 | 38 |
| TPTH (390 g a.i.ha$^{-1}$) | 81 | 90 | 81 | 94 | 72 | 88[b] |
| B. mycoides + Tilt (253 g a.i.ha$^{-1}$) | 78 | 89 | 76 | 97 | 91 | 80[c] |
| Tilt (253 g a.i.ha$^{-1}$) | 68 | 72 | 82 | n.d. | n.d. | n.d. |
| LSD (0-05)[e] | 14 | 13 | 21 | 14 | 34 | 15 |
| AUDPC[f] | 330 | 220 | 176 | 30 | 17 | 73 |

[a]Percent disease control in untreated plots was zero.
[b]Sugar beet variety 'Beta 1996' was planted in 1996, variety VDH 66140 was planted in 1997, variety HH88 was planted in 1998, variety KW2262 was planted in 1999, and variety 'Beta 2185' was planted in 2000 and 2001, all of which are equally susceptible to C. betieo/a (BetaSeed).
[c]Fungicide treatment in 2001 was Eminent instead of TPTH.
[d]in the year 2001, B. myeoides was applied with tetraconazole (Eminent) (876 g a.i. hao,) instead of propoconazole (Tilt).
[e]lSD = least significant difference (probability = 0.05).
[f]AUDPC = area under the disease progress curve for C. betieo/a. AUDPC represents the disease severity during the field treatment years in untreated controls (higher number = more disease).
n.d. = no data.

Example 4

Disease Reduction Capabilities of B. Mycoides and B. Pumulis Isolates

Bacterial Cultures

Bacillus myeoides isolate J (BmJ) was originally isolated from the phylioplane of sugar beet. B. pumilus isolates 203-11.341-21-15.203-6, 341-20-14, 241-20-1, 203-3, 203-4, and 341-16-5 and B. mojavensis isolate 203-7 were isolated from embryos of germinating sugar beet seeds. B. pumilus isolates BMH5E-33 and BMH5E-40 were isolated from the sugar beet rhizosphere. All isolates were stored at −80'C in 10% glycerol and 1'% tryptic soy broth (Difco). For fresh cell preparations, the bacilli were cultured in tryptic soy broth for 48 hours at 28° C. Cells were centrifuged 15 min at 10,000 g (4° C.). washed with sterile water (2×), and resuspended in distilled water. The optical density was adjusted to $A_{600}$=1.0, and diluted 1:2 to obtain approximately $1 \times 10^8$ cfu/ml.

Fungal Culture

Cercospora beticola (CB) isolate EC3 (isolated in Sidney. Mont. in 1996) was grown on V-8 agar far a minimum of two weeks with exposure to fluorescent or natural light for at least one week to promote sporulation. Spores were harvested approximately 30 days. after plating in 0.1%, carboxymethylcellulose by scraping with a cotton swab, counted with a hemocytometer and adjusted to $1 \times 10^4$ spores/ml.

Disease Control Assays

Sugar beet cultivars Seedex 900012 and Holly Hybrid 88 in replicates of 10, were treated with a Bacillus mycoides strains, a Bacillus pumulus strain, acibenzolar-S-methyl (ASM, 50 ppm a.i. in distilled water. Actigard, 50 WG, Syngenta. Greensboro, N.C.) or distilled water with an aerosol sprayer to the leaf penultimate to the oldest true leaf. This leaf was then immediately bagged to ensure spatial separation from C. beticola, which was applied 3 days later at a rate of $1 \times 10^4$ spores/ml to near run-off on the remaining leaves using an aerosol sprayer. The sugar beets were kept at 28+/−2° C. and placed at 100% relative humidity for the first 48-72 hours, post-treatment. Plants were kept 28+/−2° C. until disease symptoms developed and were rated for disease at 21 days post-inoculation using the KWS scale, which rates percent disease severity on a scale of 0-9 (Kleinwanzler, 1970).

Results

Of the 14 different treatments applied to sugar beet cultivars Seedex 900012 and Holly Hybrid 88, four resulted in 50% disease reduction. The effective strains included BmJ, B. mojavensis isolate 203-7, and B. pumilus isolate 203-6 while the chemical inducer of systemic acquired resistance, ASM, also controlled disease. B. pumilus isolates 241-20-1 and 13MI-15E-40 reduced Cercospora leaf spot symptoms to a statistically significant level (Table 3) (Bargabus, et al., Biological Control, In Press (2004) herein incorporated by reference).

TABLE 3

Disease reduction capabilities of a pool of B. pumulis isolates, B. mycoides isolate BmJ, ASM, and water.

| | Disease severity at 21 days post challenge with C. beticola | |
|---|---|---|
| Treatment | HH88 | Seedex |
| water | 8.00[a] | 7.70[ab] |
| 203-3 | 5.82[a] | 5.58[b] |
| 203-4 | 6.95[a] | 7.65[ab] |
| 203-6 | 1.86[b] | 1.50[c] |
| 203-7 | 2.38[b] | 2.46[c] |
| 203-11 | 7.10[a] | 5.90[b] |
| BMH5E-33 | 6.42[a] | 6.60[b] |
| BMH5E-40 | 5.14[ab] | 5.45[bc] |
| 341-20-14 | 5.86[a] | 9.00[a] |
| 341-20-15 | 6.10[a] | 6.48[b] |
| 241-20-1 | 5.28[ab] | 4.66[bc] |
| 341-16-5 | 6.51[a] | 6.40[ab] |
| BmJ | 2.73[b] | 2.56[c] |
| ASM | 2.93[b] | 2.70[c] |

Example 5

Determining Induction of Systemic Acquired Resistance in Plants by Presence of Chitinase Protein Extraction For protein extractions, leaves distal to the treated leaves were collected from plants at 6 days post treatment with the live and dead BmJ, ASM, or water. One leaf per replicate was collected for each treatment and immediately placed in buffer (150 mm NaCl, 25 mm MES, pH 6-2). Apoplast extractions were collected as described by Klement [21] having substituted buffer (150 mM NaCl, 25 mm MES. pH 6 2) for water.

Western Analysis of Apoplastic Proteins

Apoplast samples were acetone precipitated (3:1 v/v), boiled in SDS sample buffer for 2 min, and resolved (1 5 ug per lane) (12% SDS-polyacrylamide gel electrophoresis (PAGE) gel) for 45 min (200 V) at pH 8.3 using midrange molecular standards (Sigma) for molecular weight determination. Proteins were then transferred to polyvinylidene fluoride membranes (Millipore) for 1 hour (100 V) in 25 mm Tris, 192 mm glycine, and 20% (v/v) methanol (pH 8.3) using a BioRad mini-blot apparatus [13]. Membranes were blocked with 3% BSA for 1 hour, incubated in primary antibody (anti-chitinase, diluted 1:5000) (Syngeta, Greensboro, N.C., U.S.A.) in 1 BSA for 1 hour, followed by incubation in secondary antibody (peroxidase conjugated, diluted 1:10 000) (Sigma). Colorimetric detection was performed using the 3-amino-9-ethylcarbazole (AEC) staining kit (Sigma). Loading equality was demonstrated with silver staining [26].

Determination of Chitinase Activity Following Non-Reducing PAGE

Apoplastic protein samples (1.5 ug per lane) were resolved on a 12% polyacrylamide gel containing 0.01% glycol chitin. Following electrophoresis, the gel was gently shaken for 2 h (3rC) in 100 mM sodium acetate buffer, pH 5.0 containing 1% (v/v) triton X-100. The gel was then stained with 0.01% calcofluor white M2R in 500 mm Tris-HCl, pH 8.9 for 5 min. The gel was quickly rinsed 3× with distilled water, then soaked overnight in the dark in distilled water. Chitinase isoforms were visualized as lytic bands under an uv light source [50]. Size comparisons were made between active isoforms and isoforms detected by western analysis using mid-range molecular markers (Sigma).

Chitinase Specific Activity Determination by Plate Assay

Sodium phosphate buffer (pH 5.0, 0.01 M) containing 1 agarose and 0.1% glycol chitin was added to a 9 cm diameter glass petri dish. Wells, 3 mm diameter, were excised from the agarose (three per sample for each of the three replicates per treatment). Dilutions of apoplastic protein (0.7, 0.35, and 0.23 ug) and chitinase standards (chitinase from Streptomycesgriseus Sigma) were loaded into the wells. The plate was incubated at 37° C. for 24 h. Following the incubation, 50 ml of 500 mM Tris-HCl (pH 8.9) containing 0.01% fluorescent brightener was added to the plate and incubated for 10 min. The plate was then quickly rinsed 3× with water, flooded with water, and destained overnight in the dark. Non-fluorescent lytic regions on a fluorescent background were measured while the plate was on an uv light source. Specific activity (mg of N-acetyl-n-glucosamine released /hr /mg of apoplastic protein) was determined by comparison of the diameters of the lytic regions for the standards and the lytic regions for the apoplastic protein samples [55].

Results

Analysis of PR-protein production was used to help evaluate the hypothesis that BmJ induced systemic acquired resistance to CB. A protein extract from leaves distal to the treated leaves was prepared as described above. A polyclonal antibody to tobacco chitinase (provided by Syngenta, Greensboro, N.C.) bound to several putative chitinases in sugar beet following treatment with BmJ, ASM and water. As a means of determining which isoforms were potentially involved in sugar beet defense responses, the activity of the isoforms was observed following non-reducing PAGE. Certain isoforms showed increased activity while others appeared to have reduced activity in sugar beet following BmJ-treatment. There was equal loading in the PAGE analyses, as demonstrated when the apoplastic protein samples were also run on a separate polyacrylamide gel, then silver stained. One of the isoforms produced in response to BmJ-treatment, but lacking in the water-treated plants, was also found following ASM treatment, which is known to induce plant systemic resistance responses. The overall changes in specific activity of chitinase in sugar beet following treatment with ASM, live and dead BmJ and water were determined. Even though ASM-treatment resulted in fewer active isoforms being produced than the BmJ-treatment, the specific activity level was statistically equal (Table 4). Both live BmJ and ASM treatments resulted in statistically higher chitinase specific activity that was nearly twice that observed with water or dead BmJ treatment (Table 4).

TABLE 4

Systemic sugar beet apoplastic pathogenesis-related protein activity six days post treatment with line and dead *B. mycoides* isolate BmJ, acibenzolar-S-methyl and water

| Treatment | Specific Activity | | |
|---|---|---|---|
| | Chitinase[a] | Beta-glycanase[b] | Peroxidase[c] |
| Water | 0.46 | 36.1 | 42.8 |
| Live *B. mycoides* | 1.02 | 77.9 | 61.6 |
| Acibenzolar-S-methyl | 1.26 | 198.6 | 71.4 |
| Dead *B. mycoides* | 0.45 | 37.7 | 26.8 |
| LSD (0.05)[d] | 0.21 | 36.1 | 12.2 |

[a] Chitinase specific activity expressed as milligrams of N-acetyl-n-glucosamine released per hour per milligram of apoplastic protein and is the mean of the data from three plants per treatment replicated three times.
[b] Beta-glucanase specific activity expressed as micrograms of glucose released per minute per milligram of apoplastic protein and is the mean of three plants per treatment replicate three times.
[c] peroxidase specific activity expressed as the changes in absorbance (470 nm) per minute per milligram of apoplastic protein and is the mean of three plants per treatment replicated three times.
[d] LSD = least significant difference (probability = 0.05).

Example 6

Determining Induction of Systemic Acquired Resistance in Plants by Presence of B-1,3 ¬ Glucanase Detection of B-1,3-Glucanase Activity Apoplastic proteins for each treatment (3.0 ug) were separated using acidic PAGE conditions as described by Reisfeld et al [39], with the following modification. In the running buffer, L-alanine was substituted for B-alanine with a final pH of 3.8 rather than the prescribed 4.3, allowing for better separation of the isoforms. Following separation, the gels were incubated in 0.1 M citrate buffer (pH 4.8) containing 250 mg laminarin per 100 ml of buffer at room temperature for 20 min. The gels were then transferred to 0.1% Congo red and incubated overnight with constant shaking at room temperature. The gels were then transferred to destaining solution (1 M NaOH) and incubated overnight at room temperature with constant shaking. B-glucanase activity was visualized as yellow-orange bands on a reddish-purple background.

Determination of B-1,3-Glucanase Specific Activity

The specific activity of sugar beet apoplastic B-1,3-glucanase was determined by measuring the release of glucose units from laminarin. Sodium acetate buffer (100 IJI, pH 5.0, 100 mM) containing 0.5% laminarin and 0.5 ug-2.0 ug apoplastic protein (plants per treatment replicated 3 times) was incubated at 3rc for 30-60 min. Following incubation, 900 ul of water and 1 ml of alkaline copper reagent [45] was added to each 2 reaction. The tubes were then placed into a boiling water' bath for 10 min. After cooling on ice, 1 ml arsenomolybdate color reagent [33] was added to each reaction. Once the bubbling had subsided, 10 ml of water were added to each tube before reading the A660. A standard curve was established by adding 5 ug-25 ug glucose to 1 ml total reactions that did not contain laminarin.

Results

Native polyacrylamide gel electrophoresis (PAGE) was run under acidic conditions to examine basic B-1,3-glucanases produced in response to ASM, BmJ or water treatment. Two active isoforms were produced in sugar beet following BmJ treatment. One of the two isoforms was also present and active in sugar beet following ASM-treatment, however both were lacking in water-treated plants. To determine the total activity of B-1,3-glucanase in sugarbeet, colorimetric assays were performed. BmJ-treated plants had a specific activity that was approximately twice that of the activity in water-treated plants, but approximately one-third the ASM-induced activity; both were statistically significant increases when compared to the water-treated and dead BmJ-controls (Table 4). Dead BmJ-treated plants had specific activities statistically equivalent to the water-treated controls (Table 4).

Example 7

Determining Induction of Systemic Acquired Resistance in Plants by Presence of Peroxidase Determination of Peroxidase Activity Apoplastic peroxidase activity from three plants per ASM, BmJ and water treatment (3 replicates of each) was measured using guaiacol reagent according to Hammerschmidt et al [15]. The concentration of protein as adjusted to give a change in absorbance units greater than 0.100, but less than 0.200, per minute. Specific activity was expressed as the increase inabsorbance (A470) over time (2 min) per mg of protein, as determined using Bradford reagent (BioRAD).

Determination of Peroxidase Activity Following Native-PAGE

Polyacrylamide gel electrophoresis was performed according to Reisfeld et al. [39]. Following electrophoresis, the gels were stained using a AEC staining kit (Sigma) for 16 hours while gently shaking in the dark. The gels were then rinsed with distilled water 3× for a total of 15 min to stop the reactions.

Results

Peroxidase is a PR-protein that can be measured using activity assays. BmJ treatment elicited significantly greater peroxidase activity in the apoplast of distal sugar beet leaves than water or dead BmJ treatment (Table 4). Peroxidase activity following BmJ treatment was also statistically equivalent to that elicited by ASM (positive control) treatment (Table 4). To determine if the increased activity noted in the chemical SAR-inducer and bacterial treatments—was due to plant production of new peroxidase isoforms, in-gel activity assays were performed. Both the ASM- and BmJ-treated plants had two additional active isoforms not detected in the negative (water) control. There were several other minor isoforms that present in the water controls as well.

Example 8

Methods of Screening for *Bacillus* Control Agents—Detection of Chitinase and B-1,3-Glucanase Activity Apoplastic Protein Extractions The leaf penultimate to the oldest true leaf was treated with one of the *Bacillus* strains. BmJ, ASM, or distilled water, in replicates of 3, with an aerosol sprayer, and immediately bagged. The plants were kept at 28+/−2° C. for 6 days at which time the apoplastic proteins were collected as described by Klement (1965), with the following modification: a buffer containing 150 mM NaCl and 25 mM MES, pH 6.2, was substituted for distilled water. The proteins were quantified by Bradford reagent (Bio-Red) using bovine serum albumin as standards and frozen at −80° C. until analyzed.

Glycol Chitin Plate Assay for Chitinase Activity

Apoplastic protein (0.009, 0.006, and 0.005 ug for each sample in replicates of 3) was added to wells in a 1% agarose gel containing 0.01% glycol chitin in a 14 cm diameter glass petri plate, along with chitinase standards (*Streptomyces griseus*, Sigma). The plates were incubated at 37° C. for 24 hours. Following incubation. 50 ml of 500 mM Tris-HCl (pH 8.9) containing 0.01°/fluorescent brightener [28] was added to the plate for 10 min. The plate was then rinsed three times with distilled water, flooded with water, and allowed to destain in the dark for 2-24 hours. The non-fluorescent lytic zones on a fluorescent background were measured while the plate was on a 302 nm UV light source. Specific activity (mg of N-acetyl-D-glucosamine released/hr/mg of apoplastic protein) was determined by comparison of the lyric zone diameter of the standards and the apoplastic samples (Velasquez. 2002).

Results-Chitinase as a Predictor of Disease Control

An increase in chitinase specific activity following treatment with a *Bacillus* control agent in comparison to the water-treated negative control constituted the classification of the agent as a SAR-inducer. The glycol chitin plate assays, for the determination of chitinase activity, had a reasonable level of precision with discrepancies having occurred only 9% of the time between independent experiments. The standard deviation within a subset in one independent replicate was approximately 10% and approximately 17% between subsets in one independent experiment.

Cumulative results of five independent experiments correctly identified all four SAR-inducers present in the pool of isolates tested and yielded four false positives and no false negative identifications (Table 5).

Aniline Blue Plate Assay for B-Glucanase Activity

Apoplastic protein (0.75, 0.50, and 0.25 ug for each sample in replicates of 3) was added to 3-mm diameter wells in a 0.5% agarose gel containing 0.005% aniline blue (MCB) and 0.5 m·l/ml laminarin (from *Laminaria digitata*, Sigma) in a 14 cm diameter glass petri plate, along with laminarinase (*Penicillium* spp., Sigma) standards (2×10.5-2×10-3 units of lamina~inase). The plates were incubated at 30° C. for 18-24 hours. Following Incubation, the pink lytic zones on a blue background were measured while the plate was on a white light source. Specific activity (ug of glucose released/min/mg of apoplastic protein) was determined by comparison of the lytic zone diameter of the standards and the apoplastic samples.

Results-B-1,3-Glucanase as a Predictor of Disease Control

An increase in B-1,3-glucanase specific activity following treatment with a *Bacillus* control agent in comparison to the water-treated negative control constituted the classification of the agent as a SAR-inducer. The aniline blue plate assay was highly reproducible with a standard deviations of 11% within subsets of one replication and 21% between subsets in one replication. There was a high degree of precision when using the aniline blue plate assay with few false positive identifications (0-40% between independent experiments) and no false negative identifications. Based on the increase in activity serving as an indicator of SAR induction, the cumulative results of two independent experiments yielded one false positive identification (Table 5).

Results—Chitinase and B-1,3-Glucanase as a Predictor of Disease Control There may be circumstances where the occurrence of chitinase and B-glucanase alone is not correlated with disease control (Punja, 2001), especially with fungal pathogens, since the enzymes function synergistically (Melchers and Stuiver, 2000). Therefore examination of the defense proteins together provides a more accurate prediction of disease control capability. Based on the assumption that increased activity for both defense proteins indicated SAR-inducing capacity, combined results from the glycol chitin and aniline blue plate assays correctly identified all SAR-inducing isolates, indicated by check marks in Table 5. Furthermore, relying on this method did not include any false-positive identification.

TABLE 5

Cummulative results of the methods for host-response based high-throughput screening for the identification of *Bacillus* control agents.

| Treatment | Aniline blue plates | Glycol chitin plates | Aniline blue and glycol chitin plates |
|---|---|---|---|
| water | 2.75cd | 1.56g | |
| 203-3 | 3.20cd | 2.55def | |
| 203-4 | 3.35hcd | 2.03fg | |
| 203-6 | 4.90ah | 2.97bcd | ✓ |
| 203-7 | 5.75a | 4.00a | ✓ |
| 203-11 | 4.00b | 2.04fg | |
| BMH5E-33 | 2.80cd | 2.1gefg | |
| BMH5E-40 | 2.35d | 2.22efg | |
| 341-20-14 | 3.85bcd | 2.68def | |
| 341-20-15 | 2.70cd | 2.14efg | |
| 241-20-1 | 2.55cd | 2.74cde | |
| 341-16-5 | 3.15cd | 3.44eb | |
| BmJ | 6.10a | 3.41 abc | ✓ |
| ASM | 5.70a | 3.09hed | ✓ |

Example 9

Methods of Screening for *Bacillus* Control Agents—Detection of Biphasic Hydrogen Peroxide Production Sugar Beet Protoplast Generation Sugar beet protoplasts were isolated from sugar beet leaves to provide a medium to measure hydrogen peroxide production. Sugar beet leaves were gently brushed on the adaxial and abaxial surfaces with a 50 ft bristle brush to create small abrasions. The leaves were then cut into 1 cm strips and vacuum infiltrated for 5 min with 0.7 M sucrose containing 3.8% CaCL2, CPW salts (Frearson et al, 1973), 1.2% cellulase (Sigma), and 0.4% macerozyme (ICN Biomedicals). The infiltrated leaves were incubated in the 0.7M sucrose-salt and enzyme solution for 24-48 hours in the dark. Following incubation, the enzyme solution was gently removed and the protoplasts were released into 0.7M sucrose containing 3.8'% CaCl2 and CPW salts by gently shaking the leaf strips in the solution. Phenol red oxidation for hydrogen peroxide production.

To determine if the *Bacillus* strains elicited biphasic hydrogen peroxide production in sugar beet, phenol red oxidation assays were performed according to Pick and Keisari (1980). Both protoplasts (250 protoplasts/reaction) and whole leaf disks (12 disks/reaction) were used to study the plant response. When using protoplasts, an external source of peroxidase (type 11 horseradish peroxidase, Sigma) was added to each reaction while in the latter case. The peroxidase contained within the added leaf disks was sufficient for the oxidation reaction. Phenol red reactions were run with each *Bacillus* strain alone, protoplasts alone, leaf disks alone, *Bacillus*-treated leaf disks, and combinations of *Bacillus* strains and protoplasts. *Bacillus* treated leaves were washed before adding to each reaction to remove a majority of the bacteria from the leaf surface. To calculate the amount of hydrogen peroxide produced in each instance, the A470 was compared to a standard curve established using 0-40 mM hydrogen peroxide and 6-2 ug/ml type II horseradish peroxidase. The amount of hydrogen peroxide produced from protoplasts in response to treatment with a *Bacillus* control agent was calculated as follows: amount of hydrogen peroxide produced in *Bacillus* protoplast reactions—(amount of hydrogen peroxide produced in protoplast only reactions+amount of hydrogen peroxide produced in *Bacillus*-only reaction). The amount of hydrogen peroxide produced by the leaf disks in response to *Bacillus* treatment was calculated as follows: amount of hydrogen peroxide produced by *Bacillus*-treated leaf disks-amount of hydrogen peroxide produced by leaf disks only reaction.

Results-Biphasic Hydrogen Peroxide Production Curves as Predictors of Disease Control Biphasic hydrogen peroxide production, as measured using phenol red oxidation, was used as an indicator of SAR-induction capability. In cases where a single burst of hydrogen peroxide occurred without the secondary, more prolonged AOS burst, the strain was classified as a non-SAR inducer. AOS production profiles were similar regardless of the plant material used to analyze the production pattern of hydrogen peroxide. The reproducibility was quite high with only 7% disagreement between independent experiments using protoplasts and leaf disks. All biphasic curves elicited by the *Bacillus* strains were statistically similar in timing and intensity. In all cases the primary peak (approximately 3 mM) occurred at 15 min post-treatment and the secondary peak (approximately 2-4 mM) occurred at approximately 2 hour post-treatment. False positive identification using this method occurred 8-15% of the time between independent experiments. ASM did not induce biphasic hydrogen peroxide production.

Example 10

Use of *Bacillus* Control Agent in Disease Control in Banana Plants

Spray-dried cells of *Bacillus mycoides* isolate J (BmJ) were prepared as described in Example 2. The spray-dried BmJ was applied aerially at a concentration of $1\times106$ cfu/ml at a rate of 7 gallons/acre to banana plants. The ability of the BmJ treatment to control the fungal disease Black Sigatoka (caused by *Mycosphaerella fijiensis*) was determined. The banana plants were infected by the pathogen *Mycosphaerella fijiensis* present in the field under naturally occurring conditions. Efficacy of BmJ treatments were evaluated in comparison with the fungicides TPTH at 5 oz per acre and Propaconizole at 10 oz per acre. These rates are the recommended application rates for these fungicides. Results were assessed by visual scoring of leaf tissue damage.

Results

Treatment of the banana plants with BmJ was just as effective at controlling Black Sigatoka as treatment of banana plants with the fungicide TpTH.

Example 11

Use of *Bacillus* Control Agent in Disease Control in Pecan Plants

Spray-dried cells of *Bacillus mycoides* isolate J (BmJ) were prepared as described in Example 2. The spray-dried BmJ was applied by an orchard spray mechanism at a concentration of 1×106 cfu/ml at a rate of 200 gallons/acre to pecan plants. The ability of the BmJ treatment to control the fungal disease Pecan scab (caused by *Cladosporium caryigenum*) was determined. The pecan trees were infected under naturally occurring conditions by the pathogen *Cladosporium caryigenum* present in the orchard. BmJ treatments were compared with the fungicide TPTH applied at the recommended rate of 5 oz per acre. Disease damage was rated by visual observation using a numerical scale.

Results

Treatment of the pecan plants with BmJ was just as effective at controlling Pecan scab as treatment of pecan plants with the fungicide TpTH.

Example 12

Use of *Bacillus* Control Agent in Disease Control in Cucumber Plants

The anthracnose and angular leaf spot-cucumber-pathosystems were used to compare disease control using induced systemic resistance by *Bacillus mycoides*, isolate BmJ and *Bacillus mojavensis*, isolate MSU 203-7.

Bacilli were applied as a first true leaf treatment at $10^9$ colony forming units (cfu)/ml 5 days before challenge inoculation with *G. cingulata*=$10^5$ conidia/ml and *P. syringae*=$10^4$ cfu/ml. Five days (seven days for the angular leaf spot-pathosystem) after challenge inoculation, disease development was compared to water treated and pathogen-induced controls. BmJ treatments significantly lengthened the latent period by approximately 1 day and decreased both total spore production by approximately 64% and the percentage of viable spores by approximately 54% in the anthracnose experiment. The percent of infected leaf area was significantly reduced by approximately 37% and 48% by *B. mycoides* and *B. pumilus*. Both *Bacillus* treatments also reduced the systemic movement by approximately 27% and 36% in the angular leaf spot experiment.

Example 13

Determining Impact of SA and NPR1 Signaling on Induction of Systemic Acquired Resistance in Sugar Beets Plants have a variety of means of defending themselves against pathogen attack. Some constitutive lines of defense include physical barriers that prevent pathogen ingress and can contain antimicrobial proteins and secondary metabolites (reviewed by Vorwork et al, 2004) and production of toxins that are deleterious to particular pathogens (reviewed by Wittstock and Gershenzon, 2002). Additionally, in some instances, plants can mount an inducible defense response upon pathogen challenge. Inducible broad-spectrum resistance provides long-term defense against a wide array of potential pathogens and has been described in several plant systems in response to a variety of different stimuli (Ryals et al, 1996; van Wees et al, 1997; Yoshioka et al, 2001, Yasuda et al, 2003).

Signaling components involved in elicitation of defense are largely unknown. However, several key players have been identified, such as salicylic acid ("SA") (Ollestam and Larsson, 2003; Shah, 2003; Alvarez, 2000; Shapiro and Gutsche, 2003), jasmonic acid (JA) and ethylene (Heil and Bostock, 2002, Anderson et al, 2004), all of which are considered secondary signal molecules. Some downstream signaling components, such as NON-EXPRESSOR OF PATHOGENESIS-RELATED GENES1 (NPR1) have been shown to be deployed during SA-dependent defense (reviewed by Dong, 2004). NPR1 has also been shown to orchestrate cross-talk between SA and JA pathways (Spoel et al, 2003). These antagonistic pathways elicit distinct subsets of defense-related proteins. SA-dependent pathways are associated with pathogenesis-related (PR) proteins such as chitinase, peroxidase, glucanase and PR-1 (reviewed by Durrant and Dong, 2004). JA and ethylene, on the other hand, are associated with production of thionins, defensins and proteinase inhibitors (Reymond et al, 2000; Xu et al, 2001).

SA is tied to the oxidative burst, one of the earliest events in the establishment of induced resistance. Interaction occurs between SA and active oxygen species (AOS) produced during the oxidative burst. SA can bind to and inhibit antioxidant enzymes leading to an increase in AOS concentration (Chen et al, 1993; Durner and Klessig, 1995). Additionally, hydrogen peroxide, one of the AOS, has been shown to be involved in the potentiation of phenylalanine ammonia lyase and benzoic acid 2-hydroxylase (Leon et al, 1995); two enzymes in one of the SA biosynthetic pathways (Coquoz et al, 1998). It has also been hypothesized that AOS may be involved in the liberation of free SA from elusive SA conjugates constitutively stored in plant cells (Leon et al, 1995).

SA and AOS are also linked to activation of NPR1, a protein that functions downstream of SA signaling. NPR1 is a constitutively expressed protein that contains domains which function in protein-protein interactions (Cao et al, 1997; Aravind and Koonin, 1999). The protein exists in an inactive multimeric state. Increased concentrations of AOS during the oxidative burst triggers overproduction of antioxidant enzymes in the plant. The AOS scavenging is hypothesized to create the reducing environment necessary to release an active monomer of NPR1 (Mou et al, 2003). The monomeric NPR1 moves to the nucleus, associates with TGA transcription factors and activates PR-genes (Fan and Dong, 2002).

Previously we have described the biochemical outcome of treatment of sugar beet with two biological control agents (BCA), *Bacillus mycoides* isolate Bac J (BmJ) (Bargabus et al, 2002) and *Bacillus mojavensis* (previously identified as *B. pumulis*) isolate 203-7 (203-7) (Bargabus et al, 2004). Both biological control agents induce resistance that affords protection against *Cercospora beticola*, the causal agent of *Cercospora* leaf spot, a devastating foliar pathogen of sugar beet (Weiland and Koch, 2004). Since the resistance is associated with production of SA-associated PR-proteins (peroxidase, 13-glucanase and chitinase), we have hypothesized the signaling pathway is SA dependent. Due to the fact both BCAs elicit an oxidative burst (Bargabus et al, 2003 and 2004), we have speculated that NPR1 may also be deployed in the establishment of resistance. In the current investigation we test these hypotheses to determine the role of SA and NPR1 in Bacilli-induced resistance in sugar beet.

Plant Culture

*Beta vulgaris* FC 607 germplasm (provided by Dr. Lee Panella, United States Department of Agriculture-Agricultural Research Service, Fort Collins, Colo.) was seeded into 20-cm diameter pots containing pasteurized Scotts Metro-Mix supplemented with Scotts Osmocote 14-14-14 (American Clay, Denver, Colo.). Seed was dusted with a 4:1(v/v) charcoallmetalaxyl (Apron, Gustafson, Plano, Tex.) mixture prior to planting to control damping off by *Pythium*. Plants were maintained at 22° C.±5° C. and were watered twice a week to maintain vigorous growth. At about four weeks, Imidacloprid (Marathon, 1% granular, ½ tsp/pot) and triazole (Strike, foliar spray, 1.9 g/l) (Olympic Horticultural Products Co., Mainland, Pa.) were used as preventatives for thriplaphid feeding and powdery mildew respectively. Plants used in all experiments were between 5 and 7 weeks of age. The photoperiod of light was determined by natural sunlight of 12 to 15 hours.

Bacterial Cultures

*Bacillus mycoides* isolate Bac J (BmJ), originally isolated from sugar beet leaves in Sidney, Mont. in 1994, was prepared as previously described (Bargabus et al, 2002). *Bacillus mojavensis* isolate 203-7, originally isolated from embryos of germinating sugar beet seed in 1997, was prepared as previously described (Bargabus et al, 2004). *Bacillus pumulis* isolate BMH5E-33, originally isolated from the sugar beet rhizosphere in Sidney, Mont. in 1'997, was prepared as previously described (Bargabus et al, 2004). Treatment of Sugar Beet with Elicitors of Systemic Resistance [0114] Acibenzolar-S-methyl (ASM, 50 ppm a.i.; Actigard 50WG, Syngenta, Greensboro, N.C.), a known chemical of inducer of resistance, was applied as an experimental control for SA and NPR1 analysis. ASM and live and autoclave killed (dead), washed BmJ, 203-7 and BMH5E-33 cells were spray applied to near run off to all fully expanded leaves. Water was spray applied as an experimental negative control for all treatments. In NPR1 experiments, SA (2 mM in 0.1M potassium phosphate buffer, pH 7.0, containing 0.01% triton x-100) was added as an additional positive control. Extraction of Free and Conjugated Salicylic Acid from Sugar Beet Leaf Tissue.

Two main precursors, isochorismate (Wildermuth et al, 2001) and phenylalanine (Ribnicky et al, 1998), are implicated in the formation of SA during plant defense, both of which stem from the shikimic acid pathway (Metraux, 2002). Salicylic acid is produced locally in treated leaves and systemically in distal, untreated leaves during the establishment of systemic acquired resistance. Production is transient and free SA is rapidly modified to 2-0-b-D-glucosylsalicylic acid (Enyedi and Raskin, 1993), a hypothetical SA storage compound. Therefore the best measure of SA-dependency is gathered by measuring free and conjugated SA, or total SA, concentrations over time.

One half of each treated leaf was excised and weighed (one leaf half per plant; two plants per time point). Sampling was conducted over a 48 hour timeline (O, 1, 3, 6, 8, 24, 30 and 48 hours). The free and conjugated (2-o-β-D-glucosylsalicylic acid) SA was extracted as described by Verberne et al (2002) with the following modifications. Instead of being ground in liquid nitrogen, fresh leaf samples were ground directly in methanol using a glass tissue macerator. Additionally, the samples were dried by blow down under air, instead of in a SpeedVac (company, location) concentrator. These experiments were repeated on three independent occasions.

High Pressure Liquid Chromatography Determination of Salicylic Acid Concentration Dry samples were dissolved in absolute methanol (0.5 ml) and filtered through a 0.45 IJm nylon filter (Supelco, Bellefonte, PAL Acetic acid (0.5 ml of 1.2% v/v) was added and the sample was filtered a second time using a 0.45 IJm nylon filter. Sample (50 ul) was injected onto a Supercosil LC-18 HPLC column (250×4.6 mm, Sigma, St. Louis, Mo.) equipped with a C-18 guard column (7.5×4.6 mm, Alltech, Deerfield, Ill.). Elution was isocratic using 1:1 methanol to 1.2% v/v aqueous acetic acid at 0.8 ml/min. Under these conditions, SA had a retention time of 9.6 min at room temperature. Detection was performed using a Model L-4500A diode array detector (Hitachi, Tokyo, Japan). Integration of the salicylic acid peak was performed at 240 nm. A standard curve was developed based on integration values of salicylic acid in 1:1 methanol to 1.2% aqueous acetic acid (0.25-10.0 ug/ml).

Determination of Percent Recovery, for Salicylic Acid

To determine the amount of salicylic acid lost during extraction, several untreated leaf samples (2/SA concentration) were spiked with SA (0, 10, 100 and 200 mg) dissolved in 100% methanol. The samples were ground and SA was extracted as described above. The percent of recoverable SA was determined by comparing the integration values obtained by HPLC to a standard curve developed for SA. The experiment was repeated on two independent occasions.

Protein Extraction and Electrophoresis

To examine activation of NPR1, total protein was extracted from sugar beet leaf tissue at 2 days post treatment with ASM, live and dead BmJ, 203-7, BMH5E-33, SA and water using a plant fractionated protein extraction kit (Sigma, St. Louis, Mo.) according to the manufacturer's recommendations. Additionally, total protein was extracted from Live BmJ-treated tissue over an expanded 48 hour timeline (0, 0.5, 3, 6, 8, 24, and 48 hours). Protein concentration was determined by Bradford assay (BioRad) in comparison with bovine serum albumin standards (0-20 mM). Proteins (100 mg/sample) were heated to 60° C. for 10 min in sample loading buffer (125 mM Tris-HCl, pH 6.8, 5% SDS, 25% glycerol and 0.4% bromphenol blue). When the samples were to be reduced, 50 mM Dithiothreitol (DTT) was added to the sample loading buffer. Proteins were resolved (12% SDS-polyacrylamide gel electrophoresis (PAGE) gel) for 45 min (200 V) at pH 8.3 using molecular standards (BioRAD) for molecular weight determination. Both sets of experiments were replicated three independent times.

Western Analysis

Following electrophoresis, proteins were transferred to polyvinylidene fluoride membranes (BioRad) for 1 hour (100 V) in 25 mM Tris, 192 mM glycine and 20% (v/v) methanol (pH 8.3) using a BioRad mini-blot apparatus according to the manufacturer's recommendations. Membranes were blocked with 3% BSA for 1 hour, incubated in primary anti-*Arabidopsis* NPR1 antibody (Provided by Dr. Xinnian Dong, Duke University, Durham, N.C.; Mou et al, 2003, diluted 1:15,000) overnight at 4° C., followed by incubation in peroxidase-conjugated goat-anti-rabbit secondary antibody (BioRad, diluted 1:10,000) for 1 hour at room temperature. Colorimetric detection was performed using the 3-amino-9-ethylcarbazole (AEC) staining kit (Sigma, St. Louis, Mo.).

Results—Salicylic Acid

BmJ and 203-7 both elicit systemic resistance independent of SA accumulation. Over a 48 hour sampling scheme no statistical increases were noted between total SA levels at time zero and other time points in the Bacilli-treated leaves. The trend for SA levels was the same for water- and BMH5E-33-treated leaves. As shown in FIG. 1, at several later time points (6, 8, 30 and 48 hours post treatment), 203-7-treated leaves had a statistically significant decrease in SA levels.

Figure 2:
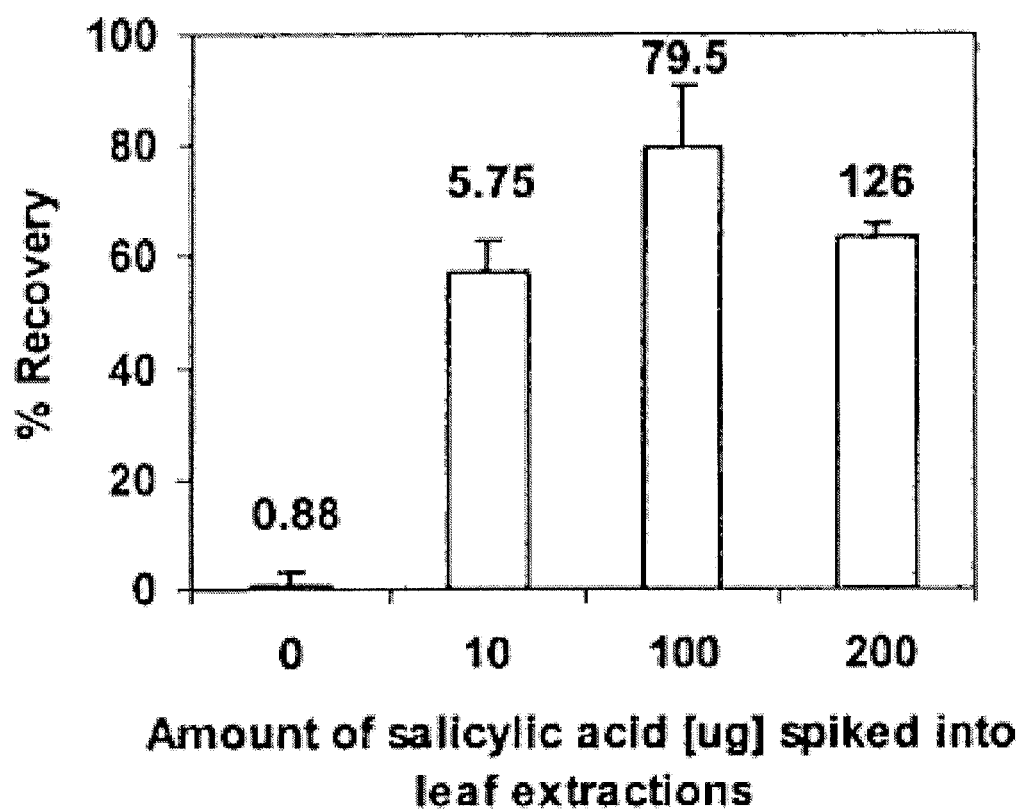

Determination of Percent Recovery for Salicylic Acid. Salicylic acid extraction methods provide notoriously poor recovery rates. Therefore, it was important to determine the amount of SA lost during the current extraction procedure. In the current experiment, recovery of spiked SA ranged from 57 to 79 percent. As seen with the unspiked samples, the total SA level is not at zero under basal conditions as shown in FIG. 2.

Results—NPR1

Figure 3:
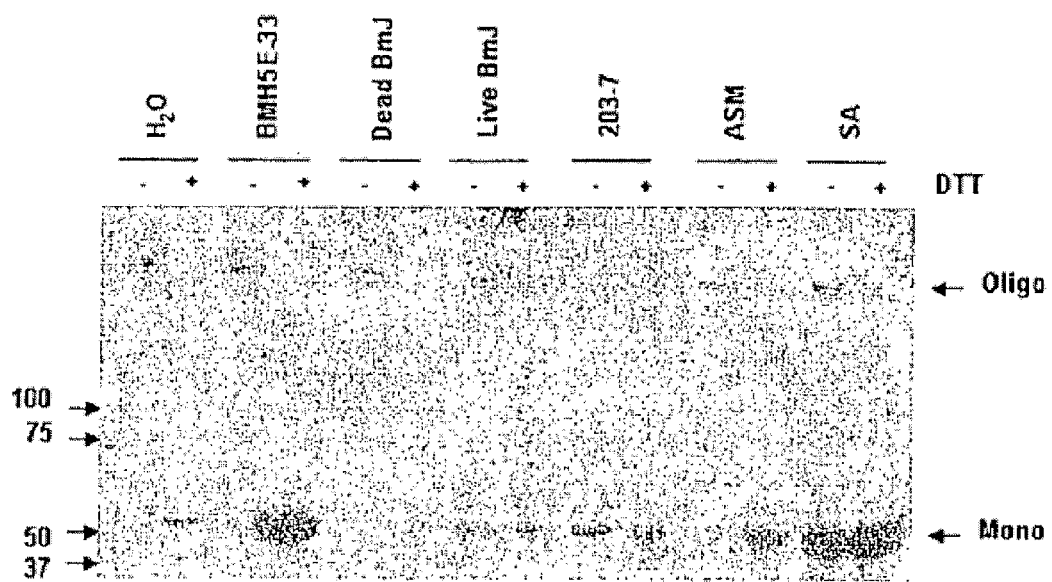

Only the inducers of resistance, live BmJ, 203-7, SA and ASM, activated NPR1 by 48 hours. Our negative controls, water and BMH5E-33, did not elicit reduction of the NPR1 oligomeric complex. However, it is shown in FIG. 3 that the NPR1 monomer could be "forcibly" released through addition of OTT, a reducing agent, in the loading buffer. When examining NPR1 activation following BmJ treatment over an expanded timeline, the monomeric form was first detectable at 3 hours post treatment and remained active through 48 hours of sampling.

Prior accounts have shown NPR1 is activated early in plant defense and remains active at least through 48 hours post elicitation, therefore NPR1 monomerization was examined at 2 days post treatment with live and dead BmJ, ASM, 203-7, BMH5E-33, SA and water.

Discussion

Summary.

Both BCAs elicit systemic resistance independent of SA accumulation, since there was no statistical increase in SA level in sugar beet leaf tissue over a 48 hour timeline following treatment with BmJ or 203-7. Additionally, the SA trend over time was similar to that observed following water and *Bacillus* pumulis isolate BMH5E-33 (BMH5E-33) treatment, an experimental and biological negative control respectively.

This would indicate the involvement of a novel secondary signaling component or activation of the signal transduction cascade downstream of SA accumulation. The latter is similar to acibenzolar-S-methyl activation of sugar beet systemic resistance which is SA-independent but NPR1-dependent. Without being limited by theory, we initially thought that both BmJ and 203-7 BCAs may activate NPR1, a protein associated with transcriptional activation of pathogensis-related genes. NPR1 was activated by 3 hours post treatment with BmJ in expanded sampling timelines. This timing of activation corresponds to the conclusion of the secondary hydrogen peroxide burst elicited by BmJ. The information obtained in this current investigation has allowed for further development of a working model for understanding signaling in BmJ- and 203-7-induced resistance in sugar beet.

No SA Accumulation.

Surprisingly, SA accumulation in sugar beet following BCA treatment was absent. As shown in FIG. 2, there was no statistical difference in SA level over time following BmJ treatment and the overall trend for SA was similar to that following water or BMH5E-33 treatment, both of which are negative controls.

Salicylic acid levels in SA-dependent resistance have been reported to rise as much as 15-fold over the basal level following resistance elicitation. Without being limited by theory, it is unlikely the current extraction or detection method are responsible for a failure to uncover a response of this magnitude, especially when we have observed 57-79% recovery of free SA spiked into samples prior to extraction, as shown in FIG. 1. Additionally, when testing for SA accumulation in sugar beet using a chemical positive control that activates SAR upstream of SA (probenazole, Yoshioka et al, 2001), there was a trend towards increased total SA levels over time (data not shown).

Interestingly, 203-7 treatment, which elicits similar biochemical responses from beet as BmJ, alternately led to a statistically significant decrease in SA levels over time, as shown in FIG. 2. However we do not consider this to be of biological significance since the change is so nominal.

Acibenzolar-S-methyl ("ASM"), a functional analog of SA (Tally et al, 1999; Lawton et al, 1996), activates the signal transduction cascade downstream of SA production which has been demonstrated using nahG plants (Chandra-Shekara et al, 2004). Therefore, the lack of SA accumulation following ASM application was expected.

NPR1 likely has role in SeA-induced resistance. Both BCAs in this study elicit an oxidative burst and PR-protein production in sugar beet, the activator and result of NPR1 monomerization respectively. Therefore a role for NPR1 in BCA-induced resistance seems likely. Other reports have shown NPR1 is activated early in plant defense and remains active through 48 hours post treatment (Mou et al, 2003) All of our inducing treatments, SA, ASM, live BmJ and 203-7, activated NPR1 by 2 days post application. On the other hand, water, dead BmJ and BMH5E-33, non-inducers, did not activate NPR1 at the time points examined, as seen in FIG. 3. None of the plants had any monomeric NPR1 present at time zero, which immediately proceeded application of our various treatments (data not shown). The antibody used in this study detected both the oligo- and monomeric forms of the protein. Live BmJ, ASM, SA and 203-7 treatment lead to partial reduction of the protein complex. Addition of on, a reducing agent, fully reduced the oligomer. Furthermore, the multimer of NPR1 was detected in the water-, dead BmJ- and BMH5E-33-treated samples, as would be expected of a constitutively expressed protein. Addition of on, in these cases as well, lead to full reduction of NPR1 into a monomeric state. Interestingly, in *Arabidopsis* this particular antibody only detects monomeric NPR1 (Mou et al, 2003).

Without being limited by theory, we initially thought that Bacilli BCA-induced resistance appears to be SA-independent but NPR1-dependent leads to two hypotheses: 1) Bacilli-induced resistance activates the SA-dependent signaling cascade downstream of SA, or 2) SAR is activated through reliance on a novel signaling compound. The former is similar to what is observed with several chemical inducers, such as ASM, 2,6-dichloroisonicotinic acid (Nakashita et al, 2002) and N-cyanomethyl-2-chloroisonicotinamide (yasuda et al, 2003). Salicylic acid does not directly activate NPR1; activation is achieved through an intermediate. Since NPR1 is activated by 3 hours following BmJ treatment, which corresponds to the peak of the secondary oxidative burst (Bargabus et al, 2003), this intermediate factor may be activated through peripheral OXB-associated responses, bypassing the need for SA accumulation.

Pathogenesis-related proteins induced by BmJ and 203-7 are associated with a typical SA-reliant pathway which is antagonistic towards JA-dependent defense (Felton and Korth, 2000; Gupta et al, 2000). Therefore, without being limited by theory, we initially thought that a novel signal, other than JA-ethylene, seems more likely deployed by these BCAs based on the Example 13. Other accounts of signaling components associated with Bacilli-induced resistance do not reach a congruent conclusion. Ryu et al (2004a) showed an isolate of *Bacillus pumulis* induced SA-independent resistance in *Arabidopsis* effective against Cucumber mosaic virus. Another BCA in the study, *Serattia marcescens*, activated a JA-dependent NPR1-independent pathway. However, *B. pumulis* dependence on JA and NPR1 was not discussed. In a separate study, Ryu et al (2004b) showed that an isolate of *Bacillus subtilis* induced systemic resistance through ethylene-dependent pathways completely independent of both SA and JA. Yet another isolate of *B. subtilis*, when tested on cucumber and tomato, induced resistance associated with differential accumulation of plant transcripts distinct from classical SA or JA associated SAR markers (Ongena et al, 2004). Again without being limited by theory, perhaps this is evidence of a novel BCA signaling cascade and defense response. Adding to the complexity, *B. amyloliquefaciens* induced NPR1-dependent resistance associated with both SA- and JA-dependent defenses (Anh et al, 2002). Interestingly, in pathogen-elicited defense, NPR1, when triggered through SA-dependent channels, represses JA-associated protein production (Spoel et al, 2003). This demonstrates that BCA activation of NPR1 has a different outcome altogether than pathogen activation, which may suggest involvement of novel signaling component. Whether BmJ and/or 203-7 elicit production of jasmonate-associated proteins has not been investigated based on the presumed universal antagonism between SA and JA. The fact that some BCAs are able to concordantly induce these normally inhibitory pathways provides additional credence to the idea that a unique signal is being produced that does not impart negative regulation on either subset of JA or SA associated genes.

Figure 4:
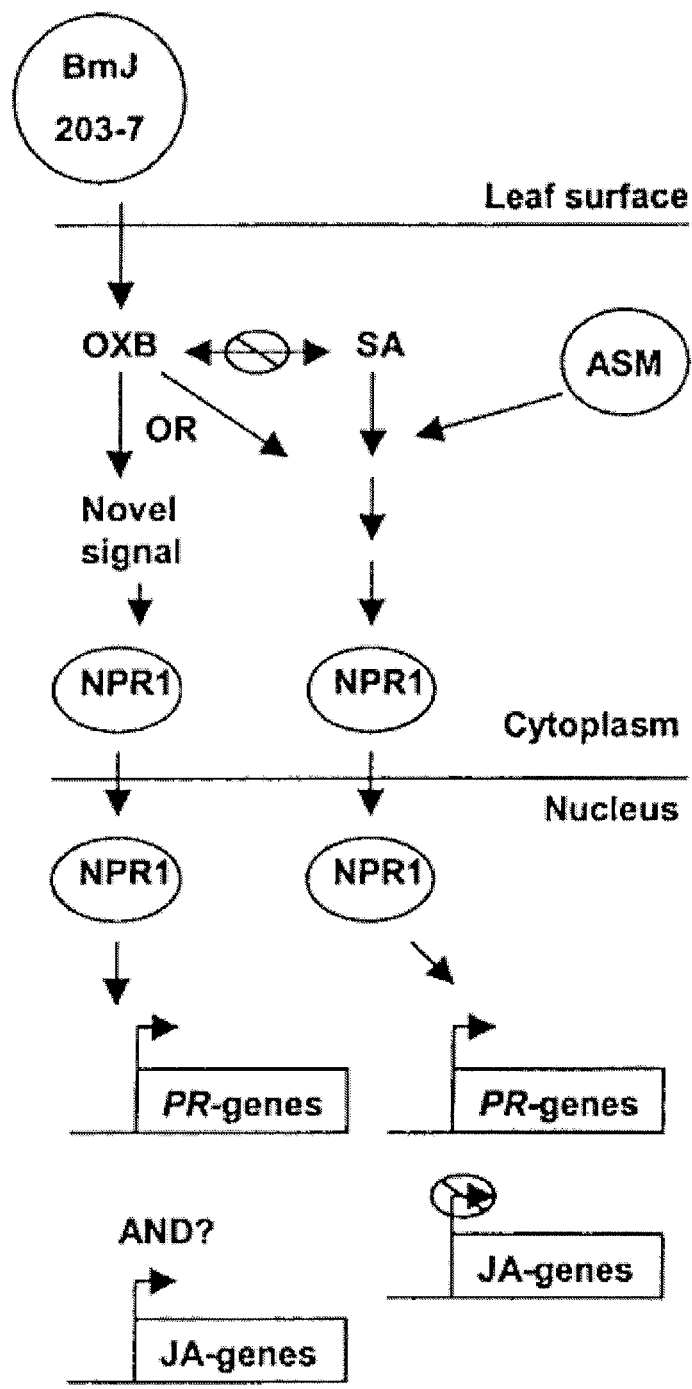

The information gathered in this current investigation has allowed for further expansion of our BCA-sugar beet interaction model, as shown in FIG. 4.

Example 14

Defense Pathways Activated by *Bacillus mojavensis* Isolate 203-7 and *B. Mycoides* Isolate BmJ as Elucidated by *Arabidopsis* Mutants Bacterial Cultures:
*B. mycoides* isolate BmJ (BmJ) was originally isolated from sugar beet leaves. *B. mojavensis* isolate 203-7 (203-7) originally isolated from sugar beet seed embryos was included in the greenhouse experiments since it showed good induction of SAR in previous experiments (Bargabus et al., 2004). Bacteria were cultured in 3% TSB for 24 hr at 22° C. on an orbital shaker at 250 rpm. Fresh cells were harvested by centrifugation for 20 min at 5,000 rpm at 4° C. The pellet was re-suspended in sterile-distilled water and pelleted twice by centrifugation for 20 min at 5,000 rpm at 4° C. to assure that all fermentation beer was separated from the cells. The inoculum density was adjusted to 108 colony forming units (CFU)/ml with distilled water and was applied using an aerosol sprayer with applications made to run-off.
Fungal Culture:
*Botrytis cinerea* isolate Bot-I was originally isolated from infected plant material and conidia were stored at −80° C. Conidia were streaked onto 50% potato dextrose agar using a sterile loop and incubated at 24° C. for 2 weeks. Plates were flooded with a solution consisting of 6.2 mM KH2P04 and 5.5 mM glucose in sterile-distilled water and conidia were loosen with a sterile glass rod. Conidia suspension was decanted and filtered through two layers of cheesecloth to remove mycelium and agar pieces. The inoculum density was adjusted to 105 conidia/ml.
*Arabidopsis Thaliana* Wild Type and Mutants.
*Arabidopsis thaliana* ecotype Columbia (Col-O) was received from Dr. Robert Sharrock, Montana State University. Following *Arabidopsis thaliana* mutants were obtained from the TAIR stock center and had a Col-O backround: ein2-1 (TAIR CS3071, ethylene insensitive), jarl-1 (TAIR CS8072, jasmonate resistance), ndrl-1/nprl-2 (TAIR CS6355, nonexpresser of PR genes and salicylic acid insensitive), and nprl-5 (TAIR CS3724, nonexpresser of PR genes and salicylic acid insensitive). The NahG mutant was obtained from Dr. Bob Dietrich, Syngenta, N.C.
Chemical Inducers:
Acibenzolar-s-methyl (ASM) (Actigard 50WG Fungicide, Syngenta, Greensboro, N.C.) as used as the chemical inducer for Col-O and NahG plants at a rate of 50 ug/ml of sterile distilled water. Probenazole (PBZ) (Chem Service, West Chester, Pa.) was used for npr1-5 mutants at a rate of 2 mM PBZ suspended in 0.1 M potassium phosphate buffer with 0.01% trition X-I 00. jar1-1 plants were treated with methyl jasmonate (MeJa) (TCI America, Portland, Oreg.) at a rate of 7.5 mM in 0.8% ethanol. 1 mM of 2-chloroethylphosphonic acid (Ethephon, Acros Organics, N.J.) dissolved in sterile-distilled water was the chemical inducer for ein2-1. All chemical inducers were applied using an aerosol sprayer with applications made to run-off.
Plant Culture, Treatments, Inoculation and Data Analysis:
*Arabidopsis* seeds were sown in flats containing Sunshine #1 mix (Sun Gro Horticulture Inc., Bellevue, Wash.) and vernalized for 4 days at 5±2° C. under 80% relative humidity (rh). They were then transferred to a growth chamber, sub-irrigated and kept at 22±2° C. day and 20 2° C. night temperature with a 10 hr photoperiod. After 3 weeks, individual plants were transplanted into plastic pots filled with Sunshine #1 mix supplemented with Osmocote Classic 14-14-14 (The Scotts Company, Marysville, Ohio) at a rate of 1.5 kg/m3 of Sunshine #1 mix. After 3 weeks, plants were induced either with distilled water, buffer, 203-7, BmJ, or the mutant specific chemical inducer by spraying the whole plant. After 6 days, plants were challenge inoculated with Bot-1 conidia solution by placing one 5 Jll droplet on 3 individual leaves per plant. Following inoculation, plants were placed at conditions as described above and under 90% rh for 7 days to allow disease development. Disease severity was rated at a 0 to 5 scale with 0=no visible lesion to 5=lesion expanding into non-inoculated tissue. The experimental design was a randomized complete block with 20 replications per treatment for the *Botrytis cinerea*-bioassay and 8 replications per treatment for the PR-protein assays. Experiments were repeated three times. Data were analyzed statistically by conducting an analysis of variance using the general linear model procedure of the SAS program (SAS system, Version 9.00, SAS Institute Inc., Cary, N.C.). The treatment means were separated using Fisher's protected least significant difference test at P=0.05.
Apoplastic Fluid Extraction and Protein Quantification:
Apoplastic fluids were done as described by Klement, 1965. Protein amount of apoplastic fluids was quantified using Bio-Rad protein assay kit (Bio-Rad, Hercules, Calif.) per manufacturer's instructions using bovine serum albumin (EMD Chemicals Inc., Darmstadt, Germany) as standards.
Chitinase, p-Glucanase and Superoxide Dismutase Assays:
Chitinase activity in apoplastic fluids was assayed as described by Hung et al. (2002). The microplate-based carboxymethylcellulose assay described by Xiao et al. (2005) was adapted to determine β-glucanase activity in apoplastic fluids. Quantification of superoxide dismutase (SOD) activity in the apoplastic fluid samples was performed according to the method described by Ewing and Janero (1995).
Results and Discussion:
Effects of the two BCAs and chemical inducers on disease reduction are shown in Table I. For all tested *Arabidopsis* lines (Col-O and mutants), the bacilli treatments and the chemical inducers were always significantly different (P=0.05) to the control plants treated with distilled water except for BmJ in ein2-1 mutants. Plants treated with the buffer controls alone were also significantly different to the control plants but had overall the lowest disease reduction when compared to the other treatments. Col-O plants treated with BmJ were not significantly different (P=0.05) from plants treated with Actigard or 203-7. Plants treated with 203-7 showed a significant (P=0.05) disease reduction in nprl-1, NahG, and ein2-1 mutants when compared to the specific chemical inducers, but were not significantly different to PBZ in the ndrl-1/nprl-2 mutant or to BmJ treated NahG mutants. Jarl-1 mutants treated with either 203-7 or BmJ showed the lowest (P=0.05) disease reduction when compared to methyl jasmonate and were never significantly different (P=0.05) to each other or to plants treated with buffer. Applications with BmJ resulted in the lowest (P=0.05) disease reduction in ein2-1 mutants and in a decreased disease reduction similar (P=0.05) to buffer in nprl-5 mutants. These results confirm the work done in sugar beet (Bargabus-Larson and Jacobsen, 2007) that induction by BmJ is salicylic acid independent and both NPR1 dependent. Further it demonstrates that BmJ induction involves jasmonic acid/ethylene signaling. It also demonstrates that induction by 203-7 is jasmonic acid signaling dependent and NPR1 independent.

TABLE 6

Percent disease reduction of Botrytis cinerea leaf spot on *Arabidopsis thaliana* Col-O and Col-O mutants by means of induced SAR resulting from foliar applications of *Bacillus mojavensis* isolate 203-7, *B. mycoides* isolate BmJ or chemical inducer.

| Mutant | % disease reduction in comparison to distilled water | | | | |
|---|---|---|---|---|---|
| Treatment | Col-0 | npr-5 | jar1-1 | NahG | ein2-1 |
| 203-7 | 38.4 B[a] | 52.4 d | 13.0 bc | 49.5 c | 36.8 c |
| BmJ | 41.3 bc | 9.9 b | 15.0 c | 49.5 c | 4.2 a |
| chemical inducer | 45.9 C (Actigard) | 41.9 c (PBZ) | 49.9 d (methyl jasmonate) | 32.6 b (Actigard) | 28.1 b (ethephon) |
| buffer | na | 7.9 b | 10.2 bc | na | na |
| distilled water | 0 a | 0 a | 0 a | 0 a | 0 a | a means in the same column followed by the same letter are not significant different according to Fisher's protected LSD (P = 0.05).

Wild type plants induced with BmJ and 203-7 had increased levels of chitinase (P=0.05) when compared to water controls while on ein2-1 mutants BmJ treatment did not increase chitinase levels. Chitinase levels in 203-7 induced wild type plants were equivalent to those induced with ASM but were not increased injar1-1 mutants (P=0.05). BmJ did not increase p-glucanase activity in either wild type or mutant plants while 203-7 increased p-glucanase in wild type, nprl-5, NahG and ein2-1 mutants but notjar1-1 mutants (P=0.05). Both BmJ and 203-7 increased SOD activity in wild type plants (P=0.05). BmJ treatment did not increase SOD activity in npr1-5 or ein2-1 mutants. 203-7 induction resulted in increased levels of SOD in nprl-5, NahG and ein2-1 mutants (P=0.05). These results demonstrate that PR and SOD activity are induced where jasmonic acid signaling is required by 203-7 and that ethylene signaling is involved in PR and SOD activity increases in plants induced by BmJ. These results also demonstrate that our current classifications of SAR and ISR do not work for BmJ or 203-7 BCAs and that there is considerable crosstalk occurring between plant defense signaling systems in plants.

Example 15

Evaluation of Control on *Fusarium* Crown Rot by Induction of Systemic Acquired Resistance by *Bacillus mycoides* Isolate J and Acbenzolar-S-Methyl Ester in Five Spring Wheat Cultivars Preparation of Plant Material The spring wheat cultivars Utopia (*Triticum durum*), Hank, Volt, MT0550, and Knudsen were used. Previously to seeding, the seeds were disinfected for 1 min with 10% sodium hypochloride and rinsed twice with sterile distilled water. Seeds were air dried for 3 hours in a fume hood. Pots (10 cm) with a capacity of 400 g of pasteurized MSU soil mix were used and four seeds were placed equidistant and at 2.0 cm of deep.

Inoculation Procedure.

Pots were inoculated 15 days post planting (dpp) with macroconidia of *Fusarium culmorum* isolate 2279 using a perforated microcentrifuge tube inserted in the center of the pot soil and equidistant of the emerged plants (FIG. 2). The soil inoculation was done by applying a suspension of spores of 1.0×106 macroconidia suspended in 20 mL of distilled water with a pipette. Macroconidia were obtained by growing fungus in Mung bean media for 10 days. The media was filtered through cheese cloth and the number of macroconidia was determined by counting using a hemacytometer.

Application of Inducers

Cultivars were sprayed with both inducers and a water control. Defenses were chemically activated by spraying plants with four leaves 3 days before inoculation. A suspension of ddH20 with 0.01% Tween 20 containing BmJ at 1.5×108 CFU per ml, 1.0 mM ASM (commercial formulation Actigard, Syngenta) solution, or only water were sprayed on the cultivars. All plants were sprayed until runoff (~1.7 mL per plant) and maintained separated inside of the glasshouse by 2 h until foliage were dry. Sprayings were repeated at 19, 26 and 33 days post planting. Plants were grown until Feekes stage 11 and during this time pots were maintained on trays and watered by infiltration each two days with 4 liters of water per 18 pots. Fertilizer was applied weekly as needed.

Disease Assessment

Treatments were randomized on each cultivar. FCR severity was determined by using a crown rot rating (CRR) scale of 1 to 4 on the first internode of each plant, whereby: 1=0-5%; 2=5-50%; 3=50-85%; and 4=85-100% internode discoloration. A disease severity index (DSI) was determined by summing the individual CRRs and dividing this for the possible maximum value of infection and multiplying by 100 to create a DSI percentage for each pot.

Data Analysis

Each SAR inducer treatment was assessed individually with a randomized design and inducer treatments and cultivars were considered as factors in a factorial analysis. ANOVA were performed by the SAS procedure, Proc GLM (Version 8.0, Inc. Cary, N.C., USA). Least significant difference (LSD) range test was used to compare means ($\alpha$<0.05).

Results

The results are shown in Table 7. Analysis of the level of control of the biological and chemical inducers showed statistical differences for disease severity for cultivar (P=0.0003) and for treatment (P=0.03) but no cultivar x treatment interactions (P=0.17) were detected. Over all treatments, the cultivars Knudsen and Volt were less susceptible than Utopia and MT 0550 while Hank was more susceptible than Volt but equivalent to Knudsen (P=0.0003). Knudsen and Volt are *Fusarium* head blight (FHB) resistant cultivars, and the resistance to FHB has been associated with the induction of different PR-proteins (Pritsch, et al., 2000). Knudsen is a cultivar derived from the FHB resistant genome Sumai 3, which has showed that chitinases and β-1,3-glucanases are accumulated faster (Pritsch, et al., 2000). Analysis for each cultivar showed BmJ reduced FCR severity only on the most resistant cultivar, Volt (P=0.05). These results suggest the potential to use BmJ with cultivar resistance for control of FCR, which could be improved if this inducer is incorporated to an Integrated Pest Management with a fungicide seed treatment. ASM reduced FCR severity only on MT 0550 (P=0.02), but over all cultivars, ASM reduced FCR severity significantly from the water control while BmJ was intermediate (P=0.03).

TABLE 7

Control on *Fusarium* crown rot by *Bacillus mycoides* Isolate J and
Acbenzolar-S-methyl ester in five spring wheat cultivars Cultivars
Disease Severity Index (%)

| Treatments | Utopia | Knudsen | MT 0550 | Hank | Volt | Average |
|---|---|---|---|---|---|---|
| Control | 67.38 | 47.95 | 69.47 a | 54.88 | 50.02 a | 57.94 a |
| BmJ | 55.92 | 49.33 | 71.88 a | 51.07 | 33.70 b | 52.38 ab |
| ASM | 60.43 | 46.88 | 42.73 b | 48.97 | 37.53 ab | 47.31 b |
| Average | 61.24 a | 48.06 bc | 61.36 a | 51.64 ab | 40.42 c | P Trt = 0.0325 |
| P-value of e/cvs. | 0.5647 | 0.966 | 0.022 | 0.7021 | 0.0506 | P cvs = 0.0003 |
| | | | Interaction Cvs × Trt P-value = | | | 0.1703 |

Example 16

Control of Early Blight in Potatoes by BmJ

Field experiments assessing BmJ for control of early blight (*Alternaria solani*) in potatoes were conducted at Idaho. BmJ spores were applied at a rate of 62.5 grams per 50 gallons of water per acre in four applications at 14 day intervals. In treatment 3, Headline (Commercial strobilurin fungicide manufactured by BASF, chemical name is pyraclostrobin) was applied in the first application followed by three applications of BmJ at 14 day intervals. In treatment 4 BmJ was applied first and alternated with headline at 14 day intervals. The trial was a random block design with four replicate plots per treatment. Ratings of leaf area damage were made using standard rating methods and evaluated using standard statistical techniques.

TABLE 8

BmJ Potato Early Blight Trial, Idaho

| | Treatment | Rate | Damage Rating |
|---|---|---|---|
| 1 | Untreated Check | | 20 a |
| 2 | BmJ spores ($3 \times 10^{10}$ per gram) | 130 gram/acre | 10 b |
| 3 | HEADLINE PREFERENCE Then BmJ spores ($3 \times 10^{10}$ per gram) | 6 FL OZ/A 0.25% V/V 130 gram/acre | 13 ab |
| 4 | HEADLINE PREFERENCE Mix with BmJ spores ($3 \times 10^{10}$ per gram) | 6 FL OZ/A 0.25% V/V 130 gram/acre | 6 b |
| 5 | HEADLINE PREFERENCE | 6 FL OZ/A 0.25% V/V | 10 b |

TABLE 8-continued

BmJ Potato Early Blight Trial, Idaho

| Treatment | Rate | Damage Rating |
|---|---|---|
| LSD (P = .05) | | 8.6 |
| Standard Deviation | | 5.6 |

Trt. 3. Headline followed by BmJ;
Trt. 4. Headline mixed with BmJ
Values followed by the same letter are not significantly different BmJ alone provided statistically significant reduction in foliage damage compared to untreated controls and was equivalent to Headline. The alternation of BmJ and Headline provided the best numerical result but was not statistically different than BmJ or Headline alone.

Example 17

Control of White Mold in Potatoes by BmJ

*Sclerotinia* white mold is a worldwide, economically important disease in many crops. BmJ was tested for control of white mold disease in potatoes caused by the fungus *Sclerotinia sclerotiorum*. Trials were conducted in Idaho and Montana.

Idaho Trial 1

A field experiment assessing BmJ for control of early blight and white mold (*Sclerotinia sclerotiorum*) was conducted in Rupert, Id. BmJ spores ($3 \times 10^{10}$ per gram) were evaluated in two treatments, a high rate of 250 grams per acre and half the rate of 31 grams/acre used in the previous early blight trial. This test used Western Russet, a susceptible variety, with three applications at two week intervals. Trial was a random block design with four replicate plots for each treatment. Disease ratings and statistical analysis were made using standard techniques with BmJ treatments compared to a standard treatment of a mixture of two chemical fungicides, Dithane and Quadris.

TABLE 9

Potato Early Blight, White Mold Trial

| | Description | | | | |
|---|---|---|---|---|---|
| | % Early Blight | | | # White mold hits | |
| | Rating Date | | | | |
| | Jul 24 | Aug 17 | Aug 28 | Aug 17 | Aug 28 |
| | Rating Unit | | | | |
| Treatment | % | % | % | NUMBER | NUMBER |
| 1 Untreated Check | 4 a | 45 a | 63 a | 2.0 a | 17 a |
| 2 QUADRIS DITHANE | 1 a | 25 a | 48 a | 1.0 a | 12 b |

TABLE 9-continued

Potato Early Blight, White Mold Trial

| | Description | | | | |
|---|---|---|---|---|---|
| | % Early Blight | | | # White mold hits | |
| | Rating Date | | | | |
| | Jul 24 | Aug 17 | Aug 28 | Aug 17 | Aug 28 |
| | | | Rating Unit | | |
| Treatment | % | % | % | NUMBER | NUMBER |
| 3 BmJ spores ($3 \times 10^{10}$ per gram) 250 g | 1 a | 35 a | 58 a | 2.5 a | 11 b |
| 4 BmJ spores ($3 \times 10^{10}$ per gram) 31 g | 2 a | 41 a | 60 a | 2.5 a | 12 b |
| LSD (P = .10) | 3.5 | 19.1 | 28.3 | 1.90 | 3.9 |

Values followed by the same letter are not significantly different

In this trial early blight was severe and none of the treatments provided statistically significant control of early blight. However, ratings for white mold incidence showed significant control in the BmJ treatment, comparable to the chemical fungicide combination. Therefore, BmJ is effective in controlling white mold.

Idaho Trial 2

The trial was conducted in Aberdeen Id. to test different rates of BmJ spores in comparison with a program used in the region by growers, with other chemical fungicides and with BmJ following a single application of a chemical fungicide. All chemicals were applied at the rate recommended on the product label. Chemicals fungicide trade names, active ingredient and application rate used in the trial were:

ENDURA® (boscalid), active ingredient Boscalid. Use rate in grower standard treatment combination was equivalent to 270 grams active ingredient per hectare, alone or with the BmJ treatment 385 grams/ha. Endura is a newer chemical introduced in potatoes for disease control. The combination of Endura followed by BmJ was to evaluate potential for controlling development of resistance to Endura by the pathogen.

HEADLINE® (strobilurin), a strobilurin fungicide containing the active ingredient, Pyraclostrobin. Applied at a rate equivalent to 110 grams active ingredient per ha. Widely used for disease control in potatoes.

DITHANE® (Mancozeb) a carbamate fungicide containing the active ingredient, Mancozeb. Applied at the rate of 1680 grams active ingredient per ha. An older off patent chemical widely used for disease control in potatoes, often in programs with other newer less toxic chemicals to manage resistance development.

BRAVO ULTREX® (chlorothalonil) containing the active ingredient, Chlorothalonil. Applied at a rate equivalent to 1.52 kg formulation per ha. An older off patent chemical used for resistance management.

Grower standard was four applications: 1) Endura/Rivet; 2) Headline; 3) Endura Rivet; 4) Dithane.

Dithane alone and Bravo Ultrex were applied in three applications. Rivet is an insecticide included in the grower standard to control insects.

BmJ was applied in four applications. Three rates were tested 0.33 g/l, 0.66 g/l and 0.99 g/l of BmJ spores ($3 \times 10^{10}$ per gram) in water. The BmJ/Endura treatment was a single Endura application followed by three BmJ applications at the rate of 0.66 g/l of BmJ spores ($3 \times 10^{10}$ per gram). The three rates of BmJ spores are approximately equivalent to the application of 69, 138 or 207 grams of BmJ spores, in 190 liter of water per ha.

Four replicate plots were sprayed for each different treatment. Disease incidence and severity was rated by the University of Idaho extension researcher using standard techniques for observation of white mold lesions. Results expressed as relative area under the disease progress curve are shown in the following table. All three rates of BmJ showed statistically significant reduction in disease with the 0.99 g/l or three ounce/acre rate and the combination of Endura followed by BmJ spores showing control equivalent to the grower standard program currently in use.

TABLE 10

BmJ Potato White Mold Trial, Aberdeen Idaho

| Treatment | White Mold RAUDPC |
|---|---|
| Untreated | 5.7 a |
| Grower Std | 0.1 d |
| BmJ spores ($3 \times 10^{10}$ per gram) 0.33 g/l | 3.2 ab |
| BmJ spores ($3 \times 10^{10}$ per gram) 0.66 g/l | 2.5 bcd |
| BmJ spores ($3 \times 10^{10}$ per gram) 0.99 g/l | 0.2 cd |
| BmJ spores ($3 \times 10^{10}$ per gram) 0.66 g/l Endura | 0 d |
| Dithane | 3.0 abc |
| Bravo Ultrex | 2.8 bcd |

Values followed by the same letter are not significantly different

Montana Trial

The trial in Montana compared two treatment regimes of BmJ spores with several different chemical fungicides used for disease control in potatoes. Chemicals fungicide trade names and active ingredient and application at recommended label rates of end use formulation in the trial were:

ECHO ZN® (chlorothalonil), active ingredient, Chlorothalonil. Application rate 2 pints per acre LUNA TRANQUILITY® (Fluopyram and Scala) A blend of two active ingredients, Fluopyram and Scala. Application rate 11 oz per acre BAS 700) 4F, 4.6 oz per acre, and BAS 703AG F 5.5 oz per acre. These are experimental fungicides being tested for disease control in potatoes, active ingredients are proprietary. Results are included for comparison with chemical fungicides under development for control of *Sclerotinia* white mold.

PROLINE® (triazolinthione) A triazolinthione fungicide, active ingredient, Prothioconazol. Application rate 5.7 oz/acre ENDURA® (boscalid), active ingredient boscalid as described above, 5.5 oz per acre.

BmJ spores ($3 \times 10^{10}$ per gram) were applied at a rate equivalent to one ounce in 20 gallons of water per acre.

The ECHO ZN® (chlorothalonil)/LUNA TRANQUILITY® (Fluopyram and Scala) and BmJ spores were tested in two different treatments with different application timing: 1) one application at 10% flower bloom; and 2) two applications, at 10% bloom followed by a second application 10 days later. Other chemical treatments were applied once at 10% bloom. All treatments were applied to four replicate plots. Disease ratings and harvest estimates were made by Montana State University extension researchers. Disease severity expressed as number of stem infection lesions in 10 row feet of plants and yield expressed as hundred weight per acre are shown in the following table.

Both BmJ treatments showed statistically significant reduction in disease with the two applications comparable to the chemical fungicide treatments. BmJ treated plots showed the highest yield, statistically superior to the untreated and equivalent to or greater than the chemical fungicide treatments.

TABLE 11

*Sclerotinia* Fungicide Treatment Results-
var. Russet Burbank-location Manhattan, Mt

| Treatment | Timing | Number of stem infections per 10 feet row | Yield/Acre CWT |
|---|---|---|---|
| 1. Untreated control | | 38.3 a | 190.8 |
| 2. Echo ZN Luna Tranquility | 10% bloom + 10 days | 2.8 c | 218.3 |
| 3. Echo ZN Luna Tranquility | 10% bloom | 5.5 c | 223.1 |
| 4. Endura | 10% bloom | 3.0 c | 219.4 |
| 5. BAS 700 04F | 10% bloom | 4.5 c | 230.8 |
| 6. BAS 703 AG F | 10% bloom | 16.8 b | 216.5 |
| 7. BMJ at 10% flower | 10% bloom | 19.5 b | 218.3 |
| 8. BMJ | 10% bloom + 10 days | 10.3 b c | 232.8 |
| 9. Proline at 5.7 oz/A | 10% bloom | 10.0 b c | 228.9 |
| Flsd 0.05 | | 11 | 14 |

Example 18

Control of Potato Virus Y by BmJ

In three repeated experiments using the potato cultivar Norkotah, induction of resistance with *Bacillus mycoides* isolate J (BmJ) prevented infection with PVY in three separate experiments; control was 38%, 100% and 50%—over 45 days post inoculation compared to check plants induced with either dead BmJ or water. Experiments were conducted in greenhouses. Replicate plants were treated with BmJ spores ($3 \times 10^{10}$ per gram) and applied 5 days before inoculation of the plants with potato virus Y. PVY infection was assessed by leaf damage ratings and by ELISA assays of leaf extract to determine virus titers.

Field trials in Oregon under natural infection conditions were inconclusive due to very low virus infection although numerically BmJ plants treated 4 times at 14 day intervals had 6% less PVY infection 30 days after emergence and 4% less infection 60 days after emergence.

Example 19

BmJ for Control of Bacterial Spot in Tomato Fla. Trial

The tomato trial was conducted in Jupiter, Fla. The trial was designed as a complete randomized block with four replicates per treatment. BmJ spores ($3\times10^{10}$ per gram) were applied to plants. Application volume was 30 to 75 gallons per acre, increasing as the plants grew. The agronomic system replicated commercial production using raised beds with plastic mulch and drip irrigation.

The trial was designed to be a comprehensive evaluation of BmJ testing preparations alone and in combination with chemical agents.

TABLE 12

Trial Design

| | Treatments | Rates | Application Dates* |
|---|---|---|---|
| 1. | Untreated Check | — | — |
| 2. | BmJ spores ($3\times10^{10}$ per gram) | .33 g/L | Day 2, 10, 17, 22, 28, 37, 41, 49, 56, 63, 70, and 77 |
| 3. | BmJ spores ($3\times10^{10}$ per gram) | .33 g/L | Day 2, 10, 17, 22, 28, 37, 41, 49, 56, 63, 70, and 77 |
| | Bravo WS Tank mix | 2.5 pts/A | |
| 4. | BmJ spores ($3\times10^{10}$ per gram) | .33 g/L | Day 2, 17, 28, 41, 56, 70 |
| | Bravo WS Alternate | 2.5 pts/A | Day 10, 22, 37, 49, 63, 77 |
| 5. | BmJ spores ($3\times10^{10}$ per gram) | .33 g/L | Day 2, 10, 17, 22, 28, 37, 41, 49, 56, 63, 70, and 77 |
| | Manex mix | 1.6 qt/A | |
| 6. | Kocide 2000 | 2 lb/A | Day 2, 17, 28, 41, 56, 70 |
| | Manex | 1.6 qt/A | |
| | Bravo WS | 2.5 pts/A | Day 10, 22, 37, 49, 63, 77 |

*The date when evaluations began was set as Day 1.

Naturally occurring bacterial spot remained low due to dry weather conditions until after the artificial inoculation with bacterial spot on Day 31. The trial was inoculated with *Xanthomonas campestris* infected tomato foliage from the Immokalee, Fla. area. This foliage was blended with 6 L of water and 1 ml of Silwet and sprayed out using a backpack carbon dioxide pressurized sprayer over the four plants at each end of each plot. To encourage bacterial disease development, overhead irrigation was placed in the trial on Day 37, and run 20-30 minutes/day except for 2 days following trial applications.

Active bacterial spot disease incidence and severity were evaluated from Day 1 to Day 84. Results are shown in the following tables in bold denote significant differences from the untreated control. BmJ combined or alternated with Bravo (Chlorthalonil) reduced disease incidence and severity on three to four rating dates compared to controls and was similar to a standard commercial treatment of Kocide (copper), Manex and Bravo. The combination of BmJ with Manex showed reduced disease incidence on four rating dates compared top three dates for the standard commercial treatment. The combination of BmJ and MANEX® (Manganese ethylenebisdithiocarbamate) showed reduced disease severity on six of the rating dates, equal to the standard treatment.

TABLE 13

BmJ Tomato Bacterial Spot, Florida Trial
Mean Percent Bacterial Spot Disease Incidence

| Treatment | Day 1 | Day 8 | Day 14 | Day 21 | Day 27 | Day 34 | Day 41 | Day 48 | Day 55 | Day 62 | Day 69 | Day 76 | Day 84 |
|---|---|---|---|---|---|---|---|---|---|---|---|---|---|
| Untreated | 0 | 0 | 0 | 0 | 3 | 70 | 23 | 55 | 28 | 65 | 100 | 100 | 100 |
| BmJ | 0 | 0 | 3 | 8 | 5 | 78 | 35 | 63 | 13 | 48 | 100 | 100 | 100 |
| BmJ/Bravo | 0 | 0 | 3 | 13 | 3 | 40 | 20 | 20 | 3 | 43 | 100 | 100 | 100 |
| BmJ/Bravo | 0 | 0 | 0 | 0 | 5 | 40 | 15 | 20 | 10 | 30 | 100 | 100 | 100 |
| BmJ/Manex | 0 | 0 | 8 | 0 | 0 | 30 | 13 | 20 | 3 | 18 | 100 | 100 | 100 |
| Kocide/Manex/Bravo | 0 | 0 | 0 | 3 | 3 | 35 | 23 | 25 | 3 | 0 | 100 | 100 | 100 |

TABLE 14

BmJ Tomato Bacterial Spot, Florida Trial
Mean Bacterial Spot Disease Severity

| Treatment | Day 1 | Day 8 | Day 14 | Day 21 | Day 27 | Day 34 | Day 41 | Day 48 | Day 55 | Day 62 | Day 69 | Day 76 | Day 84 |
|---|---|---|---|---|---|---|---|---|---|---|---|---|---|
| Untreated | 0 | 0 | 0 | 0 | 0 | 0.8 | 0.2 | 0.6 | 0.3 | 0.7 | 2.7 | 3.4 | 3.2 |
| BmJ | 0 | 0 | 0 | 0.1 | 0.1 | 0.8 | 0.4 | 0.6 | 0.1 | 0.5 | 2.1 | 3.0 | 2.8 |
| BmJ/Bravo | 0 | 0 | 0 | 0.1 | 0 | 0.4 | 0.2 | 0.2 | 0 | 0.4 | 2.9 | 2.8 | 2.5 |
| BmJ/Bravo | 0 | 0 | 0 | 0 | 0.1 | 0.4 | 0.2 | 0.2 | 0.1 | 0.3 | 2.4 | 2.7 | 2.6 |
| BmJ/Manex | 0 | 0 | 0.1 | 0 | 0 | 0.3 | 0.1 | 0.2 | 0 | 0.2 | 1.8 | 2.0 | 2.0 |
| Kocide/Manex/Bravo | 0 | 0 | 0 | 0 | 0 | 0.4 | 0.2 | 0.3 | 0 | 0 | 1.8 | 2.1 | 2.3 |

The results suggest BmJ is effective in controlling bacterial spot, and there are synergistic effects from a combination of BmJ with Bravo or Manex.

Example 20

BmJ for Control of Bacterial Spot in Peppers, Fla. Trial

BmJ was evaluated for control of bacterial spot (*Xanthomonas campestris*) in peppers at Belle Glade, Fla. The trial was conducted using BmJ spores ($3 \times 10^{10}$ per gram). The trial was designed as a random block with four replicate plots per treatment with four applications with treatments sprayed to runoff. BmJ was compared with standard chemical treatments and with the biological fungicide Serenade. Treatments and results are shown in the following table.

TABLE 15

BmJ Pepper Bacterial spot Florida
Bacterial Spot Disease Rating (foliar damage)

| Treatment | Feb 9 | Feb 12 |
|---|---|---|
| Untreated | 43 a | 49 a |
| Manzate/Cabrio | 16.3 bcd | 11.8 cd |
| Manzate/Kocide | 24.7 b | 18 cd |
| Serenade/Biotune | 22.7 bc | 25 b |
| Serenade/Cuprofix/Biotune | 12.5 d | 10.4 cd |
| BmJ | 15.3 cd | 19 cd |
| BmJ/Manzate | 12 d | 8.6 d |

Values followed by the same letter are not significantly different
BmJ was applied four times at 25 gram/acre ($3 \times 10^{10}$ spores/gram), and other products were application four times as label rates.
Note:
higher disease rating reflects more foliar damage from the disease This result was similar to the Florida tomato trial. BmJ alone provided some control, however the best treatment was the BmJ Manzate combination which was superior to the grower standard of Manzate/Kocide. BmJ was also significantly better than the competing biological Serenade both applied alone (Biotune is an adjuvant) and in combination with copper. The results suggest BmJ is effective in controlling bacterial spot, and there are synergistic effects from a combination of BmJ with Manzate.

Example 21

BmJ for Control of Gray Mold in Tomatoes

Two trials were conducted in greenhouse tomatoes to evaluate BmJ and 203-7 for control of gray mold, *Botrytis cinerea*. In these trials BmJ was compared to other biological agents. Serenade is a commercial product containing *Bacillus*

*subtilis* and T-22 is a commercial formulation of a strain of the fungus *Trichoderma harzianum*. The test was conducted using BmJ spores ($3 \times 10^{10}$ per gram).

In these trials the total amount of gray mold was light throughout and no stem cankers developed on plants receiving any of the treatments. However, all treatments had significantly less disease than the untreated pathogen control. In both trials BmJ treatment resulted in the least amount of disease when compared to all of the other treatments as shown in tables below. Plants treated with 203-7 and BmJ had the highest yield when compared to Serenade, but they were not significantly different from the pathogen control or T22 (P=0.05).

TABLE 16

Control of *Botrytis cinerea* in greenhouse tomatoes by biological products Trial 1

|  | Leaf Lesion Rating | Total Yield/rep (grams) |
| --- | --- | --- |
| 1. Pathogen Control | 1.48 | 5992.1 |
| 2. 203-7 | 0.87 | 6213.3 |
| 3. BmJ ($1 \times 10^7$ spores/ml) | 0.60 | 6213.1 |
| 4. Serenade | 0.82 | 5192.8 |
| 5. T22 | 0.81 | 5701.0 |
| $LSD_{(0.05)}$ | 0.18 | 979.1 |

TABLE 17

Control of *Botrytis cinerea* in greenhouse tomatoes by biological products Trial 2

|  | Leaf Lesion Rating | Total Yield/rep (grams) |
| --- | --- | --- |
| 1. Pathogen Control | 1.01 A | 4974 AB |
| 2. 203-7 | 0.608 B | 5285 A |
| 3. BmJ ($1 \times 10^7$ spores/ml) | 0.467 C | 5074 AB |
| 4. Serenade | 0.521 BC | 4244 B |
| 5. T22 | 0.635 B | 4671 AB |

Values followed by the same letter are not significantly different

Example 22

Foliar Application of BmJ and 203-7 for Control of Root Diseases in Geranium

A greenhouse trial was conducted to evaluate control of root diseases in ornamentals. In this trial geranium plants were treated by foliar application of BmJ spores ($3 \times 10^{10}$ per gram) or the *Bacillus* isolate 203-7, and after 5 days, transplanted into soil that was infested with the root rotting pathogen *Pythium aphanidermatum*. Treatment with BmJ significantly reduced stunting and root discoloration in plants that had been inoculated with the root rotting pathogen *Pythium aphanidermatum* when compared to the pathogen inoculated control. We believe that this is the first report of a foliar applied biocontrol agent reducing a disease caused by a soil-borne root pathogen.

TABLE 18

Effect of a foliar application of BmJ and 203-7 on root disease of geranium caused by *Pythium aphanidermatum*

|  | Stunting | Root Discoloration |
| --- | --- | --- |
| Untreated Control | 0.3b | 0.07b |
| Pathogen Control | 1.0a | 0.81a |
| BmJ ($1 \times 10^7$ spores/ml) | 0.4b | 0.15b |
| 203-7 | 1.1a | 0.15b |
| $LSD_{(0.05)}$ | 0.6 | 0.25 |

Values followed by the same letter are not significantly different

Example 23

BmJ for Control of Powdery Mildew in Cantaloupe (*Cucumis Melon*)

BmJ was evaluated for control of powdery mildew (*Podosphora xanthii*) in a field trial conducted at Yuma, Ariz. BmJ spores ($3 \times 10^{10}$ per gram) were applied at the rate of 25 grams per acre. The trial was a random block design with four replicate plots per treatments with leaf damage ratings made by standard techniques.

Treatments compared BmJ to a number of chemical and biological treatments. The trial rated powdery mildew on both the upper and lower leaf surface as some systemic treatments might provide improved control where coverage of contact material might be poor in dense foliage.

TABLE 19

BmJ - Cantaloupe Powdery Mildew Trial, Arizona Leaf Damage Rating

| Treatment | Upper Leaf | Lower Leaf |
| --- | --- | --- |
| Untreated | 3.7 | 4.5 |
| BmJ ($3 \times 10^{10}$ spores per gram) | 3.1 | 3.1 |
| Procure | 0.3 | 0.3 |
| Procure/BmJ | 0.1 | 0.2 |
| Serenade/Silwet | 2.6 | 3.6 |
| Sonata/Silwet | 2.6 | 3.7 |
| Silwet | 2.3 | 2.7 |
| LSD | 0.1 | 0.2 |

BmJ alone provided statistically significant control but much less than the chemical treatments. BmJ tank mixed with Procure did not provide increased control compared to Procure alone. Compared to Sonata and Serenade, the other biological products in the trial BmJ yielded less control on the upper leaf surface but greater control on lower leaf surface. However, these other biological products were applied with Silwet which provided comparable levels of disease control when applied alone. The BmJ treatments were applied in plain water.

Example 24

BmJ for Control of Downey Mildew in Squash

BmJ was evaluated for control of downey mildew caused by the fungus *Pseudoperonospora cubensis* in a field trial conducted at Belle Glade, Fla. BmJ spores ($3 \times 10^{10}$ per gram) were used. The trial evaluated BmJ alone and in combination with chemical fungicides. There were a total of nine weekly sprays. Plots were rated for downy mildew severity on May 4 and May 11. An estimate was made of the percentage of foliage covered by disease lesions and foliage lost to disease combined into one rating. Fruit were harvested from all 12 plants (22 ft of row) in each plot on May 18, counted, and weighed. Cucumber leaves with abundant, sporulating lesions of downy mildew were collected from a naturally infected cucumber field in Boynton Beach and spread in the guard rows (untreated) on the east side of the experimental plots on April 19. This inoculation and weather combined to create an explosive downy mildew experiment, resulting in severe foliar damage by harvest. The 11 treatments and results for this trial are shown in the following table.

TABLE 20

Efficacy of Foliar Sprays for Management of Downy Mildew of Winter Squash

| Treatment and rate/A[1] | Downy Mildew[2] | | Number of fruit harvested | Weight of fruit harvested (lb) |
|---|---|---|---|---|
| | May 4 | May 11 | | |
| Untreated (control) | 63 b | 87.3 a | 41.5 N.S.[4] | 31.9 N.S.[4] |
| Bmj (25 g/20 gal water) | 81.3 a | 83.3 ab | 49.3 | 32.1 |
| Bmj (25 g/20 gal water) + Cabrio (2 applications after disease appeared)(1 lb) | 59.5 bc | 77.8 abc | 53.3 | 36.8 |
| Sonata (2 qt) + Biotune (0.2 m/100 ml water) + Previcur (1 pt) alternated with Sonata (2 qt) + Biotune (0.2 m/100 ml water) + Nutri-Phyte (1 pt) | 53.3 bc | 75.8 abcd | 54.8 | 37.6 |
| Sonata (4 qt) + Biotune (0.2 ml/100 ml water) | 50 c | 73.3 abcd | 45.8 | 32.3 |
| Sonata (2 qt) + Biotune (0.2 m/100 ml water) + Previcur (1 pt) alternated with Sonata (2 qt) + Biotune (0.2 m/100 ml water) + Manzate 75 DF (1.5 lb) | 10.8 d | 59.5 cde | 57.0 | 36.2 |
| Previcur (1 qt) alternated with Bravo Weather Stik (1.5 qt) | 9.2 d | 41.3 e | 51.5 | 37.4 |
| Sonata (2 qt) + Biotune (0.2 m/100 ml water) + Previcur (1 pt) alternated with Bravo Weather Stik (1 qt) + Manzate 75 DF (1 qt) | 9 d | 54.5 de | 49.0 | 32.2 |
| Cabrio (12 oz) + Forum (6 oz) alternated with Previcur (1 qt) + Bravo Weather Stik (1.5 qt) | 8.8 d | 62.3 bcde | 48.0 | 28.8 |
| Bmj (25 g/20 gal water) + Bravo Weather Stik (1.5 qt) | 8.8 d | 50.7 e | 48.0 | 33.1 |
| Bmj (25 g/20 gal water) alternated with Bravo Weather Stik (1.5 qt) | 8.8 d | 45 e | 49.3 | 35.7 |

[1]Rates are formulation/acre.
[2]Ratings are estimates of percentage of foliage damaged by downy mildew May 4 and May 11. Adaxial surface used for downy mildew ratings. There were 9 spray dates March 16, 23, and 30, April 6, 13, 19 and 27, and May 4 and 11

Several treatments greatly reduced downy mildew severity. Bmj+Bravo Weather Stik as a weekly tank mix or alternated weekly were quite effective. The biological agents (BmJ and Sonata) by themselves did not provide acceptable levels of control. However, it is clear that combinations or rotations of the biological agents with chemical fungicides enhance disease control. No differences in yield, measured both as the number and weight of harvested fruit were found.

Example 25

BmJ and 203-7 for Virus Control in Tomatoes and Cucumber

In greenhouse trials treatment with BmJ and *Bacillus* 203-7 reduced virus titers in both cucumber and tomato with cucumber mosaic virus and tobacco mosaic virus, respectively. For experiments with each species, plants were sprayed to near-run-off with $10^7$ BmJ and 203-7 spores/ml using a hand-held sprayer 5 days prior to inoculation with the virus, and again just prior to inoculation. Plants were inoculated using plant sap from virus-infected plants for the corresponding pathosystem. In the tomato experiment, visual symptoms of the tobacco mosaic virus did not develop, but ELISA analysis revealed a reduction in virus titers for both the BmJ and the 203-7 treated plants when compared to the untreated control. The differences were expressed as a decrease in optical density at 405 nm.

TABLE 21

BmJ and 203-7 tobacco mosaic virus in tomato

| Treatment | Optical Density at 405 nm |
|---|---|
| Inoculated Control | 2.35a |
| BmJ | 1.63b |
| 203-7 | 1.11b |
| $LSD_{0.05}$ | 0.71 |

In two experiments in cucumber, reductions in both visible symptoms and virus titers were recorded when compared to the inoculated control. Disease onset was extended by 0.3 days, and percent disease was reduced from 75% to 25%. Virus titers were also reduced and were measured using optical density of individual sample wells in the ELISA assay.

TABLE 22

BmJ and 203-7 cucumber mosaic virus in cucumber.

| Treatment | Disease Symptom Onset (days) | % symptomatic plants | Symptom Expression | Optical Density at 405 nm |
|---|---|---|---|---|
| Inoculated control | 6.7 | 75 | Mosaic, Wilting | 2.37a |
| BmJ | 7.0 | 25 | Mosaic | 1.4b |
| 203-7 | 7.0 | 25 | Mosaic | 0.49c |
| $LSD_{0.05}$ | No Stats | No Stats | No Stats | 0.69 |

Example 26

BmJ Field Trial, Control of Watermelon Vein Decline (WVD), Squash Vein Yellowing Virus in Florida Watermelon vein decline is caused by the squash vein yellowing virus vectored by white flies. The Florida field trial evaluated a number of products both for white fly control and for reduction in disease symptoms. BmJ spores ($3 \times 10^{10}$ per gram) were used and applied approximately weekly at a rate of 1 ounce formulation per acre (equals to 28 gram/acre BmJ with $3 \times 10^{10}$ spores per gram). BmJ had no effect on white fly population but did show reduction in disease severity with a reduction in area under the disease progress curve. BmJ as a standalone product was equal to or in some cases superior to treatments with multiple insecticides. In the table below, some of the control for treatments containing insecticides is due to reductions in white fly population. This means that some reduction in virus infection in the plants was a result of the insecticides reducing numbers of white fly vectors, as distinguished from BmJ treatment which directly controls the disease as BmJ does not kill white fly.

Example 27

BmJ and Virus Control

Tobacco Mosaic Virus

Both tomato and tobacco plants were used in studies where plants either sprayed or not sprayed with BmJ or 203-7. Experiments were done in greenhouse using mechanical inoculation.

The reduction of virus titers following treatment with BmJ and 203-7 has been documented in multiple experiments for both cucumber and tomato with cucumber mosaic virus and tobacco mosaic virus respectively. For experiments with each species, plants were sprayed to near-run-off with $1 \times 10^7$ cfu/ml BmJ and 203-7 washed spores using a hand-held sprayer 5 days prior to inoculation with the virus, and again just prior to inoculation. Plants were inoculated using plant sap from virus-infected plants for the corresponding pathosystem.

In the tomato experiment, strong visual symptoms of the tobacco mosaic virus did not develop, but ELISA analysis revealed a reduction in virus titers and infection for both the BmJ and the 203-7 treated plants when compared to the untreated control. Tobacco inoculations were similar. The

TABLE 23

Watermelon Vein Decline, Mean Disease Severity Rating[z]

| Trt # | Treatment/Rate | Application timing[x,y] | 28 Apr | 8 May | 16 May | 23 May | 5 June | AUDPC |
|---|---|---|---|---|---|---|---|---|
| 1 | Untreated control | | 0.73[w] | 3.2 a | 4.0 a | 4.75 a | 5.0 a | 63.4 a |
| 2 | Admire Pro 10.5 oz | 0 (drench) | 0.53 | 2.83 abc | 3.25 bcd | 4.03 dc | 4.75 ab | 57.0 de |
| | Fulfill 50WG 2.75 oz | 2, 3 | | | | | | |
| | Thionex 3EC 1.33 qt | 4, 5, 8 | | | | | | |
| | Oberon 2SC 8.5 fl. oz | 6, 7 | | | | | | |
| | Knack 11EC 10 fl oz | 9 | | | | | | |
| 3 | Actigard 50WG 0.75 oz/A | A through K | 0.42 | 3.03 ab | 3.82 ab | 4.65 ab | 4.95 ab | 62.4 abc |
| 4 | Actigard 50WG 0.75 oz/A | A through K | 0.58 | 2.33 bc | 3.0 cd | 3.33 e | 4.33 c | 49.7 f |
| | Admire Pro 10.5 oz | 0 (drench) | | | | | | |
| | Fulfill 50WG 2.75 oz | 2, 3 | | | | | | |
| | Thionex 3EC 1.33 qt | 4, 5, 8 | | | | | | |
| | Oberon 2SC 8.5 fl. oz | 6, 7 | | | | | | |
| | Knack 11EC 10 fl oz | 9 | | | | | | |
| 5 | *Metarhizium anisopliae* strain F52 (11% a.i.; Tick-Ex EC) 29 oz/A | A through K | 0.8 | 2.9 ab | 3.5 abc | 4.3 abc | 4.9 ab | 59.5 bcd |
| 6 | Venom 70SG 6.0 oz | 0 (drench) | 0.58 | 2.53 abc | 3.28 bcd | 3.85 cde | 4.73 b | 55.7 e |
| | Fulfill 50WG 2.75 oz | 2, 3 | | | | | | |
| | Thionex 3EC 1.33 qt | 4, 5, 8 | | | | | | |
| | Oberon 2SC 8.5 fl. oz | 6, 7 | | | | | | |
| | Knack 11EC 10 fl oz | 9 | | | | | | |
| 7 | QRD 416 2 qt/A | A through K | 0.43 | 2.28 bc | 3.75 ab | 4.77 a | 4.95 ab | 63.2 a |
| 8 | Cabrio 20EG 16 oz | A through K | 0.65 | 1.98 c | 2.75 d | 3.63 de | 4.9 ab | 55.4 e |
| 9 | JMS Stylet Oil 0.50% | 3, 4, 5, 6, 7, 8, 9 | 0.23 | 2.0 c | 3.33 abcd | 3.93 dc | 4.7 b | 56.1 de |
| | Fulfill 50WG 2.75 oz | 2, 3 | | | | | | |
| | Thionex 3EC 1.33 qt | 4, 5, 8 | | | | | | |
| | Oberon 2SC 8.5 fl. oz | 6, 7 | | | | | | |
| | Knack 11EC 10 fl oz/A | 9 | | | | | | |
| 10 | Bmj ($3 \times 10^{10}$ spores/g *Bacillus mycoides*) 1 oz/A | A through K | 0.575 | 2.7 abc | 3.35 abcd | 4.15 bcd | 4.9 ab | 58.8 cde |
| 11 | Prev-Am 0.4% v:v (1..12) | A through K | 0.525 | 2.95 ab | 4.0 a | 4.8 a | 4.93 ab | 63.2 a |
| | | | LSD 0.09 | $P < .01$ | $P < .01$ | <0.0005 | <0.0001 | |

[z] Disease severity ratings based on scale of 0-5 where 0 = no symptoms of vein decline and 5 = plant dead.
[y] Insecticide sprays: 0 = 5 Mar (transplanting); 1 = 13 Mar; 2 = 18 Mar; 3 = 25 Mar:, 4 = 1 Apr: 5 = 8 Apr; 6 = 17 Apr; 7 = 29 Apr; 8 = 6 May; 9 = 13 May
[x] Other sprays: on A = 12 Mar; B = 19 Mar; C = 26 Mar; D = 2 Apr; E = 9 Apr; F = 16 Apr; G = 23 Apr; H = 30 Apr; I = 7 May; J = 14 May; K = 21 May
[w] Means followed by the same letter or no letter are not significantly different, LSD $P < .01$.

differences were expressed as a decrease in optical density at 405 nm (Table 24). This data represents 3 experiments with 10 plants per treatment in each experiment.

TABLE 24

Reductions in tobacco mosaic virus titer in plants treated with the potential biopesticides BmJ and 203-7.

| | Tomato | | Tobacco | |
|---|---|---|---|---|
| Treatment | % virus titer | % infection | % virus titer | % infection |
| Inoculated Control | 100 a | 100 | 100 | 100 |
| BmJ | 68 b | 65 | 48 | 33 |
| 203-7 | 47 b | 57 | 47 | 57 |
| LSD$_{0.05}$ | 21 | 15 | 23 | 19 |

In experiments on cucumber similar methods were used. Results of three repeated experiments with 10 plants per experiment showed reductions in both visible symptoms and virus titers when compared to the inoculated control. Disease onset was extended by 0.3 days, and percent disease was reduced from 75% to 25%. Virus titers were also reduced and were measured using optical density of individual sample wells in the ELISA assay Table 25.

TABLE 25

Reductions in disease and virus titer in cucumber plants treated with BmJ and 203-7 prior to inoculation with cucumber mosaic virus.

| Treatment | Disease Symptom Onset (days) | % symptomatic plants | Symptom Expression | % virus titer |
|---|---|---|---|---|
| Inoculated control | 6.7 | 75 | Mosaic, Wilting | 100 a |
| BmJ | 7.0 | 25 | Mosaic | 58 b |
| 203-7 | 7.0 | 25 | Mosaic | 16 c |
| LSD$_{0.05}$ | No Stats | No Stats | No Stats | 18 |

Potato Virus X
In 3 separate mechanical inoculation trials we were unable to demonstrate control of PVX. Further trials are needed to confirm the results as we do not understand why we failed to obtain control of Potato Virus X.
Potato Virus Y
(1) Greenhouse Test
Trial 1 Mechanical Transmission Experiments were done in a greenhouse using mechanical transmission. The mechanical transmission was performed by using sap from infected plants which were grounded by mortar and pestle in phosphate buffer on ice. Carborundum was used to pick up the sap and rub the sap on leaves of plants. Plants were sprayed to near-run-off with BmJ washed spores ($1 \times 10^7$ cfu/ml) using a hand-held sprayer 5 days before virus inoculation and at 14, 28, and 42 days post inoculation. The results indicate that BmJ is effective in controlling PVY.

TABLE 26

PVY Greenhouse Test

| Treatment | % PVY Trial 1 | % PVY Trial 2 | % PVY Trial 3 | Average PVY |
|---|---|---|---|---|
| Dead BmJ + PVY | 25 | 50 | 100 | 58.3 a |
| No PVY | 0 | 0 | 0 | 0 c |
| BmJ induction 5 days before inoculation with PVY + BmJ @ 14, 28, and 42 days post inoculation | 5 | 0 | 75 | 26.6 b |

Figure 6:
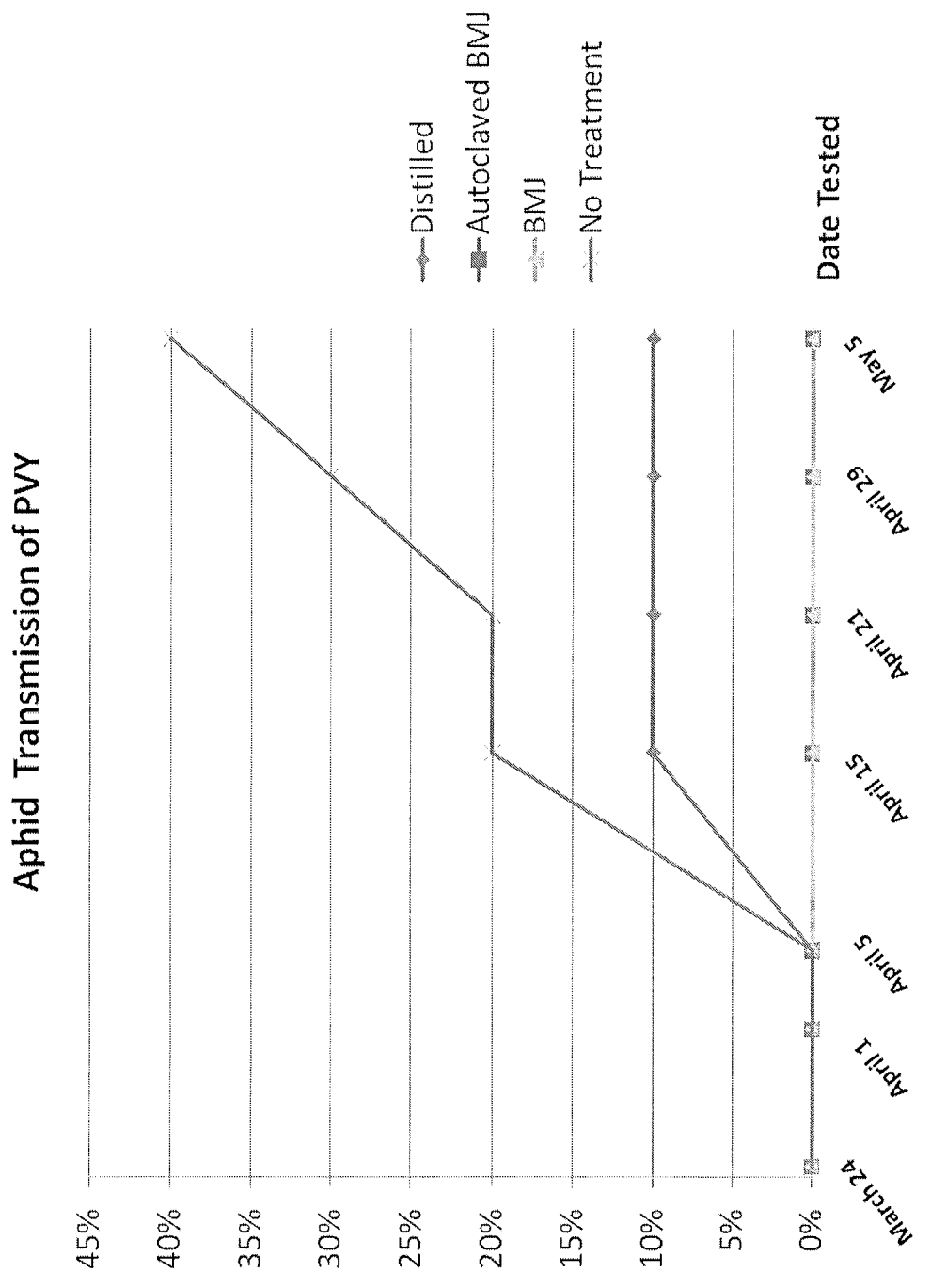

The results indicate that BmJ can induce resistance to PVY in plants.
Trial 2 Aphid Transmission Greenhouse aphid transmission experiments were conducted. The experiments were repeated three times. Washed BmJ spores at $1 \times 10^7$ cfu/ml were sprayed on the plants 5 days before and 14 days after the aphid transmission. Ten green peach aphids from PVY infected potato plants were transferred to each plant. Twenty replications for each treatment were used. The results are shown in FIG. 6.

It is interesting that both live and dead BmJ applications resulted in total control of aphid transmission. The results indicate that BmJ (either dead or alive) can reduce PVY infection in plants transmitted by insects. Therefore, BmJ can be used as repellence against insects such as aphids.
(2) Natural Infection (Aphid Transmission) Test
Trial 1

Field trial was conducted at Hermiston, Oreg. to test the ability of BmJ to control natural PVY infection transmitted by aphids. Plants were either sprayed or not sprayed every 14 days with $1 \times 10^7$ cfu/ml (15 gal/A).
Trial 2

Figure 5:
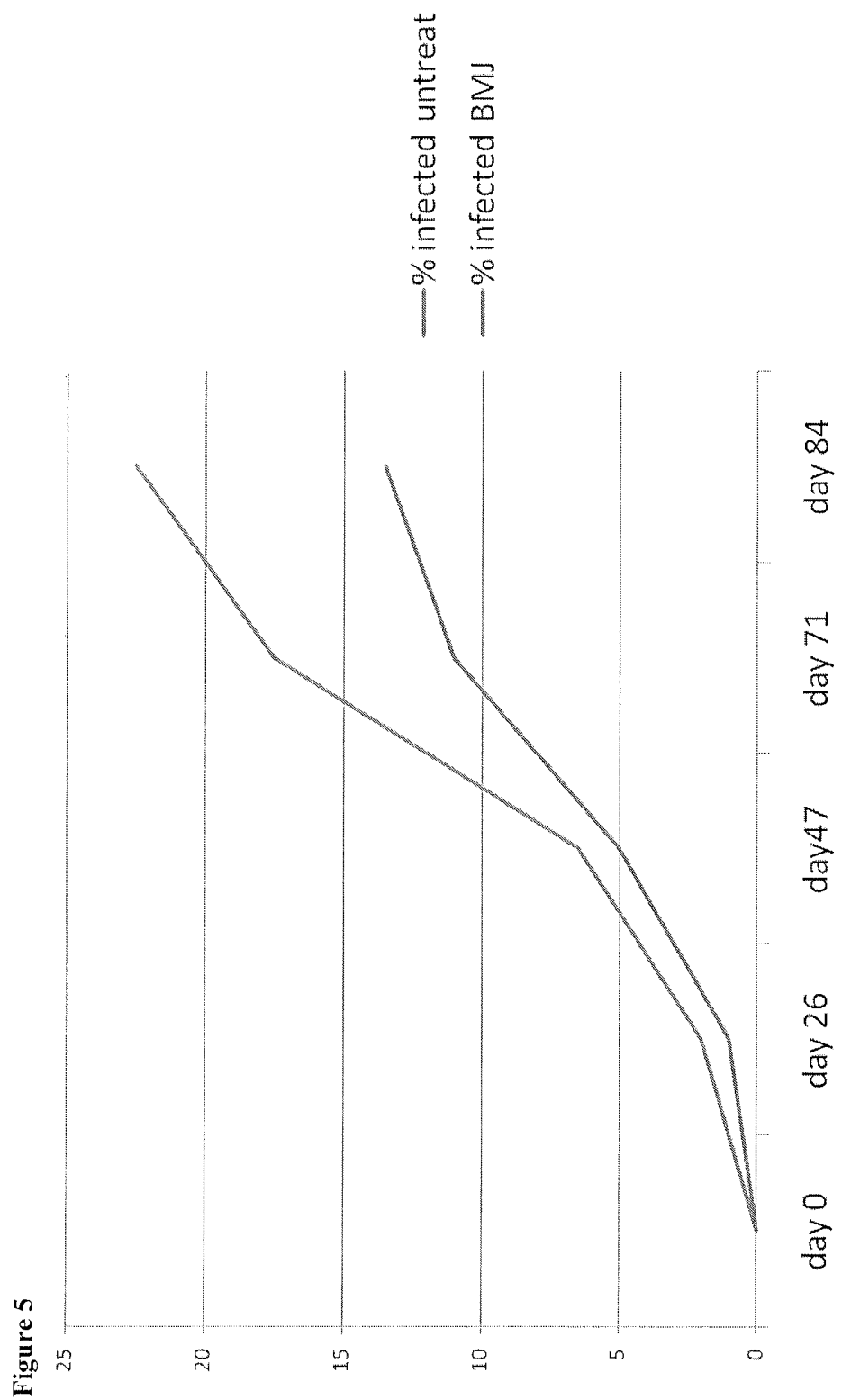

Another field trial was conducted at Hermiston, Oreg. to test the ability of BmJ to control natural PVY infection transmitted by aphids. The results are shown in Table 27 below and FIG. 5.

TABLE 27

Incidence of Potato Virus Y infection in Ranger potato as affected by *Bacillus mycoides* isolate J (BmJ), rouging and insecticide treatments.

| Treatment | % PVY 6/6 | % PVY 7/14 | % PVY 8/18 | % PVY 9/14 | % PVY 12/15 | % PVY total |
|---|---|---|---|---|---|---|
| BmJ spores ($3 \times 10^{10}$ spores per gram) applied at 2.0 oz/A (56 gram/acre) emergence and every 14 days till 9/14 | 0 | 0 | 1 | 2 | 1.5 | 3.5 |
| BmJ spores ($3 \times 10^{10}$ spores per gram) applied at 2.0 oz/A (56 gram/acre) emergence and every 14 days till 9/14 + rouging of PVY positive plants | 0 | 0 | 1 | 1.5 | 0 | 1.5 |

TABLE 27-continued

Incidence of Potato Virus Y infection in Ranger potato as affected by *Bacillus mycoides* isolate J (BmJ), rouging and insecticide treatments.

| Treatment | % PVY 6/6 | % PVY 7/14 | % PVY 8/18 | % PVY 9/14 | % PVY 12/15 | % PVY total |
|---|---|---|---|---|---|---|
| Admire Pro 8.7 oz/A at plant + BmJ spores (3 × 10$^{10}$ spores per gram) applied at 2.0 oz/A (

*mopara viticola* in grapevines. European Journal of Plant Pathology 105 (1999), pp. 351-361.
9. Y R Cohen, β-aminobutyric acid-induced resistance against plant pathogens. Plant Disease 86 (2002), pp. 448-457.
10. T P Delaney, Genetic dissection of acquired resistance to disease. Plant Physiology 113 (1997), pp. 5-12.
11. N Doke, Generation of superoxide anion by potato tuber protoplasts during the hypersensitive response to hyphal wall components of *Phytophthora infestans* and specific inhibition of the reaction by suppressors of hypersensitivity. Physiological Plant Pathology 23 (1983), pp. 359-367
12. J E Duffus and E G Ruppel, Diseases. In: D A Cooke and R K Scott, Editors, Diseases in the Sugarbeet Crop, Chapman and Hall, London (1993), pp. 346-427.
13. S Gallagher, S E Winston, A Fuller and J G R Hurrell, Immunoblotting and Immunodeteetion. In: F M Ausubel, R Brent, R E Kingston, D D Moore, J G Seidman, J A Smith and K Struhl, Editors, Current Protocols in Molecular Biology, John Wiley and Sons, Inc, New York (1997), pp. 10.8.1-10.8.16.
14. T E Gottschalk, J D Mikkelsen, K K Nielsen and J Brunstedt, Immunolocalization and characterization of a (β-1,3-glucanase from sugar beet, deduction of its primary structure and nucleotide sequence by cDNA and genomic cloning. Plant Science 132 (1998), pp. 153-167.
15. R Hammerschmidt, E M Nuckles and J Kuc, Association of enhanced peroxidase activity with induced resistance of cucumber to *Colletotrichum lagenarium*. Physiological Plant Pathology 20 (1982), pp. 73-82.
16. R Hofstein and A Chapple, Commercial development of biofungicides. In: F R Hall and J J Menn, Editors, Biopesticides: Use and Delivery, Humana Press, Totowa (1999), pp. 77-102.
17. S W Hutcheson, Current concepts of active defense in plants. Annual Review of Phytopathology 36 (1998), pp. 59-90.
18. B J Jacobsen, N K Zidack, J Ansley, B Larson, J L A Eckhoff and J Bergman, Integrated management of *cercospora* leaf spot. Sugarbeet Research and Extension Reports 32 (2001), pp. 317-320.
19. E Jongedijk, H Tigelaar, J S C van Roekel, S A Bres-Vloemans, I Dekker, P J M van den Elzen, B J C Cornelissen and L S Melchers, Synergistic activity of chitinases and (β-1,3-glucanases enhances fungal resistance in transgenic tomato plants. Euphytica 85 (1995), pp. 173-180.
20. Kleinwanzler Saatzucht, Ag, Einbeck, 1970, *Cercospora* Tafel. Kleinwanzleber Saatzacht Ag, 14 p
21. K Klement, Method of obtaining fluid from the intercellular spaces of foliage and the fluid's merit as substrate for phytobacterial pathogens. Phytopathology 55 (1965), pp. 1033-1034.
22. N Kokalis-Burelle, P A Backman, R Rodriquez-Kabana and L D Ploper, Potential for biological control of early leafspot of peanut using *Bacillus cereus* and chitin as foliar amendments. Biological Control 2 (1992), pp. 321-328.
23. J Kuc, Induced immunity to plant disease. BioScience 32 (1992), pp. 854-860.
24. M Legrand, S Kauffmannn, P Geoffroy and B Fritig, Biological function of pathogenesis-related proteins: four tobacco pathogenesis-related proteins are chitinases. Proceedings of the National Academy of the Sciences, USA 84 (1987), pp. 6750-6754.
25. T Lotan, N Ori and R Fluhr, Pathogenesis-related proteins are developmentally regulated in tobacco flowers. The Plant Cell 1 (1989), pp. 881-887.
26. T Maniatis, E F Fritsch and J. Sambrock. Molecular Cloning: A Laboratory Manual, Cold Spring Harbor Laboratory, Cold Spring Harbor (1982) p. 18.56-18.57.
27. F Mauch, B Mauch-Mani and T Boller, Antifungal hydrolases in pea tissue. Plant Physiology 88 (1988), pp. 936-942.
28. J-P Metraux and T h Boller, Local and systemic induction of chitinase in cucumber plants in response to viral, bacterial and fungal infections. Physiological and Molecular Plant Pathology 28 (1986), pp. 161-169.
29. J-P Metraux, P Ahl-Goy, T Staub, J Speich, A Steinemann, J Ryals and E Ward, Induced resistance in cucumber in response to 2,6-dichloroisonicotinic acid and pathogens. In: H Hennecke and DP S Verma, Editors, Advances in Molecular Genetics of Plant-Microbe Interactions, Vol. 1, Kluwer Academic Publishers, Dordrecht (1991), pp. 432-439.
30. B M Moerschbacher, Plant peroxidases: involvement in response to pathogens. In: C Penel, T h Gaspar and H Greppin, Editors, Plant Peroxidases 1980-1990, Topics and Detailed Literature on Molecular, Biochemical and Physiological Aspects, University of Geneva Press, Geneva (1992), pp. 91-99.
31. J F Murphy, G W Zehnder, D J Schuster, E J Sikora, J E Polston and J W Kloepper, Plant growth-promoting rhizobacterial mediated protection in tomato against Tomato mottle virus. Plant Disease 84 (2000), pp. 779-784.
32. A Navarro, P Manzanares, J V Carbonell and J M Sendra, Determination of (1 leads to 3), (1 leads to 4)-β-glucanase activity by a Calcofluor-flow injection analysis method. Journal of Cereal Science 22 (1995), pp. 275-284.
33. N Nelson, A photometric adaptation of the Somogyi method for the determination of glucose. Journal of Biological Chemistry 153 (1994), pp. 375-380.
34. J M Neuhaus, S Flores, D Keefe, P Ahl-Goy and F Meins, Jr., The function of vacuolar β-1,3-glucanase investigated by antisense transformation. Susceptibility of transgenic *Nicotiana sylvestris* plants to *Cercospora nicotianae* infection. Plant Molecular Biology 19 (1992), pp. 803-813.
35. Y Oka, Y Cohen and Y Spiegel, Local and systemic induced resistance to the root-knot nematode in tomato by DL-β-amino-n-butyric acid. Phytopathology 89 (1999), pp. 1138-1143.
36. C M J Pieterse, S C M van Wees, E Hoffland, J A van Pelt and L C van Loon, Systemic resistance in *Arabidopsis* induced by biocontrol bacteria is independent of salicylic acid accumulation and pathogenesis-related gene expression. The Plant Cell 8 (1996), pp. 1225-1237.
37. C M J Pieterse, S C M van Wees, J A van Pelt, M Knoester, R Laan, H Gerrits, P J Weisbeek and L C van Loon, A novel signaling pathway controlling induced systemic resistance in *arabidopsis*. The Plant Cell 10 (1998), pp. 1571-1580.
38. Z K Punja, Genetic engineering of plants to enhance resistance to fungal pathogens—a review of progress and future prospects. Canadian Journal of Plant Pathology 23 (2001), pp. 216-235.
39. R A Reisfeld, U J Lewis and D E Williams, Disk electrophoresis of basic proteins and peptides on polyacrylamide gels. Nature 195 (1962), pp. 281-283.
40. A F Ross, Localized acquired resistance to plant virus infection in hypersensitive hosts. Virology 14 (1961a), pp. 329-339.
41. A F Ross, Systemic acquired resistance induced by localized virus infection in plants. Virology 14 (1961b), pp. 340-358.

42. J A Ryals, U H Neuenschwander, M G Willits, A Molina, H Y Steiner and M D Hunt, Systemic acquired resistance. The Plant Cell 8 (1996), pp. 1809-1819.
43. L Sequeira, Mechanisms of induced resistance in plants. Annual Review of Microbiology 37 (1983), pp. 51-79.
44. K P Smith, J Handelsman and R M Goodman, Modeling dose-response relationships in biological control: partitioning host responses to the pathogen and biocontrol agent. Phytopathology 87 (1997), pp. 720-729.
45. M Somogyi, Notes on sugar determination. Journal of Biological Chemistry 195 (1952), pp. 19-23.
46. J P Stack, Biological management of postharvest diseases. Phytopathology 92 (2002), p. S 106.
47. J C Sutton and G Peng, Manipulation and vectoring of biocontrol organisms to manage foliage and fruit diseases in cropping systems. Annual Review of Phytopathology 31 (1993), pp. 473-493.
48. A Tally, M Oostendorp, K Lawton, T Staub and B Bassi, Commercial development of elicitors of induced resistance to pathogens. In: A A Agrawal, S Tuzun and E Bent, Editors, Induced Plant Defenses Against Pathogens and Herbivores, APS Press, St Paul (1999), pp. 299-318.
49. S Thamthiankul, S Suan-Ngay, S Tantimavanich and W Panbangred, Chitinase from *Bacillus thurigiensis* subsp. *Pakistani*. Applied Microbiology and Biotechnology 56 (2001), pp. 395-401.
50. J Trudel and A Asselin, Detection of chitinase activity after polyacrylamide gel electrophoresis. Analytical Biochemistry 178 (1989), pp. 362-366.
51. L C van Loon, Occurrence and properties of plant pathogenesis-related proteins. In: A A Agrawal, S Tuzun and S Bent, Editors, Induced Plant Defenses Against Pathogens and Herbivores, APS Press, St Paul (1999), pp. 1-19.
52. L C van Loon and E A van Strien, The families of pathogenesis-related proteins, their activities, and comparative analysis of PR-1 type proteins. Physiological and Molecular Plant Pathology 55 (1999), pp. 85-97.
53. L C van Loon and C M J Pieterse, Biological control agents in signaling resistance. In: S S Gnanamanickan, Editor, Biological Control of Crop Diseases, Mercel Dekker, New York (2002), pp. 355-386.
54. R van Peer, G J Niemann and B Schippers, Induced resistance and phytoalexin accumulation in biological control of *fusarium* wilt of carnation by *Pseudomonasa* sp. strain WCS417r. Phytopathology 81 (1991), pp. 728-734.
55. L Velasquez. The Pathogenesis-related Protein Chitinase, and its Role in the Systemic Acquired Resistance Phenotype in Cucumber Plants (*Cucumis sativus* L.), Michigan State University (2002) p. 25-49.
56. G Wei, J W Kloepper and S Tuzun, Induction of systemic resistance of cucumber to *Colletotrichum orbiculare* by select strains of plant growth-promoting rhizobacteria. Phytopathology 81 (1991), pp. 1508-1512. Full Text via CrossRef
57. D M Weller, Biological control of soil-borne plant pathogens in the rhizosphere with bacteria. Annual Review of Phytopathology 26 (1988), pp. 379-407.
58. R F White, Acetylsalicylic acid (aspirin) induces resistance to tobacco mosaic virus in tobacco. Virology 99 (1979), pp. 410-412.
59. C E Windels, H A Lamey, D Hilde, J Widner and T Knudsen, A *Cercospora* leaf spot model for sugar beet: In practice by an industry. Plant Disease 82 (1998), pp. 716-726. Full Text via CrossRef View Record in Scopus|Cited By in Scopus (28)
60. S Zhang, M S Reddy, N Kokalis-Burelle, L W Wells, S P Nightengale and J W Kloepper, Lack of induced systemic resistance in peanut to late leaf spot disease by plant growth-promoting rhizobacteria and chemical elicitors. Plant Disease 85 (2001), pp. 879-884. Full Text via CrossRef|View Record in Scopus|Cited By in Scopus (13)
61. Q Zu, A Maher, S Masoud, R A Dixon and C Lamb, Enhanced protection against fungal attack by constitutive coexpression of chitinase and glucanase genes in transgenic tobacco. Bio Technology 12 (1994), pp. 807-812.
62. Bargabus, R. L., Zidack, N. K., Sherwood, J. E., Jacobsen, B J., 2003. Characterization of systemic resistance in sugar beet elicited by a non-pathogenic, phyllosphere-colonizing *Bacillus mycoides*, biological control agent. Physiological and molecular plant pathology 61: 289-298.
63. Bargabus, R. L., Zidack, N. K, Sherwood, I E., Jacobsen, B J., 2004. Screening for the identification of potential biological control agents that induce systemic acquired resistance in sugar beet. Biological Control 30: 342-350.
64. Bargabus-Larson, R. L. and BJ. Jacobsen, 2007. Biocontrol elicited systemic resistance in sugarbeet is salicylic acid independent and npr1 dependent|Sugar Beet Res. 44: 17-33.
65. Ewing, J. F., Janero, D. R., 1995. Microplate superoxide dismutase assay employing a nonenzymatic superoxide generator. Analytical Biochemistry 232: 243-248.
66. Hung, T.-H., Chang, Y.-M., Sung, H.-Y., Chang, C.-T., 2002. Purification and Characterization of hydrolase with chitinase and chitosanase activity from commercial stem bromelain. Journal of Agricultural and Food Chemistry 50: 4666-4673.
67. Jacobsen, B.1. 2006. Biological control of plant diseases by phyllosphere applied biological control agents. p. 133-148, In: Microbial Ecology of Aerial Plant Surfaces, (Ed) M. Baily et al. CAB International, Cambridge, Mass. 315 p.
68. Jacobsen, B. 1., C. Bradley, N. Zidack, T. Brenneman, 1 Miller, 1 Washington, C. Melinger, B. Larson and a. Neher. 2007. Commercialization of *Bacillus mycoides* isolate BmJ as a broad spectrum biological plant disease control agent. Phytopathology 97: S50
69. Pieterse, C. M. 1., van Wees, S. C. M., van Pelt, I A, Knoester, M., Laan, R., Gerrits, H., Weisbeek, P. 1., van Loon, L.c., 1998. A novel signaling pathway controlling induced systemic resistance in *Arabidopsis*. Plant Cell 10: 1571-1580.
70. Verhagen, B. W. M., van Loon, L.c., Pieterse, C. M. 1., 2006. Induced disease resistance in plants. pp 334-343. In: Floriculture, ornamental and plant biotechnology, (Ed) Teixeira da Silva, IA Global Science Books ltd, UK.
71. Xiao, Z. Z., Storms, R., Tsang, A, 2005. Microplate-based carboxymethylcellulose assay for endoglucanase activity. Analytical Biochemistry 342: 176-178.
72. Zietlow, a. T., M. R. Johnston, N. K. Zidack and B. 1. Jacobsen. 2004. Induced systemic resistance in cucumber to *Glomerella cingulata* var. *obiculare* and *Pseudomonas syringae* pv. *lachrymans* by *Bacillus pumilis*, isolate MSU 203-7. Phytopathology 94: S 117.

I claim:

1. A method of inducing disease resistance to infection in a plant, comprising applying a *Bacillus* control agent comprising *Bacillus mojavensis* isolate 203-7 having accession number NRRL B-30893 to the plant, wherein the plant is capable of producing defense proteins, and wherein the disease resistance is salicylic acid independent.

2. The method of claim 1 wherein the disease resistance to infection is induced systemic resistance.

3. The method of claim 2 wherein the induced systemic resistance is induced in the plant through a jasmonic acid dependent pathway.

4. The method of claim 2 wherein the induced systemic resistance is induced by *Bacillus mojavensis* 203-7 isolate having accession number NRRL B-30893 in the plant through an NPR1 independent pathway.

5. The method of claim 1 wherein the plant is a dicot.

6. The method of claim 5 wherein the dicot is selected from the group consisting of sugar beet, Solanaceae species, Curcubitaceae species, and ornamental plants.

7. The method of claim 6 wherein the plant is a Solanaceae species selected from the group consisting of potato, tomato, and tobacco.

8. The method of claim 6 wherein the Cucurbitaceae species plant is cucumber.

9. The method of claim 6 wherein the plant is an ornamental Geranium species.

10. The method of claim 1, wherein the infection is caused by a pathogen selected from the group consisting of bacteria, fungi, and viruses.

11. The method of claim 10, wherein the pathogen is selected from the group consisting of *Cercospora beticola*, Anthracnose disease (*Glomerella cingulata*), angular leaf spot (*Pseudomonas* syringe), gray mold (*Botrytis cinerea*), root rotting disease (*Pythium aphanidermatum*), cucumber mosaic virus, and tobacco mosaic virus.

12. A non-naturally occurring composition comprising a *Bacillus mojavensis* isolate 203-7 having accession number NRRL B-30893, wherein said composition is in a spray-dried formulation.

13. The composition of claim 12, where said composition comprises at least one component from the group consisting of: a carrier, a biological control agent, and a chemical control agent.

14. The composition of claim 12, wherein the spray-dried formulation is suspended in water before inoculation to a plant or a plant part.

15. The composition of claim 14, wherein the composition comprises at least $1 \times 10^7$ cfu/ml of *Bacillus mojavensis* isolate 203-7.

16. The composition of claim 14, wherein the composition comprises at least one component from the group consisting of: a carrier, a biological control agent, and a chemical control agent.

* * * * *